United States Patent
Tonon et al.

(10) Patent No.: US 10,017,767 B2
(45) Date of Patent: Jul. 10, 2018

(54) TARGETS IN MULTIPLE MYELOMA AND OTHER DISORDERS

(71) Applicants: FONDAZIONE CENTRO SAN RAFFAELE, Milan (IT); DANA-FARBER CANCER INSTITUTE, INC., Boston, MA (US)

(72) Inventors: Giovanni Tonon, Milan (IT); Francesca Cottini, Boston, MA (US); Kenneth Carl Anderson, Wellesley, MA (US)

(73) Assignees: FONDAZIONE CENTRO SAN RAFFAELE, Milan (IT); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 14/440,744

(22) PCT Filed: Nov. 5, 2013

(86) PCT No.: PCT/IB2013/059908
§ 371 (c)(1),
(2) Date: May 5, 2015

(87) PCT Pub. No.: WO2014/068542
PCT Pub. Date: May 8, 2014

(65) Prior Publication Data
US 2015/0252368 A1 Sep. 10, 2015

Related U.S. Application Data

(60) Provisional application No. 61/722,518, filed on Nov. 5, 2012.

(51) Int. Cl.
| | |
|---|---|
| *C12N 15/113* | (2010.01) |
| *C07K 16/32* | (2006.01) |
| *C12Q 1/6883* | (2018.01) |
| *G01N 33/50* | (2006.01) |
| *G01N 33/573* | (2006.01) |

(52) U.S. Cl.
CPC .......... *C12N 15/1137* (2013.01); *C07K 16/32* (2013.01); *C12N 15/113* (2013.01); *C12Q 1/6883* (2013.01); *C12Y 207/11001* (2013.01); *G01N 33/5011* (2013.01); *G01N 33/5091* (2013.01); *G01N 33/573* (2013.01); *C12N 2310/14* (2013.01); *C12N 2310/141* (2013.01); *C12N 2310/531* (2013.01); *C12N 2320/30* (2013.01); *C12Q 2600/118* (2013.01); *C12Q 2600/158* (2013.01); *G01N 2333/4706* (2013.01); *G01N 2500/02* (2013.01); *G01N 2500/10* (2013.01)

(58) Field of Classification Search
CPC ............... C12N 15/1137; C07K 16/32; C12Y 207/11001
See application file for complete search history.

(56) References Cited

U.S. PATENT DOCUMENTS

| | | | |
|---|---|---|---|
| 8,795,988 B2 | 8/2014 | Liu | |
| 2004/0213794 A1* | 10/2004 | Vatner ................... | A61K 38/45 424/155.1 |
| 2007/0154916 A1 | 7/2007 | Inazawa et al. | |
| 2009/0087910 A1 | 4/2009 | Liu | |

FOREIGN PATENT DOCUMENTS

WO 2012/044921 4/2012

OTHER PUBLICATIONS

Dai et al. Blood (2011) 117:1947-1957.*
Peter C. Trask et al: "Health-related quality of life of bosutinib (SKI-606) in imatinib-resistant or imatinib-intolerant chronic phase chronic myeloid leukemia", Leukemia Research, vol. 36, No. 4, Oct. 28, 2011 (Oct. 28, 2011), pp. 438-442, XP55104520, ISSN: 0145-2126, 001: 10.1016/j.leukres.2011.10.011 abstract.
J. E. Cortes et al: "Safety and efficacy of bosutinib (SKI-606) in chronic phase Philadelphia chromosome-positive chronic myeloid leukemia patients with resistance or intolerance to imatinib", Blood, vol. 118, No. 17, Aug. 24, 2011 (Aug. 24, 2011), pp. 4567-4576, XP55104438, ISSN: 0006-4971, DOI: 10. 1182/blood-2011-05-355594 abstract.
T.-S. Kim et al: "Mammalian Sterile 20-like Kinase 1 Suppresses Lymphoma Development by Promoting Faithful Chromosome Segregation", Cancer Research, vol. 72, No. 20, Aug. 27, 2012 (Aug. 27, 2012), pp. 5386-5395, XP55104667, ISSN: 0008-5472, DOI: 10.1158/0008-5472.CAN-11-3956 figures 4-6.
Lina Jansson et al: II Normal Hematopoietic Stem Cell Function in Mice with Enforced Expression of the Hippo Signaling Effector YAP1, Plos One, vol. 7, No. 2, Feb. 21, 2012 (Feb. 21, 2012), p. e32013, XP55104493, ISSN: 1932-6203, DOI: 10.1371/journal.pone.0032013 the whole document.
L. Van Der Weyden et al: "Loss of Rassf1a Synergizes with Deregulated Runx2 Signaling in Tumorigenesis", Cancer Research, vol. 72, No. 15, Jun. 18, 2012 (Jun. 18, 2012) , pp. 3817-3827, XP55104397, ISSN: 0008-5472, DOI: 10.1158/0008-5472.CAN-11-3343 abstract; figures 3,5.
A. Von Gise et al: "YAP1, the nuclear target of Hippo signaling, stimulates heart growth through cardiomyocyte proliferation but not hypertrophy", Proceedings of the National Academy of Sciences, vol. 109, No. 7, Jan. 30, 2012 (Jan. 30, 2012), pp. 2394-2399, XP55104402, ISSN: 0027-8424, DOI: 10.1073/pnas.1116136109 p. 2396; figures 3,4.
Bin Zhao et al: "Mst Out and HCC in", Cancer Cell, vol. 16, No. 5, Nov. 3, 2009 (Nov. 3, 2009), pp. 363-364, XP55104407, ISSN: 1535-6108, DOI: 10.1016/j.ccr.2009.10.008 the whole document.
Dawang Zhou et al: "Mst1 and Mst2 Maintain Hepatocyte Quiescence and Suppress Hepatocellular Carcinoma Development through Inactivation of the Yap1 Oncogene", Cancer Cell, vol. 16, No. 5, Nov. 3, 2009 (Nov. 3, 2009), pp. 425-438, XP55104411, ISSN: 1535-6108, DOI: 10.1016/j.ccr.2009.09.026 figure 4.
D. Zhou et al: "PNAS Plus: Mst1 and Mst2 protein kinases restrain intestinal stem cell proliferation and colonic tumorigenesis by (Continued)

*Primary Examiner* — J. E. Angell
(74) *Attorney, Agent, or Firm* — Steptoe & Johnson LLP

(57) ABSTRACT

An agent that increases YAP1 levels for use in the treatment of hematopoietic disorders.

11 Claims, 46 Drawing Sheets

(56) References Cited

OTHER PUBLICATIONS inhibition of Yes-associated protein (Yap) overabundance", Proceedings of the National Academy of Sciences, vol. 108, No. 49, Dec. 6, 2011 (Dec. 6, 2011), pp. E1312-E1320, XP55067289, ISSN: 0027-8424, DOI: 10.1073/pnas.1110428108 the whole document.
J. D. Graves: "Both Phosphorylation and Caspase-mediated Cleavage Contribute to Regulation of the Ste20-like Protein Kinase Mst1 during CD95/Fas-induced Apoptosis", Journal of Biological Chemistry, vol. 276, No. 18, Feb. 13, 2001 (Feb. 13, 2001), pp. 14909-14915, XP55104668, ISSN: 0021-9258, DOI: 10. 1074/jbc. 010905200 figure 5.
Rabindran S K et al: "Antitumor Activity of HKI-272, an Orally Active, Irreversible Inhibitor of the HER-2 Tyrosine Kinase", Cancer Research, American Association for Cancer Research, US, vol. 64, No. 11, Jun. 1, 2004 (Jun. 1, 2004), pp. 3958-3965, XP002318446, ISSN: 0008-5472, DOI: 10.1158/0008-5472.CAN-03-2868 abstract.
Cottini F et al: "The Role of the ABL1/YAP1/P73 Axis in Prevention of DNA Damage-Mediated Apoptosis in Multiple Myeloma", Blood, vol. 20, No. 21, Nov. 16, 2012 (Nov. 16, 2012), p. 725, XP055104532, US ISSN: 0006-4971 abstract.
International Search Report and Written Opinion of the International Searching Authority of PCT/IB2013/059908, dated Mar. 6, 2014 (Mar. 6, 2014), the whole document.
Polak J. M. and James O'D. McGee, 1990, In Situ Hybridization: Principles and Practice; Oxford University Press.
Roe B. , J. Crabtree, and A. Kahn, 1996, DNA Isolation and Sequencing: Essential Techniques, John Wiley & Sons.
Sambrook J, E. F. Fritsch, and T. Maniatis, 1989, Molecular Cloning: A Laboratory Manual, Second Edition, Books 1-3, Col d Spring Harbor Laboratory Press.
Santa Cruz, sc-131 (K12) http://www.scbt.com/datasheet-131-c-abl-k-12-antibody.html.
Shafman, T., Khanna, K. K., Kedar, P., Spring, K., Kozlov, S., Yen, T., Hobson, K., Gatei, M., Zhang, N., Watters, D., et al. (1997). Interaction between ATM protein and c-Abl in response to DNA damage. Nature 387, 520-523.
Stegmeier F et al. A lentiviral microRNA-based system for single-copy polymerase II-regulated RNA interference in mammalian cells. Proc Natl Acad Sci USA 102: 13212-13217, 2005.
Strano, S., Monti, O., Pediconi, N., Baccarini, A., Fontemaggi, G., Lapi, E., Mantovani, F., Damalas, A., Citro, G., Sacchi, A., et al. (2005). The transcriptional coactivator Yes-associated protein drives p73 gene-target specificity in response to DNA Damage. Mol Cell 18, 447-459.
Strano, S., Munarriz, E., Rossi, M., Castagnoli, L., Shaul, Y., Sacchi, A., Oren, M., Sudol, M., Cesareni, G., and Blandino, G. (2001). Physical interaction with Yes-associated protein enhances p73 transcriptional activity. J Biol Chem 276, 15164-15173.
Sudol, M. (1994). Yes-associated protein (YAP65) is a proline-rich phosphoprotein that binds to the SH3 domain of the Yes proto-oncogene product. Oncogene 9, 2145-2152.
Sui G et al. A DNA vector-based RNAi technology to suppress gene expression in mammalian cells. Proc Natl Acad Sci USA 99: 5515-5520, 2002.
Taagepera, S., McDonald, D., Loeb, J. E., Whitaker, L. L., McElroy, A. K., Wang, J. Y., and Hope, T. J. (1998). Nuclear-cytoplasmic shuttling of C-ABL tyrosine kinase. Proc Natl Acad Sci USA 95, 7457-7462.
Takacova, S., Slany, R., Bartkova, J., Stranecky, V., Dolezel, P., Luzna, P., Bartek, J., and Divoky, V. (2012). DNA damage response and inflammatory signaling limit the MLL-ENL-induced leukemogenesis in vivo. Cancer Cell 21, 517-531.
Walker, B. A., Leone, P. E., Chiecchio, L., Dickens, N. J., Jenner, M. W., Boyd, K. D., Johnson, D. C., Gonzalez, D., Dagrada, G. P., Protheroe, R. K., et al. (2010). A compendium of myeloma-associated chromosomal copy number abnormalities and their prognostic value. Blood 116, e56-65.
Walters, D. K., Wu, X., Tschumper, R. C., Arendt, B. K., Huddleston, P. M., Henderson, K. J., Dispenzieri, A., and Jelinek, D. F. (2011). Evidence for ongoing DNA damage in multiple myeloma cells as revealed by constitutive phosphorylation of H2AX. Leukemia 25, 1344-1353.
White, E., and Prives, C. (1999). DNA damage enables p73. Nature 399, 734-735, 737.
Witzig, T. E., Timm, M., Larson, D., Therneau, T., and Greipp, P. R. (1999). Measurement of apoptosis and proliferation of bone marrow plasma cells in patients with plasma cell proliferative disorders. Br J Haematol 104, 131-137.
Xu-Monette, Z. Y., Medeiros, L. J., Li, Y., Orlowski, R. Z., Andreeff, M., Bueso-Ramos, C. E., Greiner, T. C., McDonnell, T. J., and Young, K. H. (2012). Dysfunction of the TP53 tumor suppressor gene in lymphoid malignancies. Blood 119, 3668-3683.
Yao Z, Seger R., Immunological detection of phosphorylation, Curr Protoc Cell Biol. May 2001; Chapter 14: Unit 14.2.
Yoshida, K., Yamaguchi, T., Natsume, T., Kufe, D., and Miki, Y. (2005). JNK phosphorylation of 14-3-3 proteins regulates nuclear targeting of c-Abl in the apoptotic response to DNA damage. Nat Cell Biol 7, 278-285.
Yuan, Z. M., Huang, Y., Ishiko, T., Kharbanda, S., Weichselbaum, R., and Kufe, D. (1997). Regulation of DNA damage-induced apoptosis by the c-Abl tyrosine kinase. Proc Natl Acad Sci USA 94, 1437-1440.
Yuan, Z. M., Huang, Y., Whang, Y., Sawyers, C., Weichselbaum, R., Karbanda, S., and Kufe, D. (1996). Role for c-Abl tyrosine kinase in growth arrest response to DNA damage. Nature 382, 272-274.
Zender, L., Spector, M. S., Xue, W., Flemming, P., Cordon-Cardo, C., Silke, J., Fan, S. T., Luk, J. M., Wigler, M., Hannon, G. J., et al. (2006). Identification and validation of oncogenes in liver cancer using an integrative oncogenomic approach. Cell 125, 1253-1267.
Zhou, D., Conrad, C., Xia, F., Park, J. S., Payer, B., Yin, Y., Lauwers, G. Y., Thasler, W., Lee, J. T., Avruch, J., et al. (2009). Mst1 and Mst2 maintain hepatocyte quiescence and suppress hepatocellular carcinoma development through inactivation of the Yap1 oncogene. Cancer Cell 16, 425-438.
Zhou, D., Zhang, Y., Wu, H., Barry, E., Yin, Y., Lawrence, E., Dawson, D., Willis, J. E., Markowitz, S. D., Camargo, F. D., et al. (2011). Mst1 and Mst2 protein kinases restrain intestinal stem cell proliferation and colonic tumorigenesis by inhibition of Yes-associated protein (Yap) overabundance. Proc Natl Acad Sci USA 108, E1312-1320.
Two bright new faces in gene therapy, Nature Biotechnology 1996 14; 556.
Anastassiadis, T., Deacon, S. W., Devarajan, K., Ma, H., and Peterson, J. R. (2011). Comprehensive assay of kinase catalytic activity reveals features of kinase inhibitor selectivity. Nature biotechnology 29, 1039-1045.
Annunziata, C. M., Davis, R. E., Demchenko, Y., Bellamy, W., Gabrea, A., Zhan, F., Lenz, G., Hanamura, I., Wright, G., Xiao, W., et al. (2007). Frequent engagement of the classical and alternative NF-kappaB pathways by diverse genetic abnormalities in multiple myeloma. Cancer Cell 12, 115-130.
Ausubel, F. M. et al. (1995) and periodic supplements; Current Protocols in Molecular Biology, ch. 9, 13, and 16, John Wiley & Sons, New York, N.Y.
Bartkova, J., Horejsi, Z., Koed, K., Kramer, A., Tort, F., Zieger, K., Guldberg, P., Sehested, M., Nesland, J. M., Lukas, C., et al. (2005). DNA damage response as a candidate anti-cancer barrier in early human tumorigenesis. Nature 434, 864-870.
Baskaran, R., Wood, L. D., Whitaker, L. L., Canman, C. E., Morgan, S. E., Xu, Y., Barlow, C., Baltimore, D., Wynshaw-Boris, A., Kastan, M. B., et al. (1997). Ataxia telangiectasia mutant protein activates c-Abl tyrosine kinase in response to ionizing radiation. Nature 387, 516-519.
Basu, S., Totty, N. F., Irwin, M. S., Sudol, M., and Downward, J. (2003). Akt phosphorylates the Yes-associated protein, YAP, to induce interaction with 14-3-3 and attenuation of p73-mediated apoptosis. Mol Cell 11, 11-23.
Bertini, E., Oka, T., Sudol, M., Strano, S., and Blandino, G. (2009). YAP: at the crossroad between transformation and tumor suppression. Cell Cycle 8, 49-57.

(56) References Cited

OTHER PUBLICATIONS

Boehrer, S., Ades, L., Tajeddine, N., Hofmann, W. K., Kriener, S., Bug, G., Ottmann, O. G., Ruthardt, M., Galluzzi, L., Fouassier, C., et al. (2009). Suppression of the DNA damage response in acute myeloid leukemia versus myelodysplastic syndrome. Oncogene 28, 2205-2218.

Brown, L., and McCarthy, N. (1997). DNA repair. A sense-able response? Nature 387, 450-451.

Brummelkamp T R et al., A system for stable expression of short interfering RNAs in mammalian cells. Science 296: 550-553, 2002.

Carrasco, D. R., Tonon, G., Huang, Y., Zhang, Y., Sinha, R., Feng, B., Stewart, J. P., Zhan, F., Khatry, D., Protopopova, M., et al. (2006). High-resolution genomic profiles define distinct clinicopathogenetic subgroups of multiple myeloma patients. Cancer Cell 9, 313-325.

Cell Signaling ID #4912 http://www.cellsignal.com/products/4912.html.

Chapman, M. A, Lawrence, M. S., Keats, J. J., Cibulskis, K., Sougnez, C., Schinzel, A. C., Harview, C. L, Brunet, J. P., Ahmann, G. J., Adli, M., et al. (2011). Initial genome sequencing and analysis of multiple myeloma. Nature 471, 467-472.

Coffin et al., 1997, "retroviruses", Cold Spring Harbour Laboratory Press Eds: J M Coffin, S M Hughes, H E Varmus pp. 758-763.

Davis, M. I., Hunt, J. P., Herrgard, S., Ciceri, P., Wodicka, L. M., Pallares, G., Hocker, M., Treiber, D. K., and Zarrinkar, P. P. (2011). Comprehensive analysis of kinase inhibitor selectivity. Nature biotechnology 29, 1046-1051.

De Vos, J., Thykjaer, T., Tarte, K., Ensslen, M., Raynaud, P., Requirand, G., Pellet, F., Pantesco, V., Reme, T., Jourdan, M., et al. (2002). Comparison of gene expression profiling between malignant and normal plasma cells with oligonucleotide arrays. Oncogene 21, 6848-6857.

Dispenzieri, A., Gertz, M. A., Lacy, M. Q., Geyer, S. M., Greipp, P. R., Rajkumar, S. V., Kimlinger, T., Lust, J. A., Fonseca, R., Allred, J., et al. (2006). A phase II trial of imatinib in patients with refractory/relapsed myeloma. Leuk Lymphoma 47, 39-42.

Espanel X and Sudol M, Yes-associated Protein and p53-binding Protein-2 Interact through Their WW and SH3 Domains, Journal of Biochemical Chemistry, 2001, 276(17):14514-14523.

Gait M. J. (Editor), 1984, Oligonucleotide Synthesis: A Practical Approach, Irl Press.

GenBank Accession No. NM_001130145.
GenBank Accession No. NM_005157.4.
GenBank Accession No. NM_006106.4.
GenBank Accession No. NM_006281.3.
GenBank Accession No. NM_006282.2.
GenBank Accession No. NP_001123617.1.
GenBank Accession No. NP_005148.2.
GenBank Accession No. NP_006097.2.
GenBank Accession No. NP_006272.2.
GenBank Accession No. NP_006273.1.

Gorgoulis, V. G., Vassiliou, L. V., Karakaidos, P., Zacharatos, P., Kotsinas, A., Liloglou, T., Venere, M., Ditullio, R. A., Jr., Kastrinakis, N. G., Levy, B., et al. (2005). Activation of the DNA damage checkpoint and genomic instability in human precancerous lesions. Nature 434, 907-913.

Gou D et al Gene silencing in alveolar type II cells using cell-specific promoter in vitro and in vivo. Nucleic Acids Res 32: e134, 2004.

Gou D et al Gene silencing in mammalian cells by PCR-based short hairpin RNA. FEBS Lett 548: 113-118, 2003.

Halazonetis, T. D., Gorgoulis, V. G., and Bartek, J. (2008). An oncogene-induced DNA damage model for cancer development. Science 319, 1352-1355.

Hickson, I., Zhao, Y., Richardson, C. J., Green, S. J., Martin, N. M., On, A. I., Reaper, P. M., Jackson, S. P., Curtin, N. J. and Smith, G. C. (2004). Identification and characterization of a novel and specific inhibitor of the ataxia-telangiectasia mutated kinase ATM. Cancer Res 64, 9152-9159.

Hideshima, T., Mitsiades, C., Akiyama, M., Hayashi, T., Chauhan, D., Richardson, P., Schlossman, R., Podar, K., Munshi, N. C., Mitsiades, N., et al. (2003). Molecular mechanisms mediating antimyeloma activity of proteasome inhibitor PS-341. Blood 101, 1530-1534.

Kaelin, W. G., Jr. (2005). The concept of synthetic lethality in the context of anticancer therapy. Nat Rev Cancer 5, 689-698.

Keats, J. J., Fonseca, R., Chesi, M., Schop, R., Baker, A., Chng, W. J., Van Wier, S., Tiedemann, R., Shi, C. X., Sebag, M., et al. (2007). Promiscuous mutations activate the noncanonical NF-kappaB pathway in multiple myeloma. Cancer Cell 12, 131-144.

Kharbanda, S., Ren, R., Pandey, P., Shafman, T. D., Feller, S. M., Weichselbaum, R. R., and Kufe, D. W. (1995). Activation of the c-Abl tyrosine kinase in the stress response to DNA-damaging agents. Nature 376, 785-788.

Kyle R A et al. Clinical course and prognosis of smoldering (asymptomatic) multiple myeloma. N Engl J Med 2007; 356 (25):2582-2590.

Kyle R A et al. Multiple myeloma. N Engl J Med 2004; 351(18): 1860-1873.

Kyle R A et al. Prevalence of monoclonal gammopathy of undetermined significance. N Engl J Med 2006; 354 (13):1362-1369.

Lapi, E., Di Agostino, S., Donzelli, S., Gal, H., Domany, E., Rechavi, G., Pandolfi, P. P., Givol, D., Strano, S., Lu, X., et al. (2008). PML, YAP, and p73 are components of a proapoptotic autoregulatory feedback loop. Mol Cell 32, 803-814.

Lenz G R, Nash H M, Jindal S 2000 Chemical ligands, genomics and drug discovery. Drug Discov Today 5:145-156.

Levy, D., Adamovich, Y., Reuven, N., and Shaul, Y. (2007). The Yes-associated protein 1 stabilizes p73 by preventing Itch-mediated ubiquitination of p73. Cell Death Differ 14, 743-751.

Levy, D., Adamovich, Y., Reuven, N., and Shaul, Y. (2008). Yap 1 phosphorylation by c-Abl is a critical step in selective activation of proapoptotic genes in response to DNA damage. Mol Cell 29, 350-361.

Lilley and J. E. Dahlberg D. M. J., 1992, Methods of Enzymology: DNA Structure Part A: Synthesis and Physical Analysis of DNA Methods in Enzymology, Academic Press.

Melton D A et al., Efficient in vitro sythnesis of biologically active RNA and RNA hydribization probes from plasmids contining a bacteriophage SP6 promoter, Nucleic Acids Research, vol. 12, No. 18, p. 7035.

Palumbo, A., and Anderson, K. (2011). Multiple myeloma. N Engl J Med 364, 1046-1060.

Pan, D. (2010). The hippo signaling pathway in development and cancer. Dev Cell 19, 491-505.

Paul C P et al., Effective expression of small interfering RNA in human cells. Nat Biotechnol 20: 505-508, 2002.

\* cited by examiner

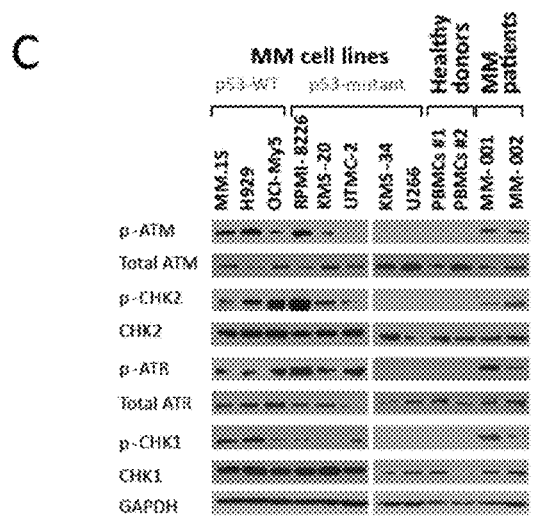
FIGURE 1C
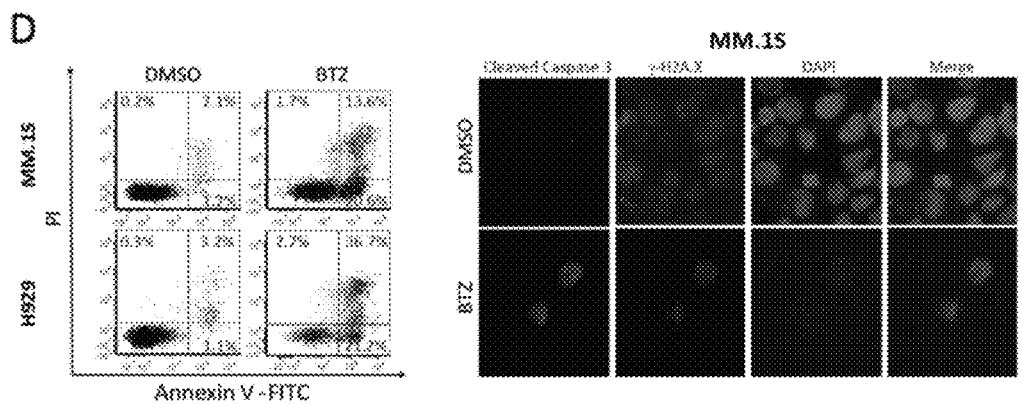
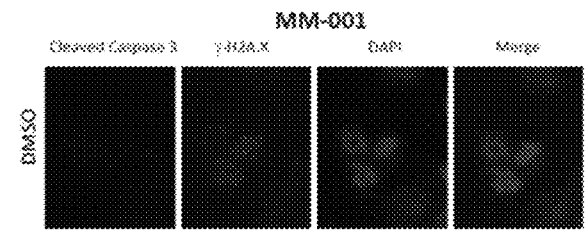
FIGURE 1D

A

γ-H2A.X

B

H929

B

RPMI-8226

>NM_001130145 Homo sapiens Yes-associated protein 1 (YAP1), transcript variant 1, Mrna:

```
GCCGCCGCCAGGGAAAAGAAAGGGAGGAAGGAAGGAACAAGAAAAGGAAATAAAGAGAAAGGGGA
GGCGGGGAAAGGCAACGAGCTGTCCGGCCTCCGTCAAGGGAGTTGGAGGGAAAAAGTTCTCAGGCGC
CGCAGGTCCGAGTGCCTCGCAGCCCCTCCCGAGGCGCAGCCGCCAGACCAGTGGAGCCGGGGCGCAG
GGCGGGGGCGGAGGCGCCGGGGCGGGGGATGCGGGGCCGCGGCGCAGCCCCCCGGCCCTGAGAGCG
AGGACAGCGCCGCCCGGCCCGCAGCCGTCGCCGCTTCTCCACCTCGGCCCGTGGAGCCGGGGCGTCCG
GGCGTAGCCCTCGCTCGCCTGGGTCAGGGGGTGCGCGTCGGGGGAGGCAGAAGCCATGGATCCCGGG
CAGCAGCCGCCGCCTCAACCGGCCCCCCAGGGCCAAGGGCAGCCGCCTTCGCAGCCCCCGCAGGGGC
AGGGCCCGCCGTCCGGACCCGGGCAACCGGCACCCGCGGCGACCCAGGCGGCGCCGCAGGCACCCCC
CGCCGGGCATCAGATCGTGCACGTCCGCGGGGACTCGGAGACCGACCTGGAGGCGCTCTTCAACGCCG
TCATGAACCCCAAGACGGCCAACGTGCCCCAGACCGTGCCCATGAGGCTCCGGAAGCTGCCCGACTCC
TTCTTCAAGCCGCCGGAGCCCAAATCCCACTCCCGACAGGCCAGTACTGATGCAGGCACTGCAGGAGC
CCTGACTCCACAGCATGTTCGAGCTCATTCCTCTCCAGCTTCTCTGCAGTTGGGAGCTGTTTCTCCTGG
GACACTGACCCCCACTGGAGTAGTCTCTGGCCCAGCAGCTACACCCACAGCTCAGCATCTTCGACAGT
CTTCTTTTGAGATACCTGATGATGTACCTCTGCCAGCAGGTTGGGAGATGGCAAAGACATCTTCTGGTC
AGAGATACTTCTTAAATCACATCGATCAGACAACAACATGGCAGGACCCCAGGAAGGCCATGCTGTCC
CAGATGAACGTCACAGCCCCCACCAGTCCACCAGTGCAGCAGAATATGATGAACTCGGCTTCAGGTCC
TCTTCCTGATGGATGGGAACAAGCCATGACTCAGGATGGAGAAATTTACTATATAAACCATAAGAACA
AGACCACCTCTTGGCTAGACCCAAGGCTTGACCCTCGTTTTGCCATGAACCAGAGAATCAGTCAGAGT
GCTCCAGTGAAACAGCCACCACCCCTGGCTCCCCAGAGCCCACAGGGAGGCGTCATGGGTGGCAGCA
ACTCCAACCAGCAGCAACAGATGCGACTGCAGCAACTGCAGATGGAGAAGGAGAGGCTGCGGCTGAA
ACAGCAAGAACTGCTTCGGCAGGCAATGCGGAATATCAATCCCAGCACAGCAAATTCTCCAAAATGTC
AGGAGTTAGCCCTGCGTAGCCAGTTACCAACACTGGAGCAGGATGGTGGGACTCAAAATCCAGTGTCT
TCTCCCGGGATGTCTCAGGAATTGAGAACAATGACGACCAATAGCTCAGATCCTTTCCTTAACAGTGG
CACCTATCACTCTCGAGATGAGAGTACAGACAGTGGACTAAGCATGAGCAGCTACAGTGTCCCTCGAA
CCCCAGATGACTTCCTGAACAGTGTGGATGAGATGGATACAGGTGATACTATCAACCAAAGCACCCTG
CCCTCACAGCAGAACCGTTTCCCAGACTACCTTGAAGCCATTCCTGGGACAAATGTGGACCTTGGAAC
ACTGGAAGGAGATGGAATGAACATAGAAGGAGAGGAGCTGATGCCAAGTCTGCAGGAAGCTTTGAGT
TCTGACATCCTTAATGACATGGAGTCTGTTTTGGCTGCCACCAAGCTAGATAAAGAAAGCTTTCTTACA
TGGTTATAGAGCCCTCAGGCAGACTGAATTCTAAATCTGTGAAGGATCTAAGGAGACACATGCACCGG
AAATTTCCATAAGCCAGTTGCAGTTTTCAGGCTAATACAGAAAAAGATGAACAAACGTCCAGCAAGAT
ACTTTAATCCTCTATTTTGCTCTTCCTTGTCCATTGCTGCTGTTAATGTATTGCTGACCTCTTTCACAGTT
GGCTCTAAAGAATCAAAAGAAAAAAACTTTTTATTTCTTTTGCTATTAAAACTACTGTTCATTTTGGGG
GCTGGGGGAAGTGAGCCTGTTTGGATGATGGATGCCATTCCTTTTGCCCAGTTAAATGTTCACCAATCA
TTTTAACTAAATACTCAGACTTAGAAGTCAGATGCTTCATGTCACAGCATTTAGTTTGTTCAACAGTTG
TTTCTTCAGCTTCCTTTGTCCAGTGGAAAAACATGATTTACTGGTCTGACAAGCCAAAAATGTTATATC
TGATATTAAATACTTAATGCTGATTTGAAGAGATAGCTGAAACCAAGGCTGAAGACTGTTTTACTTTCA
GTATTTTCTTTTCCTCCTAGTGCTATCATTAGTCACATAATGACCTTGATTTTATTTTAGGAGCTTATAA
GGCATGAGACAATTTCCATATAAATATATTAATTATTGCCACATACTCTAATATAGATTTTGGTGGATA
ATTTTGTGGGTGTGCATTTTGTTCTGTTTGTTGGGTTTTTGTTTTTTTGTTTTGGCAGGGTCGGTGG
GGGGGTTGGTTGGTTGGTTGGTTTTGTCGGAACCTAGGCAAATGACCATATTAGTGAATCTGTTAATAG
TTGTAGCTTGGGATGGTTATTGTAGTTGTTTTGGTAAAATCTTCATTTCCTGGTTTTTTTTACCACCTTAT
TTAAATCTCGATTATCTGCTCTCTCTTTTATATACATACACACACCCAAACATAACATTTATAATAGTGT
GGTAGTGGAATGTATCCTTTTTTAGGTTTCCCTGCTTTCCAGTTAATTTTTAAAATGGTAGCGCTTTGTA
TGCATTTAGAATACATGACTAGTAGTTTATATTTCACTGGTAGTTTAAATCTGGTTGGGGCAGTCTGCA
GATGTTTGAAGTAGTTTAGTGTTCTAGAAAGAGCTATTACTGTGGATAGTGCCTAGGGGAGTGCTCCA
CGCCCTCTGGGCATACGGTAGATATTATCTGATGAATTGGAAAGGAGCAAACCAGAAATGGCTTTATT
TTCTCCCTTGGACTAATTTTTAAGTCTCGATTGGAATTCAGTGAGTAGGTTCATAATGTGCATGACAGA
AATAAGCTTTATAGTGGTTTACCTTCATTTAGCTTTGGAAGTTTTCTTTGCCTTAGTTTTGGAAGTAAAT
TCTAGTTTGTAGTTCTCATTTGTAATGAACACATTAACGACTAGATTAAAATATTGCCTTCAAGATTGT
TCTTACTTACAAGACTTGCTCCTACTTCTATGCTGAAAATTGACCCTGGATAGAATACTATAAGGTTTT
```

Figure 8A (continued)
GAGTTAGCTGGAAAAGTGATCAGATTAATAAATGTATATTGGTAGTTGAATTTAGCAAAGAAATAGAG
ATAATCATGATTATACCTTTATTTTTACAGGAAGAGATGATGTAACTAGAGTATGTGTCTACAGGAGTA
ATAATGGTTTCCAAAGAGTATTTTTTAAAGGAACAAAACGAGCATGAATTAACTCTTCAATATAAGCT
ATGAAGTAATAGTTGGTTGTGAATTAAAGTGGCACCAGCTAGCACCTCTGTGTTTTAAGGGTCTTTCAA
TGTTTCTAGAATAAGCCCTTATTTTCAAGGGTTCATAACAGGCATAAAATCTCTTCTCCTGGCAAAAGC
TGCTATGAAAAGCCTCAGCTTGGGAAGATAGATTTTTTTCCCCCCAATTACAAAATCTAAGTATTTTGG
CCCTTCAATTTGGAGGAGGGCAAAAGTTGGAAGTAAGAAGTTTTATTTTAAGTACTTTCAGTGCTCAA
AAAAATGCAATCACTGTGTTGTATATAATAGTTCATAGGTTGATCACTCATAATAATTGACTCTAAGGC
TTTTATTAAGAAAACAGCAGAAAGATTAAATCTTGAATTAAGTCTGGGGGGAAATGGCCACTGCAGAT
GGAGTTTTAGAGTAGTAATGAAATTCTACCTAGAATGCAAAATTGGGTATATGAATTACATAGCATGT
TGTTGGGATTTTTTTTAATGTGCAGAAGATCAAAGCTACTTGGAAGGAGTGCCTATAATTTGCCAGTAG
CCACAGATTAAGATTATATCTTATATATCAGCAGATTAGCTTTAGCTTAGGGGGAGGGTGGGAAAGTT
TGGGGGGGGGGGTTGTGAAGATTTAGGGGGACCTTGATAGAGAACTTTATAAACTTCTTTCTCTTTAATA
AAGACTTGTCTTACACCGTGCTGCCATTAAAGGCAGCTGTTCTAGAGTTTCAGTCACCTAAGTACACCC
ACAAAACAATATGAATATGGAGATCTTCCTTTACCCCTCAACTTTAATTTGCCCAGTTATACCTCAGTG
TTGTAGCAGTACTGTGATACCTGGCACAGTGCTTTGATCTTACGATGCCCTCTGTACTGACCTGAAGGA
GACCTAAGAGTCCTTTCCCTTTTTGAGTTTGAATCATAGCCTTGATGTGGTCTCTTGTTTTATGTCCTTG
TTCCTAATGTAAAAGTGCTTAACTGCTTCTTGGTTGTATTGGGTAGCATTGGGATAAGATTTTAACTGG
GTATTCTTGAATTGCTTTTACAATAAACCAATTTTATAATCTTTAAATTTATCAACTTTTTACATTTGTG
TTATTTTCAGTCAGGGCTTCTTAGATCTACTTATGGTTGATGGAGCACATTGATTTGGAGTTTCAGATCT
TCCAAAGCACTATTTGTTGTAATAACTTTTCTAAATGTAGTGCCTTTAAAGGAAAAATGAACACAGGG
AAGTGACTTTGCTACAAATAATGTTGCTGTGTTAAGTATTCATATTAAATACATGCCTTCTATATGGAA
CATGGCAGAAAGACTGAAAAATAACAGTAATTAATTGTGTAATTCAGAATTCATACCAATCAGTGTTG
AAACTCAAACATTGCAAAAGTGGGTGGCAATATTCAGTGCTTAACACTTTTCTAGCGTTGGTACATCTG
AGAAATGAGTGCTCAGGTGGATTTTATCCTCGCAAGCATGTTGTTATAAGAATTGTGGGTGTGCCTATC
ATAACAATTGTTTTCTGTATCTTGAAAAAGTATTCTCCACATTTTAAATGTTTATATTAGAGAATTCTT
TAATGCACACTTGTCAAATATATATATAGTACCAATGTTACCTTTTATTTTTGTTTTAGATGTAAG
AGCATGCTCATATGTTAGGTACTTACATAAATTGTTACATTATTTTTTCTTATGTAATACCTTTTTGTTT
GTTTATGTGGTTCAAATATATTCTTTCCTTAAACTCTTAAAAAAAAAA

Figure 8B

>NP_001123617.1| yorkie homolog isoform 1 [Homo sapiens]
MDPGQQPPPQPAPQGQGQPPSQPPQGQGPPSGPGQPAPAATQAAPQAPPAGHQIVHVRGDSETDLEALFNA
VMNPKTANVPQTVPMRLRKLPDSFFKPPEPKSHSRQASTDAGTAGALTPQHVRAHSSPASLQLGAVSPGTL
TPTGVVSGPAATPTAQHLRQSSFEIPDDVPLPAGWEMAKTSSGQRYFLNHIDQTTTWQDPRKAMLSQMNV
TAPTSPPVQQNMMNSASGPLPDGWEQAMTQDGEIYYINHKNKTTSWLDPRLDPRFAMNQRISQSAPVKQP
PPLAPQSPQGGVMGGSNSNQQQQMRLQQLQMEKERLRLKQQELLRQAMRNINPSTANSPKCQELALRSQL
PTLEQDGGTQNPVSSPGMSQELRTMTTNSSDPFLNSGTYHSRDESTDSGLSMSSYSVPRTPDDFLNSVDEM
DTGDTINQSTLPSQQNRFPDYLEAIPGTNVDLGTLEGDGMNIEGEELMPSLQEALSSDILNDMESVLAATKL
DKESFLTWL

Figure 8C

>NM_006106.4 Homo sapiens Yes-associated protein 1 (YAP1), transcript variant 2, mRNA
GCCGCCGCCAGGGAAAGAAAGGGAGGAAGGAAGGAACAAGAAAAGGAAATAAAGAGAAAGGGGA
GGCGGGGAAAGGCAACGAGCTGTCCGGCCTCCGTCAAGGGAGTTGGAGGGAAAAAGTTCTCAGGCGC
CGCAGGTCCGAGTGCCTCGCAGCCCCTCCCGAGGCGCAGCCGCCAGACCAGTGGAGCCGGGGCGCAG
GGCGGGGGCGGAGGCGCCGGGGCGGGGGATGCGGGGCCGCGGCGCAGCCCCCGGCCCTGAGAGCG
AGGACAGCGCCGCCCGGCCCGCAGCCGTCGCCGCTTCTCCACCTCGGCCCGTGGAGCCGGGGCGTCCG
GGCGTAGCCCTCGCTCGCCTGGGTCAGGGGTGCGCGTCGGGGGAGGCAGAAGCCATGGATCCCGGG
CAGCAGCCGCCGCCTCAACCGGCCCCCAGGGCCAAGGGCAGCCGCCTTCGCAGCCCCGCAGGGGC
AGGGCCCGCCGTCCGGACCCGGGCAACCGGCACCCGCGGCGACCCAGGCGGCGCCGCAGGCACCCCC

Figure 8C (Continued)
CGCCGGGCATCAGATCGTGCACGTCCGCGGGGACTCGGAGACCGACCTGGAGGCGCTCTTCAACGCCG
TCATGAACCCCAAGACGGCCAACGTGCCCCAGACCGTGCCCATGAGGCTCCGGAAGCTGCCCGACTCC
TTCTTCAAGCCGCCGGAGCCCAAATCCCACTCCCGACAGGCCAGTACTGATGCAGGCACTGCAGGAGC
CCTGACTCCACAGCATGTTCGAGCTCATTCCTCTCCAGCTTCTCTGCAGTTGGGAGCTGTTTCTCCTGG
GACACTGACCCCCACTGGAGTAGTCTCTGGCCCAGCAGCTACACCCACAGCTCAGCATCTTCGACAGT
CTTCTTTTGAGATACCTGATGATGTACCTCTGCCAGCAGGTTGGGAGATGGCAAAGACATCTTCTGGTC
AGAGATACTTCTTAAATCACATCGATCAGACAACAACATGGCAGGACCCCAGGAAGGCCATGCTGTCC
CAGATGAACGTCACAGCCCCACCAGTCCACCAGTGCAGCAGAATATGATGAACTCGGCTTCAGCCAT
GAACCAGAGAATCAGTCAGAGTGCTCCAGTGAAACAGCCACCACCCCTGGCTCCCCAGAGCCCACAG
GGAGGCGTCATGGGTGGCAGCAACTCCAACCAGCAGCAACAGATGCGACTGCAGCAACTGCAGATGG
AGAAGGAGAGGCTGCGGCTGAAACAGCAAGAACTGCTTCGGCAGGAGTTAGCCCTGCGTAGCCAGTT
ACCAACACTGGAGCAGGATGGTGGGACTCAAAATCCAGTGTCTTCTCCCGGGATGTCTCAGGAATTGA
GAACAATGACGACCAATAGCTCAGATCCTTTCCTTAACAGTGGCACCTATCACTCTCGAGATGAGAGT
ACAGACAGTGGACTAAGCATGAGCAGCTACAGTGTCCCTCGAACCCCAGATGACTTCCTGAACAGTGT
GGATGAGATGGATACAGGTGATACTATCAACCAAAGCACCCTGCCCTCACAGCAGAACCGTTTCCCAG
ACTACCTTGAAGCCATTCCTGGGACAAATGTGGACCTTGGAACACTGGAAGGAGATGGAATGAACAT
AGAAGGAGAGGAGCTGATGCCAAGTCTGCAGGAAGCTTTGAGTTCTGACATCCTTAATGACATGGAGT
CTGTTTTGGCTGCCACCAAGCTAGATAAAGAAAGCTTTCTTACATGGTTATAGAGCCCTCAGGCAGAC
TGAATTCTAAATCTGTGAAGGATCTAAGGAGACACATGCACCGGAAATTTCCATAAGCCAGTTGCAGT
TTTCAGGCTAATACAGAAAAAGATGAACAAACGTCCAGCAAGATACTTTAATCCTCTATTTTGCTCTTC
CTTGTCCATTGCTGCTGTTAATGTATTGCTGACCTCTTTCACAGTTGGCTCTAAAGAATCAAAAGAAAA
AACTTTTTATTTCTTTTGCTATTAAAACTACTGTTCATTTTGGGGGCTGGGGGAAGTGAGCCTGTTTG
GATGATGGATGCCATTCCTTTTGCCCAGTTAAATGTTCACCAATCATTTTAACTAAATACTCAGACTTA
GAAGTCAGATGCTTCATGTCACAGCATTTAGTTGTTCAACAGTTGTTTCTTCAGCTTCCTTTGTCCAGT
GGAAAAACATGATTTACTGGTCTGACAAGCCAAAAATGTTATATCTGATATTAAATACTTAATGCTGA
TTTGAAGAGATAGCTGAAACCAAGGCTGAAGACTGTTTTACTTTCAGTATTTTCTTTTCCTCCTAGTGC
TATCATTAGTCACATAATGACCTTGATTTTATTTTAGGAGCTTATAAGGCATGAGACAATTTCCATATA
AATATATTAATTATTGCCACATACTCTAATATAGATTTTGGTGGATAATTTTGTGGGTGTGCATTTTGTT
CTGTTTTGTTGGGTTTTTTGTTTTTTTGTTTTTGGCAGGGTCGGTGGGGGGTTGGTTGGTTGGTTGGT
TTTGTCGGAACCTAGGCAAATGACCATATTAGTGAATCTGTTAATAGTTGTAGCTTGGGATGGTTATTG
TAGTTGTTTTGGTAAAATCTTCATTTCCTGGTTTTTTTTACCACCTTATTTAAATCTCGATTATCTGCTCT
CTCTTTTATATACATACACACACCCAAACATAACATTTATAATAGTGTGGTAGTGGAATGTATCCTTTT
TTAGGTTTCCCTGCTTTCCAGTTAATTTTTAAAATGGTAGCGCTTTGTATGCATTTAGAATACATGACTA
GTAGTTTATATTTCACTGGTAGTTTAAATCTGGTTGGGGCAGTCTGCAGATGTTTGAAGTAGTTTAGTG
TTCTAGAAAGAGCTATTACTGTGGATAGTGCCTAGGGGAGTGCTCCACGCCCTCTGGGCATACGGTAG
ATATTATCTGATGAATTGGAAAGGAGCAAACCAGAAATGGCTTTATTTTCTCCCTTGGACTAATTTTTA
AGTCTCGATTGGAATTCAGTGAGTAGGTTCATAATGTGCATGACAGAAATAAGCTTTATAGTGGTTTA
CCTTCATTTAGCTTTGGAAGTTTTCTTTGCCTTAGTTTTGGAAGTAAATTCTAGTTTGTAGTTCTCATTT
GTAATGAACACATTAACGACTAGATTAAAATATTGCCTTCAAGATTGTTCTTACTTACAAGACTTGCTC
CTACTTCTATGCTGAAAATTGACCCTGGATAGAATACTATAAGGTTTTGAGTTAGCTGGAAAAGTGAT
CAGATTAATAAATGTATATTGGTAGTTGAATTTAGCAAAGAAATAGAGATAATCATGATTATACCTTT
ATTTTTACAGGAAGAGATGATGTAACTAGAGTATGTGTCTACAGGAGTAATAATGGTTTCCAAAGAGT
ATTTTTTAAAGGAACAAAACGAGCATGAATTAACTCTTCAATATAAGCTATGAAGTAATAGTTGGTTG
TGAATTAAAGTGGCACCAGCTAGCACCTCTGTGTTTAAGGGTCTTTCAATGTTTCTAGAATAAGCCCT
TATTTTCAAGGGTTCATAACAGGCATAAAATCTCTTCTCCTGGCAAAAGCTGCTATGAAAAGCCTCAG
CTTGGGAAGATAGATTTTTTTCCCCCCAATTACAAAATCTAAGTATTTTGGCCCTTCAATTTGGAGGAG
GGCAAAAGTTGGAAGTAAGAAGTTTTATTTTAAGTACTTTCAGTGCTCAAAAAAATGCAATCACTGTG
TTGTATATAATAGTTCATAGGTTGATCACTCATAATAATTGACTCTAAGGCTTTTATTAAGAAAACAGC
AGAAAGATTAAATCTTGAATTAAGTCTGGGGGGAAATGGCCACTGCAGATGGAGTTTTAGAGTAGTAA
TGAAATTCTACCTAGAATGCAAAATTGGGTATATGAATTACATAGCATGTTGTTGGGATTTTTTTAAT
GTGCAGAAGATCAAAGCTACTTGGAAGGAGTGCCTATAATTTGCCAGTAGCCACAGATTAAGATTATA
TCTTATATATCAGCAGATTAGCTTTAGCTTAGGGGGAGGGTGGGAAAGTTTGGGGGGGGGTTGTGAA
GATTTAGGGGGACCTTGATAGAGAACTTTATAAACTTCTTTCTCTTTAATAAAGACTTGTCTTACACCG
TGCTGCCATTAAAGGCAGCTGTTCTAGAGTTTCAGTCACCTAAGTACACCCACAAAACAATATGAATA
TGGAGATCTTCCTTTACCCCTCAACTTTAATTTGCCCAGTTATACCTCAGTGTTGTAGCAGTACTGTGAT

Figure 8C (Continued)
ACCTGGCACAGTGCTTTGATCTTACGATGCCCTCTGTACTGACCTGAAGGAGACCTAAGAGTCCTTTCC
CTTTTTGAGTTTGAATCATAGCCTTGATGTGGTCTCTTGTTTTATGTCCTTGTTCCTAATGTAAAAGTGC
TTAACTGCTTCTTGGTTGTATTGGGTAGCATTGGGATAAGATTTTAACTGGGTATTCTTGAATTGCTTTT
ACAATAAACCAATTTTATAATCTTTAAATTTATCAACTTTTTACATTTGTGTTATTTTCAGTCAGGGCTT
CTTAGATCTACTTATGGTTGATGGAGCACATTGATTTGGAGTTTCAGATCTTCCAAAGCACTATTTGTT
GTAATAACTTTTCTAAATGTAGTGCCTTTAAAGGAAAAATGAACACAGGGAAGTGACTTTGCTACAAA
TAATGTTGCTGTGTTAAGTATTCATATTAAATACATGCCTTCTATATGGAACATGGCAGAAAGACTGAA
AAATAACAGTAATTAATTGTGTAATTCAGAATTCATACCAATCAGTGTTGAAACTCAAACATTGCAAA
AGTGGGTGGCAATATTCAGTGCTTAACACTTTTCTAGCGTTGGTACATCTGAGAAATGAGTGCTCAGGT
GGATTTTATCCTCGCAAGCATGTTGTTATAAGAATTGTGGGTGTGCCTATCATAACAATTGTTTTCTGT
ATCTTGAAAAAGTATTCTCCACATTTTAAATGTTTTATATTAGAGAATTCTTTAATGCACACTTGTCAA
ATATATATATATAGTACCAATGTTACCTTTTTATTTTTTGTTTTAGATGTAAGAGCATGCTCATATGTTA
GGTACTTACATAAATTGTTACATTATTTTTTCTTATGTAATACCTTTTTGTTTGTTTATGTGGTTCAAATA
TATTCTTTCCTTAAACTCTTAAAAAAAAAA

Figure 8D

>NP_006097.2| yorkie homolog isoform 2 [Homo sapiens]
MDPGQQPPPQPAPQGQGQPPSQPPQGQGPPSGPGQPAPAATQAAPQAPPAGHQIVHVRGDSETDLEALFNA
VMNPKTANVPQTVPMRLRKLPDSFFKPPEPKSHSRQASTDAGTAGALTPQHVRAHSSPASLQLGAVSPGTL
TPTGVVSGPAATPTAQHLRQSSFEIPDDVPLPAGWEMAKTSSGQRYFLNHIDQTTTWQDPRKAMLSQMNV
TAPTSPPVQQNMMNSASAMNQRISQSAPVKQPPPLAPQSPQGGVMGGSNSNQQQQMRLQQLQMEKERLR
LKQQELLRQELALRSQLPTLEQDGGTQNPVSSPGMSQELRTMTTNSSDPFLNSGTYHSRDESTDSGLSMSSS
VPRTPDDFLNSVDEMDTGDTINQSTLPSQQNRFPDYLEAIPGTNVDLGTLEGDGMNIEGEELMPSLQEALSS
DILNDMESVLAATKLDKESFLTWL

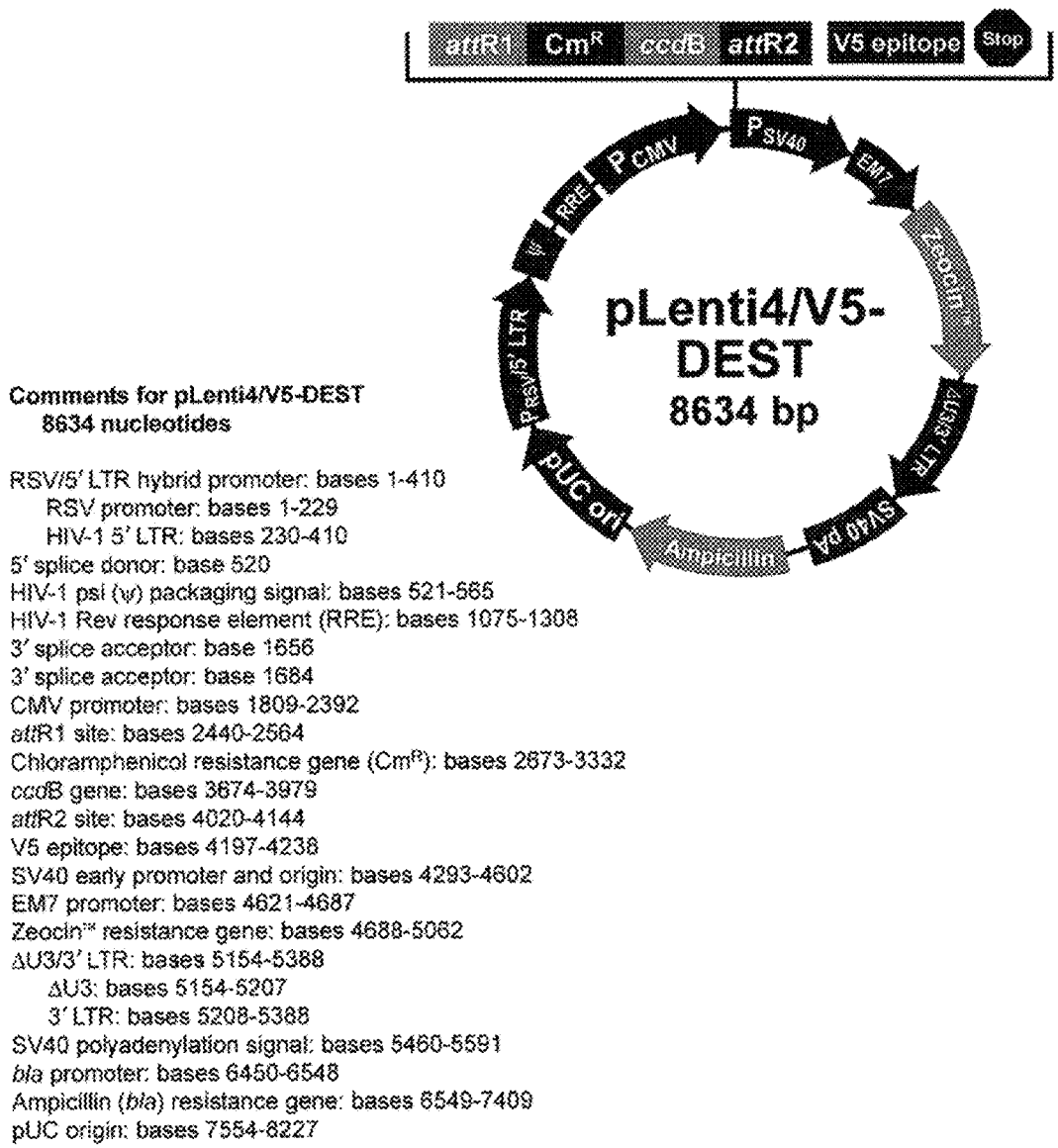

Comments for pLenti4/V5-DEST
8634 nucleotides

RSV/5'LTR hybrid promoter: bases 1-410
    RSV promoter: bases 1-229
    HIV-1 5' LTR: bases 230-410
5' splice donor: base 520
HIV-1 psi (ψ) packaging signal: bases 521-565
HIV-1 Rev response element (RRE): bases 1075-1308
3' splice acceptor: base 1656
3' splice acceptor: base 1684
CMV promoter: bases 1809-2392
attR1 site: bases 2440-2564
Chloramphenicol resistance gene ($Cm^R$): bases 2873-3332
ccdB gene: bases 3674-3979
attR2 site: bases 4020-4144
V5 epitope: bases 4197-4238
SV40 early promoter and origin: bases 4293-4602
EM7 promoter: bases 4621-4687
Zeocin™ resistance gene: bases 4688-5062
ΔU3/3' LTR: bases 5154-5388
    ΔU3: bases 5154-5207
    3' LTR: bases 5208-5388
SV40 polyadenylation signal: bases 5460-5591
bla promoter: bases 6450-6548
Ampicillin (bla) resistance gene: bases 6549-7409
pUC origin: bases 7554-8227

>NM_006282.2| Homo sapiens serine/threonine kinase 4 (STK4), mRNA
GCGGAAGTGTGGGAGGGTCTGCGGGGCGGGCTCAGGAGGTCCGCGGGAGGATGGAGCAGTGAGCGG
GTCTGGGCGGCTGCTGGCAGCGCCATGGAGACGGTACAGCTGAGGAACCCGCCGCGCCGGCAGCTGA
AAAAGTTGGATGAAGATAGTTTAACCAAACAACCAGAAGAAGTATTTGATGTCTTAGAGAAACTTGG
AGAAGGGTCCTATGGCAGCGTATACAAAGCTATTCATAAAGAGACCGGCCAGATTGTTGCTATTAAGC
AAGTTCCTGTGGAATCAGACCTCCAGGAGATAATCAAAGAAATCTCTATAATGCAGCAATGTGACAGC
CCTCATGTAGTCAAATATTATGGCAGTTATTTTAAGAACACAGACTTATGGATCGTTATGGAGTACTGT
GGGGCTGGTTCTGTATCTGATATCATTCGATTACGAAATAAAACGTTAACAGAAGATGAAATAGCTAC
AATATTACAATCAACTCTTAAGGGACTTGAATACCTTCATTTTATGAGAAAAATACACCGAGATATCA
AGGCAGGAAATATTTTGCTAAATACAGAAGGACATGCAAAACTTGCAGATTTTGGGGTAGCAGGTCA
ACTTACAGATACCATGGCCAAGCGGAATACAGTGATAGGAACACCATTTTGGATGGCTCCAGAAGTGA
TTCAGGAAATTGGATACAACTGTGTAGCAGACATCTGGTCCCTGGGAATAACTGCCATAGAAATGGCT
GAAGGAAAGCCCCCCTTATGCTGATATCCATCCAATGAGGGCAATCTTCATGATTCCTACAAATCCTCCT
CCCACATTCCGAAAACCAGAGCTATGGTCAGATAACTTTACAGATTTTGTGAAACAGTGTCTTGTAAA
GAGCCCTGAGCAGAGGGCCACAGCCACTCAGCTCCTGCAGCACCCATTTGTCAGGAGTGCCAAAGGA
GTGTCAATACTGCGAGACTTAATTAATGAAGCCATGGATGTGAAACTGAAACGCCAGGAATCCCAGCA
GCGGGAAGTGGACCAGGACGATGAAGAAAACTCAGAAGAGGATGAAATGGATTCTGGCACGATGGTT
CGAGCAGTGGGTGATGAGATGGGCACTGTCCGAGTAGCCAGCACCATGACTGATGGAGCCAATACTA
TGATTGAGCACGATGACACGTTGCCATCACAACTGGGCACCATGGTGATCAATGCAGAGGATGAGGA
AGAGGAAGGAACTATGAAAAGAAGGGATGAGACCATGCAGCCTGCGAAACCATCCTTTCTTGAATAT
TTTGAACAAAAAGAAAAGGAAAACCAGATCAACAGCTTTGGCAAGAGTGTACCTGGTCCACTGAAAA
ATTCTTCAGATTGGAAAATACCACAGGATGGAGACTACGAGTTTCTTAAGAGTTGGACAGTGGAGGAC
CTTCAGAAGAGGCTCTTGGCCCTGGACCCCATGATGGAGCAGGAGATTGAAGAGATCCGGCAGAAGT
ACCAGTCCAAGCGGCAGCCCATCCTGGATGCCATAGAGGCTAAGAAGAGACGGCAACAAAACTTCTG
AGCAAGGCCAGGCTGTGAGGGCCCCAGCTCCACCCAGGCTTTGGGTGAATTCTGGATGGCTTGCCTCA
TGTTTGTTAGCCAGCACTTCTGCTCTGTCGTCTCCACAGCACCTTTGTGAACTCAGGAATGTGCGCC
AGTGGGAAGGGCTCTCTTGACAGTCAGCGTGCCATCTTGATGTGTGTATGTACATTGGTCAGGTATATT

Figure 9A (Continued)
ATCTCAAAGGATTTATATTGGCGCTTTTAACTCAGAGTTTTAAACCCCAGGAACAGAGACTCCTAGTTG
AGTGATAGCTGGGAAAGTTTTACATTGTCTGTTTTCTTCTCCCAATAGCTTTCAATTGTTCTTTCTGGA
AGACTTTTAAAAAAATATAAATATGCATATATATATATAAATTATAAATAGATTCCCCACGCAGTGTG
GTGGCATCTCTGTACAGGTACAGTTTTAAACGGTTTGCCTCTTTTCTGTAAGATTATGGTACTGTGGAA
CATGAGGGCAGAGGACACCGGGAGGCTGTTAGGGGGTCACTGAATCCCAGGAGCCAACCTCCCCCTTT
GCAGGGCTGCATTTAAAAATTAGGTTTGGGACAGTTCTTGTACCGTGGTTTCAGCCTTGTGTGGTCATC
ACTGGCTTCTGGAGCTATTGGTGATGTCCAAGGGAAAGCTTTGAGAGTTTATGTTTACTCTTTGAGTCC
CAGGAGAAGCCTGGCACCCTCTTTGCAAATTGGCCTTTGCTCTTTCAATGCCTTTCATCCATCTCCACT
CTCTCAACTGCCTAAAGTCACAGCACAGATACTGCCCAGTGCCTTAAGAGGAGACATGATCTCTACCA
GGGACTCTCAGCAAACACGGGACTGTGTTCAGTCCACAAAGGAAAAGCGTTTTGAAGCTCTCATTGT
TCATGTAAAAATCATACACGTGGCATGTTGCTCCACATTCCTTACACACAGGGGTAGAGGGGATTGCT
TTTGTGACCCACGTTCAAATATGTGACTGTTTTCTTTTCTCTTTTACTGCTAAGCAGCCTGGAAAGGATA
AATGAATATTAGACTAAGATTTGTTTTCCAGGAGGCTCAATCTGAACACACAGAATGTCAGAGCTGGA
AGGGACTATAGAGATCATCTGATCTGATCCTCTTGTACGGATGATCGCAAAACTGAGGTGTAGAGAGG
GGAATGGCCAAAATCACAAAGCAAGTTAGCGTTAAGAGCTGAGACTAGAATTCAGGGTCCTCACTCCC
AGGCCACCGAACCATGCAGCCCCTTCTTTGGGGAAGAGACCTGTGTCAGTCTTGGTTAATTGTTCCA
GGGAACCTTGCTAACAGAAACTTGCTCTTGCCTTGGCTCTTCAGTGATGACCTGGCTGTAAAGAGATT
CCCTGGACGAGCCAGATCATTCAGTTTCAGCGAGTCCTTGAGCTCCACAACATCTACCAGATATAGCA
GACAAGCACCCATGGAGGCAGGTTTCGGGCCTGAAGCAGATCAGAGGGCTTTGCAAAAGACAGCATA
GAGCCATCTTCCTGCAACTTTACCTCTTTCCCTCAGATGGGGAGCCATGACTGGGTTGCACCTCAGGAT
ACTGTAATTTGACTCCATAATTGCTTTTGCTCCTGAAACCTGGGAATCAATGGAAAGGCAGGGAATGT
GCCTCTTCTGTGGCCAGATTCTGTTATTTGCAATTAAAGCAAGTTTTTAAAAAATGCAAGAGGCAGTTG
TTAGTCTTCAGGGCTTGGCAACTGAAATAGCTATGTGGCGGATACGGAAAACAGAGGACAATTTGAGG
ATCTTGCTGGAATAATAAATGACAGCTACCATTTGTTGAGCACCTATTATATATCAGGCACTGAGCTGG
GTAGGCTCTAAACTTCACAATAACCCTGTGACTTAACTACTTTATCTCCATTTTGTAGTTGAAGAAATA
AGTTCAGAGAGAAAGATTCCTTCCCAAGGTCATGCAGCTAGTAAATGATAGAATCAGGATTCATAGCA
TCACTATAGGGGGTCAATATTTACACAAAAAAGGAAAGTCACAAGCCTGTTTAAAATGAAGTGACCAC
CTTTTCTTGCATAGACTAAATAACTCGAACTGGCATTTTTAGGTTGGAAAGACAGCTGAATTAGTAGTT
AAGTCTGATAGCCAAGTAAGTTTTAAAAACCAAAGCATCCAGGATGCACACCCCTGCACCATTTGCTG
TGCGAATTAATAGTTCTGTCTCTCTCTCTCTTTCTTTTTTCTTTTATTCTTTGAGATGGATTTTCGCTCTT
GTCGCCCAGGCTGGAGTACAATGGCACGATCTTGGCTCACTGCAACCTCCGCCTCCCGGGTTCAAGCG
ATTCTTCTGCTGGGATTACAGCATATGCCACCATGCCCAGATTATTTTTTGTATTTGTAGTAGAGACG
GGGTTTCACCATGTCAGTCAGGCTGGTCTTGAACTCCTGACCTCAGGTGATCCACCCGCCTCAGCCTCC
CACACTGCTGGGATTACAGGCATGAGCCACCGCTCCTGGCCTCTCTTTCTTTTTTAAACAAAGAACTTT
GCACTTGGCCAGAGAGGAGGAGAAAGCCCATTTTCTCCCTTCCTAAGCTAGATCCAAATAAAAGAAAG
TTCAGTTTTCCCCCATAACTATTCTTGGGTCATGAACTTTGATCTGGAGTTTGTTTTGTTTCAGGAATGT
GTGCACCCAGCTTGCTGATCCAACAAAGTCTATTGCTTACCAGTCTAGCTTGATGAAGCCTTTTGGCCA
GAAGTCAATTTGTTTTGGATCAGAGAAATTTCCTGACAAGGTATATTTGTTTTCTAGTGACAGAAAGGC
AAAGGAACAAGTCCTAGTTGTTGTTGTTGTTGTTGAATACTAAATTTAAGATATGTCAGCTTGCTTTCA
ATGAGCCTTGGGCTTCTGTTATTGCTTGAGCATTTGGAACTCGAGCTTCCAGAGAAATTTGAGGTCCTC
GCTTGTTCTCTGCCTTCAAGAAACAATGACCTGATTCTGTCTTTAAAAAAAAAAATCTCAGAATTCTTT
TTTTGTTTGTGTTTTTTTTTTTTTGAGACAGAGTCTCACTCTGTTGCCCAGGCTGGAGTGCAGTGGCG
CCATCTCGGCTCACTGCAACCTCCGCCTCCCAGGTTCAAGCAATTCTCCTGCCTCAGCCTCCCAGGTAG
CTGCCACTACAGGTGCTGCACCACCACGCCCGGCTAATTTTTGTATTTTTAGTAGAGACAGGGTTTCAC
CATATTAGCCAGGTGGGTCTTGAACTCCTGACCTTGTGATCCACCCGCCTCGGCCTCCCAAAGTGCTGG
GATTACAGGCGTGAGCCACCTTGCCTGGCCAAAAATCTCAGAATTCTTTAAGACTGTTTTAATTGCTCC
ATCAGTAATTTTGAAGCACTTTCCTTTTTTTTTTTTTCCCCTTTTGTCCCTTTCCCCAAGCCACCAAT
TGGATGGATGAATGTTTGACGGGGAAGAGGAAGGGTAGGAGGATGCATGGATGAGTGGATGAGTGGA
TCGATGGATGTATTGATAAATAGATAGAACCAGTCATCTGAAGCAACTTAAGAATTGTAGCCTTGACT
CCTTGAGACTGTAGATTTCGATCCAGGAAACATTTATTTAGCACCTGCCAGATGCCAGAAATTTATACC
ATTTAAAACTCAGTAAGTCTTTTAAATATCAGGAAGGAGAGAAGCGACATCATGATACATCCTATGGG
TATTAAAAAGCCAATAGAATATTATGAATAATTTTATGCTAATAAATTTAACAACTTCAACATCATAA
ACAAATTCCTTGAAAAATAAAAAGTACCAAAATTCATTCAAGAAGAAATAGATACCAGCCTGAGCAA
CATGGCAAAATCCCATCTCTACAAAACATCAAAAAAAAAAAAAATTAGTCGGGCATGGTGGTGCACA
CCTGTAATCCCAGCTTGTCAGGAGGCTGAAGTGGGAGGATCACCTGAGCCCAGGGAGGGTCAAGGATG

Figure 9A (Continued)

CAGTGAGCCATGGTCTCACCACTGCACTCTAGCCTGGGTGACAGAATGAGACCCCGTCTCAAAAAAAA
AGAAGAAGTAGATAATCTGAATAGCCCTATATCTATAGAAACTTAATAGTGCTGGGAGATATAGGTAT
TATTATCCTCATTTTACAGATGTGAAAATTGAGGCTCAGAGAAGTAAAGTCTATTGCTCAAGGTCATGT
GGCTAGAATATGGCAGAGCCATGATTCAGATCCAGGTCTTCTGATTCTTATTCCAGTGTCCTTTCTAGC
ATACCATGTTGCCTCTAAAGATTGCAGCTCCTTATTTACTAGAAAATTGTTCCTGCCCAATCTACATCT
CCACCTCACCCCATCTTTTCTTAAGCACTATGTTTGTGTTTTATCAGTATTATATTCATTGTCTTTGGA
ATACATGTTCTTGTTTGTGTTTGGAAAAAAAATCTCTTTTACCAGCTTGCACTCGGACCAACTTGGAAA
AAAAAAAGCTTAAATGTTTTGCTATGTACAGTTTAAAAATGTGAAGTTTGTAGCTTTAACTTTTTGTA
AGAAAATCTAATAACACTGGCTTAAGTGCTGACTTGAAATGCTATTTTGTAAGGTTTGGATGTAAGTA
ATCAATTGAGGTCAGCAGTTTGTATGAGACATAGCTTCCTCCATTGCCCCCACTCCTTTTTTCTTTTTA
AGTTTGAGATGCTTCCTGTGTTTTTATGTTAGAATTGTTGTTCTCCTTCTTTTCTTCTTCCTATACCTCAT
CACGTTTGTTTTAAATAAACTGTCCTTTGGACCACAAAAAAAAAAAAAAAAA

Figure 9B

>NP_006273.1| serine/threonine-protein kinase 4 [Homo sapiens]
METVQLRNPPRRQLKKLDEDSLTKQPEEVFDVLEKLGEGSYGSVYKAIHKETGQIVAIKQVPVESDLQEI
IKEISIMQQCDSPHVVKYYGSYFKNTDLWIVMEYCGAGSVSDIIRLRNKTLTEDEIATILQSTLKGLEYLHFM
RKIHRDIKAGNILLNTEGHAKLADFGVAGQLTDTMAKRNTVIGTPFWMAPEVIQEIGYNCVADIWSLGITAI
EMAEGKPPYADIHPMRAIFMIPTNPPPTFRKPELWSDNFTDFVKQCLVKSPEQRATATQLLQHPFVRSAKG
VSILRDLINEAMDVKLKRQESQQREVDQDDEENSEEDEMDSGTMVRAVGDEMGTVRVASTMTDGANTMI
EHDDTLPSQLGTMVINAEDEEEEGTMKRRDETMQPAKPSFLEYFEQKEKENQINSFGKSVPGPLKNSSDWK
IPQDGDYEFLKSWTVEDLQKRLLALDPMMEQEIEEIRQKYQSKRQPILDAIEAKKRRQQNF

Figure 9C

>NM_006281.3| Homo sapiens serine/threonine kinase 3 (STK3), transcript variant 1, mRNA
CCGCGGAGTTACGGGAAAGTTGGTCCGAGTTCCCAGAGTTTCCCTCTGTGGTGCCCTAGGCTCGGCCG
GCCGGTGCCCCGGCTCCTTTCCTCCTTTCGGCCTTCGCCGTCCACCAGGTCCCTCTCTCTGTCCCCGGCC
GCCATGGAGCAGCCGCCGGCGCCTAAGAGTAAACTAAAAAAGCTGAGTGAAGACAGTTTGACTAAGC
AGCCTGAAGAAGTTTTTGATGTATTAGAGAAGCTTGGAGAAGGGTCTTATGGAAGTGTATTTAAAGCA
ATACACAAGGAATCCGGTCAAGTTGTCGCAATTAAGCAAGTACCTGTTGAATCAGATCTTCAGGAAAT
AATCAAAGAAATTTCCATAATGCAGCAATGTGACAGCCCATATGTTGTAAAGTACTATGGCAGTTATT
TTAAGAATACAGACCTCTGGATTGTTATGGAGTACTGTGGCGCTGGCTCTGTCTCAGACATAATTAGAT
TACGAAACAAGACATTAATAGAAGATGAAATTGCAACCATTCTTAAATCTACATTGAAAGGACTAGAA
TATTTGCACTTTATGAGAAAAATACACAGAGATATAAAAGCTGGAAATATTCTCCTCAATACAGAAGG
ACATGCAAAATTGGCAGATTTTGGAGTGGCTGGTCAGTTAACAGATACAATGGCAAAACGCAATACTG
TAATAGGAACTCCATTTTGGATGGCTCCTGAGGTGATTCAAGAAATAGGCTATAACTGTGTGGCCGAC
ATCTGGTCCCTTGGCATTACTTCTATAGAAATGGCTGAAGGAAAACCTCCTTATGCTGATATACATCCA
ATGAGGGCTATTTTTATGATTCCCACAAATCCACCACCAACATTCAGAAAGCCAGAACTTTGGTCCGA
TGATTTCACCGATTTTGTTAAAAAGTGTTTGGTGAAGAATCCTGAGCAGAGAGCTACTGCAACACAAC
TTTTACAGCATCCTTTTATCAAGAATGCCAAACCTGTATCAATATTAAGAGACCTGATCACAGAAGCTA
TGGAGATCAAAGCTAAAAGACATGAGGAACAGCAACGAGAATTGGAAGAGGAAGAAGAAAATTCGG
ATGAAGATGAGCTGGATTCCCACACCATGGTGAAGACTAGTGTGGAGAGTGTGGGCACCATGCGGGC
CACAAGCACGATGAGTGAAGGGGCCCAGACCATGATTGAACATAATAGCACGATGTTGGAATCCGAC
TTGGGGACCATGGTGATAAACAGTGAGGATGAGGAAGAAGAAGATGGAACTATGAAAAGAAATGCA
ACCTCACCACAAGTACAAAGACCATCTTTCATGGACTACTTTGATAAGCAAGACTTCAAGAATAAGAG
TCACGAAACGTCTAATCAGAACATGCATGAACCCTTCCCTATGTCCAAAAACGTTTTTCCTGATAACTG
GAAAGTTCCTCAAGATGGAGACTTTGACTTTTTGAAAAATCTAAGTTTAGAAGAACTACAGATGCGGT
TAAAAGCACTGGACCCCATGATGGAACGGGAGATAGAAGAACTTCGTCAGAGATACACTGCGAAAAG
ACAGCCCATTCTGGATGCGATGGATGCAAAGAAAAGAAGGCAGCAAAACTTTTGAGTCTAATTTCCTC
TCTGTTTTTAACTATTCTGGAGACCAAGAAACCACTAGGAATTGAAGGAATATTTGGATATTTTTAATC
CTAAGATTTTGCCCTACAATTAGGCAGAGGTCAAAAAGTGACAATGGTACATGCCCAGGTAAATTCCC
AAAAGGCAGAATTGACAGTTGTATCTGCTGTGCATTCACTCTAAGATGAGGAGAACAAAAGAAGTGT

Figure 9C (Continued)
ATTCTCTTGTTCTGTCAGCTGCATACCAGTAATAAAACTGTTATGAAATGGATTTTCAAGGTCTCTAAA
CCTTGAAAATCCAAAGCTATTGTTGCATTGTACAGCACTGAAGGGCTTTATGTTACAATATTCTTTATT
CCTATCTAGTATACTAGGCTATTTATTGTATCCCCTTAGGTAAACTTATTTATTTATGCTATTTTGCTTT
GTTTCATTTTTTAAGGACAAGATCAGGATAGCTTTGGTGAAGGTAGGGTCATATTAATATGATGATAAT
GTGCAACCAATTTATACTTTCTGCAGGGAGCTATGGGGTACATTCCTTGATTTCCAGGATAGTTTTTCA
AATAGGAAAGCAATAATGGCAGTAGTTCTCAAATGGGCTAGGCCTTTTTTATATTGAAGCAATAATTC
CATTTTTACCCTTTGAAATTTTGTTTTTTTGATTTTTGATGTTTGGTACAAATAGAACTATATATATTTA
GGTAAAATAGATCTATCGTGTTTAAAACCAAAGAAATCAATGGAACCCTTGCACAAAAAAGTGTGATA
AATATTTTTAAATAAAAACTTAATACAAATGTAATTTGTTAATATTGTTTCATGTTTTATGTGTAGATCT
AATAGCTGAACTGATTCAAACTGTAATAAGCTCATCAATTTCATTTCTATGAAAATGTGCTCTGTTGTC
ACAGGATGTTTCTGTTGATTTTATTCATTTCCTGGGAATTGGTAAACATCATGTTCCTGATGATAACCC
AGTAGCAAAAACATTTGTACTGAGTGGTACAAGCCTTGGGGACTGAAAAAAAAAAGATTAAAACCAT
TAAAAAGAAACTCATTTTTACGCTGAATGAACATTTATATGATTGCATTGGGACCAGTCATTTCCTAAG
CTACATATGGCCATCTTGACAGTGTTTTTTCTTTTGTGTGTTTAATTATTATGTGTAAATCATAAAGACA
AATAAATTTCACTGTGCCACCCAGCATA

Figure 9D

>NP_006272.2| serine/threonine-protein kinase 3 isoform 1 [Homo sapiens]
MEQPPAPKSKLKKLSEDSLTKQPEEVFDVLEKLGEGSYGSVFKAIHKESGQVVAIKQVPVESDLQEIIKEISI
MQQCDSPYVVKYYGSYFKNTDLWIVMEYCGAGSVSDIIRLRNKTLIEDEIATILKSTLKGLEYLHFMRKIHR
DIKAGNILLNTEGHAKLADFGVAGQLTDTMAKRNTVIGTPFWMAPEVIQEIGYNCVADIWSLGITSIEMAE
GKPPYADIHPMRAIFMIPTNPPPTFRKPELWSDDFTDFVKKCLVKNPEQRATATQLLQHPFIKNAKPVSILRD
LITEAMEIKAKRHEEQQRELEEEEENSDEDELDSHTMVKTSVESVGTMRATSTMSEGAQTMIEHNSTMLES
DLGTMVINSEDEEEEDGTMKRNATSPQVQRPSFMDYFDKQDFKNKSHENCNQNMHEPFPMSKNVFPDNW
KVPQDGDFDFLKNLSLEELQMRLKALDPMMEREIEELRQRYTAKRQPILDAMDAKKRRQQNF

Figure 10A

>NM_005157.4| Homo sapiens c-abl oncogene 1, non-receptor tyrosine kinase
(ABL1), transcript variant a, mRNA
AAAATGTTGGAGATCTGCCTGAAGCTGGTGGGCTGCAAATCCAAGAAGGGGCTGTCCTCGTCCTCCAGCTGTTATCT
GGAAGAAGCCCTTCAGCGGCCAGTAGCATCTGACTTTGAGCCTCAGGGTCTGAGTGAAGCCGCTCGTTGGAACTCCA
AGGAAAACCTTCTCGCTGGACCCAGTGAAAATGACCCCAACCTTTTCGTTGCACTGTATGATTTTGTGGCCAGTGGA
GATAACACTCTAAGCATAACTAAAGGTGAAAAGCTCCGGGTCTTAGGCTATAATCACAATGGGGAATGGTGTGAAGC
CCAAACCAAAAATGGCCAAGGCTGGGTCCCAAGCAACTACATCACGCCAGTCAACAGTCTGGAGAAACACTCCTGGT
ACCATGGGCCTGTGTCCCGCAATGCCGCTGAGTATCTGCTGAGCAGCGGATCAATGGCAGCTTCTTGGTGCGTGAG
AGTGAGAGCAGTCCTGGCCAGAGGTCCATCTCGCTGAGATACGAAGGGAGGGTGTACCATTACAGGATCAACACTGC
TTCTGATGGCAAGCTCTACGTCTCCTCGAGAGCCGCTTCAACACCCTGGCCGAGTTGGTTCATCATCATTCAACGG
TGGCCGACGGGCTCATCACCACGCTCCATTATCCAGCCCAAAGCGCAACAAGCCCACTGTCTATGGTGTGTCCCCC
AACTACGACAAGTGGGAGATGGAACGCACGGACATCACCATGAAGCACAAGCTGGGCGGGGGCCAGTACGGGGAGGT
GTACGAGGGCGTGTGGAAGAAATACAGCCTGACGGTGGCCGTGAAGACCTTGAAGGAGGACACCATGGAGGTGGAAG
AGTTCTTGAAAGAAGCTGCAGTCATGAAAGAGATCAAACACCCTAACCTGGTGCAGCTCCTTGGGGTCTGCACCCGG
GAGCCCCCGTTCTATATCATCACTGAGTTCATGACCTACGGGAACCTCCTGGACTACCTGAGGGAGTGCAACCGGCA
GGAGGTGAACGCCGTGGTGCTGCTGTACATGGCCACTCAGATCTCGTCAGCCATGGAGTACCTGGAGAAGAAAAACT
TCATCCACAGAGATCTTGCTGCCCGAAACTGCCTGGTAGGGGAGAACCACTTGGTGAAGGTAGCTGATTTTGGCCTG
AGCAGGTTGATGACAGGGGACACCTACACAGCCCATGCTGGAGCCAAGTTCCCCATCAAATGGACTGCACCCGAGAG
CCTGGCCTACAACAAGTTCTCCATCAAGTCCGACGTCTGGGCATTTGGAGTATTGCTTTGGGAAATTGCTACCTATG
GCATGTCCCCTTACCCGGGAATTGACCTGTCCCAGGTGTATGAGCTGCTAGAGAAGGACTACCGCATGGAGCGCCCA
GAAGGCTGCCCAGAGAAGGTCTATGAACTCATGCGAGCATGTTGGCAGTGGAATCCCTCTGACCGGCCCTCCTTTGC
TGAAATCCACCAAGCCTTTGAAACAATGTTCCAGGAATCCAGTATCTCAGACGAAGTGGAAAAGGAGCTGGGGAAAC
AAGGCGTCCGTGGGGCTGTGAGTACCTTGCTGCAGGCCCCAGAGCTGCCCACCAAGACGAGGACCTCCAGGAGAGCT
GCAGAGCACAGAGACACCACTGACGTGCCTGAGATGCCTCACTCCAAGGGCCAGGGAGAGAGCGATCCTCTGGACCA
TGAGCCTGCCGTGTCTCCATTGCTCCCTCGAAAAGAGCGAGGTCCCCCGGAGGGCGGCCTGAATGAAGATGAGCGCC
TTCTCCCCAAAGACAAAAAGACCAACTTGTTCAGCGCCTTGATCAAGAAGAAGAAGAAGACAGCCCCAACCCCTCCC
AAACGCAGCAGCTCCTTCCGGGAGATGGACGGCCAGCCGGAGCGCAGAGGGGCCGGCGAGGAAGAGGGCCGAGACAT
CAGCAACGGGGCACTGGCTTTCACCCCCTTGGACACAGCTGACCCAGCCAAGTCCCCAAAGCCCAGCAATGGGGCTG
GGGTCCCCAATGGAGCCCTCCGGGAGTCCGGGGGCTCAGGCTTCCGGTCTCCCCACCTGTGGAAGAAGTCCAGCACG
CTGACCAGCAGCCGCCTAGCCACCGGCGAGGAGGAGGGCGGTGGCAGCTCCAGCAAGCGCTTCCTGCGCTCTTGCTC
CGCCTCCTGCGTTCCCCATGGGGCCAAGGACACGGAGTGGAGGTCAGTCACGCTGCCTCGGGACTTGCAGTCCACGG
GAAGACAGTTTGACTCGTCCACATTTGGAGGGCACAAAAGTGAGAAGCCGGCTCTGCCTCGGAAGAGGGCAGGGGAG
AACAGGTCTGACCAGGTGACCCGAGGCACAGTAACGCCTCCCCCAGGCTGGTGAAAAGAATGAGGAAGCTGCTGA
TGAGGTCTTCAAAGACATCATGGAGTCCAGCCCGGGCTCCAGCCCGCCCAACCTGACTCCAAAACCCCTCCGGCGGC
AGGTCACCGTGGCCCCTGCCTCGGGCCTCCCCCACAAGGAAGAAGCTGGAAAGGGCAGTGCCTTAGGGACCCCTGCT
GCAGCTGAGCCAGTGACCCCCACCAGCAAAGCAGGCTCAGGTGCACCAGGGGGCACCAGCAAGGGCCCCGCCGAGGA
GTCCAGAGTGAGGAGGCACAAGCACTCCTCTGAGTCGCCAGGGAGGGACAAGGGGAAATTGTCCAGGCTCAAACCTG
CCCCGCCGCCCCCACCAGCAGCCTCTGCAGGGAAGGCTGGAGGAAAGCCCTCGCAGAGCCCGAGCCAGGAGGCGGCC
GGGGAGGCAGTCCTGGGCGCAAAGACAAAAGCCACGAGTCTGGTTGATGCTGTGAACAGTGACGCTGCCAAGCCCAG
CCAGCCGGGAGAGGGCCTCAAAAAGCCCGTGCTCCGGCCACTCCAAAGCCACAGTCCGCCAAGCCGTCGGGGACCC
CCATCAGCCCAGCCCCGTTCCCTCACGTTGCCATCAGCATCCTCGGCCCTGGCAGGGACCAGCCGTCTTCCACC
GCCTTCATCCCTCTCATATCAACCCGAGTGTCTCTTCGGAAAACCCGCCAGCCTCCAGAGCGGATCGCCAGCGGCGC
CATCACCAAGGGCGTGGTCCTGGACAGCACCGAGGCGCTGTGCCTCGCCATCTCTAGGAACTCCGAGCAGATGGCCA
GCCACAGCGCAGTGCTGGAGGCCGGCAAAAACCTCTACACGTTCTGCGTGAGCTATGTGGATTCCATCCAGCAAATG
AGGAACAAGTTTGCCTTCCGAGAGGCCATCAACAAACTGGAGAATAATCTCCGGGAGCTTCAGATCTGCCCGGCGAC
AGCAGGCAGTGGTCCAGCGGCCACTCAGGACTTCAGCAAGCTCCTCAGTTCGGTGAAGGAAATCAGTGACATAGTGC
AGAGGTAGCAGCAGTCAGGGGTCAGGTGTCAGGCCCGTCGGAGCTGCCTGCAGCACATGGGGCTCGCCCATACCCG
TGACAGTGGCTGACAAGGGACTAGTGAGTCAGCACCTTGGCCCAGGAGCTCTGCGCCAGGCAGAGCTGAGGGCCCTG
TGGAGTCCAGCTCTACTACCTACGTTTGCACCGCCTGCCCTCCCGCACCTTCCTCCTCCCGCTCCGTCTCTGTCCT
CGAATTTTATCTGTGGAGTTCCTGCTCCGTGGACTGCAGTCGGCATGCCAGGACCCGCCAGCCCCGCTCCCACCTAG
TGCCCCAGACTGAGCTCTCCAGGCCAGGTGGGAACGGCTGATGTGGACTGTCTTTTTCATTTTTTTCTCTCTGGAGC
CCCTCCTCCCCCGGCTGGGCCTCCTTCTTCCACTTCTCCAAGAATGGAAGCCTGAACTGAGGCCTTGTGTGTCAGGC

Figure 10A (Continued)
```
CCTCTGCCTGCACTCCCTGGCCTTGCCCGTCGTGTGCTGAAGACATGTTTCAAGAACCGCATTTCGGGAAGGGCATG
CACGGGCATGCACACGGCTGGTCACTCTGCCCTCTGCTGCTGCCCGGGGTGGGGTGCACTCGCCATTTCCTCACGTG
CAGGACAGCTCTTGATTTGGGTGGAAAACAGGGTGCTAAAGCCAACCAGCCTTTGGGTCCTGGGCAGGTGGGAGCTG
AAAAGGATCGAGGCATGGGGCATGTCCTTTCCATCTGTCCACATCCCCAGAGCCCAGCTCTTGCTCTCTTGTGACGT
GCACTGTGAATCCTGGCAAGAAAGCTTGAGTCTCAAGGGTGGCAGGTCACTGTCACTGCCGACATCCCTCCCCCAGC
AGAATGGAGGCAGGGGACAAGGGAGGCAGTGGCTAGTGGGGTGAACAGCTGGTGCCAAATAGCCCCAGACTGGGCCC
AGGCAGGTCTGCAAGGGCCCAGAGTGAACCGTCCTTTCACACATCTGGGTGCCCTGAAAGGGCCCTTCCCCTCCCCC
ACTCCTCTAAGACAAAGTAGATTCTTACAAGGCCCTTTCCTTTGGAACAAGACAGCCTTCACTTTTCTGAGTTCTTG
AAGCATTTCAAAGCCCTGCCTCTGTGTAGCCGCCCTGAGAGAGAATAGAGCTGCCACTGGGCACCTGCGCACAGGTG
GGAGGAAAGGGCCTGGCCAGTCCTGGTCCTGGCTGCACTCTTGAACTGGGCGAATGTCTTATTTAATTACCGTGAGT
GACATAGCCTCATGTTCTGTGGGGGTCATCAGGGAGGGTTAGGAAAACCACAAACGGAGCCCCTGAAAGCCTCACGT
ATTTCACAGAGCACGCCTGCCATCTTCTCCCCGAGGCTGCCCCAGGCCGGAGCCCAGATACGGGGCTGTGACTCTG
GGCAGGGACCCGGGGTCTCCTGGACCTTGACAGAGCAGCTAACTCCGAGAGCAGTGGGCAGGTGGCCGCCCCTGAGG
CTTCACGCCGGGAGAAGCCACCTTCCCACCCCTTCATACCGCCTCGTGCCAGCAGCCTCGCACAGGCCCTAGCTTTA
CGCTCATCACCTAAACTTGTACTTTATTTTTCTGATAGAAATGGTTTCCTCTGGATCGTTTTATGCGGTTCTTACAG
CACATCACCTCTTTGCCCCCGACGGCTGTGACGCAGCCGGAGGGAGGCACTAGTCACCGACAGCGGCCTTGAAGACA
GAGCAAAGCGCCCACCCAGGTCCCCCGACTGCCTGTCTCCATGAGGTACTGGTCCCTTCCTTTTGTTAACGTGATGT
GCCACTATATTTTACACGTATCTCTTGGTATGCATCTTTTATAGACGCTCTTTTCTAAGTGGCGTGTGCATAGCGTC
CTGCCCCTGCCCCCTCGGGGGCCTGTGGTGGCTCCCCCTCTGCTTCTCGGGGTCCAGTGCATTTTGTTTCTGTATATG
ATTCTCTGTGGTTTTTTTTGAATCCAAATCTGTCCTCTGTAGTATTTTTTAAATAAATCAGTGTTTACATTAGAA
```

Figure 10B

```
>NP_005148.2| tyrosine-protein kinase ABL1 isoform a [Homo sapiens]
MLEICLKLVGCKSKKGLSSSSSCYLEEALQRPVASDFEPQGLSEAARWNSKENLLAGPSENDPNLFVALYDFVASGD
NTLSITKGEKLRVLGYNHNGEWCEAQTKNGQGWVPSNYITPVNSLEKHSWYHGPVSRNAAEYLLSSGINGSFLVRES
ESSPGQRSISLRYEGRVYHYRINTASDGKLYVSSESRFNTLAELVHHHSTVADGLITTLHYPAPKRNKPTVYGVSPN
YDKWEMERTDITMKHKLGGGQYGEVYEGVWKKYSLTVAVKTLKEDTMEVEEFLKEAAVMKEIKHPNLVQLLGVCTRE
PPFYIITEFMTYGNLLDYLRECNRQEVNAVVLLYMATQISSAMEYLEKKNFIHRDLAARNCLVGENHLVKVADFGLS
RLMTGDTYTAHAGAKFPIKWTAPESLAYNKFSIKSDVWAFGVLLWEIATYGMSPYPGIDLSQVYELLEKDYRMERPE
GCPEKVYELMRACWQWNPSDRPSFAEIHQAFETMFQESSISDEVEKELGKQGVRGAVSTLLQAPELPTKTRTSRRAA
EHRDTTDVPEMPHSKGQGESDPLDHEPAVSPLLPRKERGPPEGGLNEDERLLPKDKKTNLFSALIKKKKKTAPTPPK
RSSSFREMDGQPERRGAGEEEGRDISNGALAFTPLDTADPAKSPKPSNGAGVPNGALRESGGSGFRSPHLWKKSSTL
TSSRLATGEEEGGGSSSKRFLRSCSASCVPHGAKDTEWRSVTLPRDLQSTGRQFDSSTFGGHKSEKPALPRKRAGEN
RSDQVTRGTVTPPPRLVKKNEEAADEVFKDIMESSPGSSPPNLTPKPLRRQVTVAPASGLPHKEEAGKGSALGTPAA
AEPVTPTSKAGSGAPGGTSKGPAEESRVRRHKHSSESPGRDKGKLSRLKPAPPPPPAASAGKAGGKPSQSPSQEAAG
EAVLGAKTKATSLVDAVNSDAAKPSQPGEGLKKPVLPATPKPQSAKPSGTPISPAPVPSTLPSASSALAGDQPSSTA
FIPLISTRVSLRKTRQPPERIASGAITKGVVLDSTEALCLAISRNSEQMASHSAVLEAGKNLYTFCVSYVDSIQQMR
NKFAFREAINKLENNLRELQICPATAGSGPAATQDFSKLLSSVKEISDIVQR
```

A

B

SEQUENCE LISTING

```
<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: Target sequence

<400> SEQUENCE: 1
agttgagtga tagctgggaa a                                              21

<210> SEQ ID NO 2
<211> LENGTH: 21
```

```
<212> TYPE: DNA
<213> ORGANISM: Artificial Sequence
<220> FEATURE:
<223> OTHER INFORMATION: Target sequence

<400> SEQUENCE: 2
gccctcatgt agtcaaatat t                                              21

<210> SEQ ID NO 3
<211> LENGTH: 21
<212> TYPE: DNA
<213> ORGANISM: Artificial Sequence
<220> FEATURE:
<223> OTHER INFORMATION: Target sequence

<400> SEQUENCE: 3
gccaagcgga atacagtgat a                                              21

<210> SEQ ID NO 4
<211> LENGTH: 21
<212> TYPE: DNA
<213> ORGANISM: Artificial Sequence
<220> FEATURE:
<223> OTHER INFORMATION: Target sequence

<400> SEQUENCE: 4
ctaagaagag acggcaacaa a                                              21

<210> SEQ ID NO 5
<211> LENGTH: 21
<212> TYPE: DNA
<213> ORGANISM: Artificial Sequence
<220> FEATURE:
<223> OTHER INFORMATION: Target sequence

<400> SEQUENCE: 5
cccagttaaa tgttcaccaa t                                              21

<210> SEQ ID NO 6
<211> LENGTH: 21
<212> TYPE: DNA
<213> ORGANISM: Artificial Sequence
<220> FEATURE:
<223> OTHER INFORMATION: Target sequence

<400> SEQUENCE: 6
caggtgatac tatcaaccaa a                                              21

<210> SEQ ID NO 7
<211> LENGTH: 17
<212> TYPE: DNA
<213> ORGANISM: Artificial Sequence
<220> FEATURE:
<223> OTHER INFORMATION: Primer YAP1 exon1-F

<400> SEQUENCE: 7
cttctccacc tcggccc                                                   17

<210> SEQ ID NO 8
<211> LENGTH: 20
<212> TYPE: DNA
<213> ORGANISM: Artificial Sequence
<220> FEATURE:
<223> OTHER INFORMATION: Primer YAP1 -exon1-R

<400> SEQUENCE: 8
```

```
tccaggtcgg tctccgagtc                                                20

<210> SEQ ID NO 9
<211> LENGTH: 20
<212> TYPE: DNA
<213> ORGANISM: Artificial Sequence
<220> FEATURE:
<223> OTHER INFORMATION: Primer YAP1-exon4-F

<400> SEQUENCE: 9
catcgaatat cccaaattgc                                                20

<210> SEQ ID NO 10
<211> LENGTH: 19
<212> TYPE: DNA
<213> ORGANISM: Artificial Sequence
<220> FEATURE:
<223> OTHER INFORMATION: Primer YAP1-Intron4/5-R

<400> SEQUENCE: 10
caaaagtgga aggctggtt                                                 19

<210> SEQ ID NO 11
<211> LENGTH: 21
<212> TYPE: DNA
<213> ORGANISM: Artificial Sequence
<220> FEATURE:
<223> OTHER INFORMATION: Primer YAP1-exon7-F

<400> SEQUENCE: 11
cagccctgat gttagctttt c                                              21

<210> SEQ ID NO 12
<211> LENGTH: 20
<212> TYPE: DNA
<213> ORGANISM: Artificial Sequence
<220> FEATURE:
<223> OTHER INFORMATION: Primer YAP1-exon7-R

<400> SEQUENCE: 12
aaatttccgg tgcatgtgtc                                                20

<210> SEQ ID NO 13
<211> LENGTH: 21
<212> TYPE: DNA
<213> ORGANISM: Artificial Sequence
<220> FEATURE:
<223> OTHER INFORMATION: Primer YAP1-F

<400> SEQUENCE: 13
caatagctca gatcctttcc t                                              21

<210> SEQ ID NO 14
<211> LENGTH: 22
<212> TYPE: DNA
<213> ORGANISM: Artificial Sequence
<220> FEATURE:
<223> OTHER INFORMATION: Primer YAP1-R

<400> SEQUENCE: 14
tagtatcacc tgtatccatc tc                                             22

<210> SEQ ID NO 15
<211> LENGTH: 21
<212> TYPE: DNA
<213> ORGANISM: Artificial Sequence
```

```
<220> FEATURE:
<223> OTHER INFORMATION: Primer TA-p73-F

<400> SEQUENCE: 15
gcaccacgtt tgagcacctc t                                              21

<210> SEQ ID NO 16
<211> LENGTH: 21
<212> TYPE: DNA
<213> ORGANISM: Artificial Sequence
<220> FEATURE:
<223> OTHER INFORMATION: Primer TA-p73-R

<400> SEQUENCE: 16
gcagattgaa ctgggccatg a                                              21

<210> SEQ ID NO 17
<211> LENGTH: 22
<212> TYPE: DNA
<213> ORGANISM: Artificial Sequence
<220> FEATURE:
<223> OTHER INFORMATION: Primer ABL1-F

<400> SEQUENCE: 17
cccaaccttt tcgttgcact gt                                             22

<210> SEQ ID NO 18
<211> LENGTH: 22
<212> TYPE: DNA
<213> ORGANISM: Artificial Sequence
<220> FEATURE:
<223> OTHER INFORMATION: Primer ABL1-R

<400> SEQUENCE: 18
cggctctcgg aggagacgta ga                                             22

<210> SEQ ID NO 19
<211> LENGTH: 20
<212> TYPE: DNA
<213> ORGANISM: Artificial Sequence
<220> FEATURE:
<223> OTHER INFORMATION: Primer GAPDH-F

<400> SEQUENCE: 19
gaaggtgaag gtcggagtca                                                20

<210> SEQ ID NO 20
<211> LENGTH: 22
<212> TYPE: DNA
<213> ORGANISM: Artificial Sequence
<220> FEATURE:
<223> OTHER INFORMATION: Primer GAPDH-R

<400> SEQUENCE: 20
ggggtcattg atggcaacaa ta                                             22

<210> SEQ ID NO 21
<211> LENGTH: 58
<212> TYPE: DNA
<213> ORGANISM: Artificial Sequence
<220> FEATURE:
<223> OTHER INFORMATION: Forward oligo sequence

<400> SEQUENCE: 21
ccggagttga gtgatagctg ggaaactcga gtttcccagc tatcactcaa cttttttg      58
```

```
<210> SEQ ID NO 22
<211> LENGTH: 58
<212> TYPE: DNA
<213> ORGANISM: Artificial Sequence
<220> FEATURE:
<223> OTHER INFORMATION: Reverse oligo sequence

<400> SEQUENCE: 22
aattcaaaaa agttgagtga tagctgggaa actcgagttt cccagctatc actcaact       58

<210> SEQ ID NO 23
<211> LENGTH: 58
<212> TYPE: DNA
<213> ORGANISM: Artificial Sequence
<220> FEATURE:
<223> OTHER INFORMATION: Forward oligo sequence

<400> SEQUENCE: 23
ccgggccctc atgtagtcaa atattctcga gaatatttga ctacatgagg gctttttg       58

<210> SEQ ID NO 24
<211> LENGTH: 58
<212> TYPE: DNA
<213> ORGANISM: Artificial Sequence
<220> FEATURE:
<223> OTHER INFORMATION: Reverse oligo sequence

<400> SEQUENCE: 24
aattcaaaaa gccctcatgt agtcaaatat tctcgagaat atttgactac atgagggc       58

<210> SEQ ID NO 25
<211> LENGTH: 58
<212> TYPE: DNA
<213> ORGANISM: Artificial Sequence
<220> FEATURE:
<223> OTHER INFORMATION: Forward oligo sequence

<400> SEQUENCE: 25
ccgggccaag cggaatacag tgatactcga gtatcactgt attccgcttg gctttttg       58

<210> SEQ ID NO 26
<211> LENGTH: 58
<212> TYPE: DNA
<213> ORGANISM: Artificial Sequence
<220> FEATURE:
<223> OTHER INFORMATION: Reverse oligo sequence

<400> SEQUENCE: 26
aattcaaaaa gccaagcgga atacagtgat actcgagtat cactgtattc cgcttggc       58

<210> SEQ ID NO 27
<211> LENGTH: 58
<212> TYPE: DNA
<213> ORGANISM: Artificial Sequence
<220> FEATURE:
<223> OTHER INFORMATION: Forward oligo sequence

<400> SEQUENCE: 27
ccggctaaga agagacggca acaaactcga gtttgttgcc gtctcttctt agttttg        58

<210> SEQ ID NO 28
<211> LENGTH: 58
<212> TYPE: DNA
<213> ORGANISM: Artificial Sequence
<220> FEATURE:
<223> OTHER INFORMATION: Reverse oligo sequence
```

```
<400> SEQUENCE: 28
aattcaaaaa ctaagaagag acggcaacaa actcgagttt gttgccgtct cttcttag        58

<210> SEQ ID NO 29
<211> LENGTH: 5396
<212> TYPE: DNA
<213> ORGANISM: Homo sapiens

<400> SEQUENCE: 29
gccgccgcca gggaaaagaa agggaggaag gaaggaacaa gaaaaggaaa taagagaaa       60 ggggaggcgg ggaaaggcaa cgagctgtcc ggcctccgtc aagggagttg gagggaaaaa     120
gttctcaggc gccgcaggtc cgagtgcctc gcagcccctc ccgaggcgca gccgccagac     180
cagtggagcc ggggcgcagg gcggggggcgg aggcgccggg gcgggggatg cggggccgcg    240
gcgcagcccc ccggccctga gagcgaggac agcgccgccc ggcccgcagc cgtcgccgct    300
tctccacctc ggcccgtgga gccggggcgt ccgggcgtag ccctcgctcg cctgggtcag    360
ggggtgcgcg tcggggagg cagaagccat ggatcccggg cagcagccgc cgcctcaacc      420
ggccccccag ggccaagggc agccgccttc gcagcccccg caggggcagg gcccgccgtc    480
cggacccggg caaccggcac ccgcggcgac ccaggcggcg ccgcaggcac ccccgccgg     540 gcatcagatc gtgcacgtcc gcggggactc ggagaccgac ctggaggcgc tcttcaacgc    600
cgtcatgaac cccaagacgg ccaacgtgcc ccagaccgtg cccatgaggc tccggaagct    660
gcccgactcc ttcttcaagc cgccggagcc caaatcccac tcccgacagg ccagtactga    720
tgcaggcact gcaggagccc tgactccaca gcatgttcga gctcattcct ctccagcttc    780
tctgcagttg ggagctgttt ctcctgggac actgaccccc actggagtag tctctggccc    840
agcagctaca cccacagctc agcatcttcg acagtcttct tttgagatac ctgatgatgt    900
acctctgcca gcaggttggg agatggcaaa gacatcttct ggtcagagat acttcttaaa    960
tcacatcgat cagacaacaa catggcagga ccccaggaag gccatgctgt cccagatgaa   1020
cgtcacagcc cccaccagtc caccagtgca gcagaatatg atgaactcgg cttcaggtcc   1080
tcttcctgat ggatgggaac aagccatgac tcaggatgga gaaatttact atataaacca   1140
taagaacaag accacctctt ggctagaccc aaggcttgac cctcgttttg ccatgaacca   1200
gagaatcagt cagagtgctc cagtgaaaca gccaccaccc ctggctcccc agagcccaca   1260
gggaggcgtc atgggtggca gcaactccaa ccagcagcaa cagatgcgac tgcagcaact   1320
gcagatggag aaggagaggc tgcggctgaa acagcaagaa ctgcttcggc aggcaatgcg   1380
gaatatcaat cccagcacag caaattctcc aaaatgtcag gagttagccc tgcgtagcca   1440
gttaccaaca ctggagcagg atggtgggac tcaaaatcca gtgtcttctc ccgggatgtc   1500
tcaggaattg agaacaatga cgaccaatag ctcagatcct ttccttaaca gtggcaccta   1560
tcactctcga gatgagagta cagacagtgg actaagcatg agcagctaca gtgtccctcg   1620
aaccccagat gacttcctga acagtgtgga tgagatggat acaggtgata ctatcaacca   1680 aagcacctg ccctcacagc agaaccgttt cccagactac cttgaagcca ttcctgggac    1740
aaaatgtgga cttggaacac tggaaggaga tggaatgaac atagaaggag aggagctgat   1800
gccaagtctg caggaagctt tgagttctga catccttaat gacatggagt ctgttttggc   1860
tgccaccaag ctagataaag aaagctttct tacatggtta tagagccctc aggcagactg   1920
aattctaaat ctgtgaagga tctaaggaga cacatgcacc ggaaatttcc ataagccagt   1980
```

-continued

```
tgcagttttc aggctaatac agaaaaagat gaacaaacgt ccagcaagat actttaatcc      2040
tctattttgc tcttccttgt ccattgctgc tgttaatgta ttgctgacct ctttcacagt      2100
tggctctaaa gaatcaaaag aaaaaaactt tttatttctt ttgctattaa aactactgtt      2160
cattttgggg gctgggggaa gtgagcctgt ttggatgatg gatgccattc cttttgccca      2220
gttaaatgtt caccaatcat tttaactaaa tactcagact tagaagtcag atgcttcatg      2280
tcacagcatt tagtttgttc aacagttgtt tcttcagctt cctttgtcca gtggaaaaac      2340
atgatttact ggtctgacaa gccaaaaatg ttatatctga tattaaatac ttaatgctga      2400
tttgaagaga tagctgaaac caaggctgaa gactgtttta ctttcagtat tttcttttcc      2460
tcctagtgct atcattagtc acataatgac cttgatttta ttttaggagc ttataaggca      2520
tgagacaatt tccatataaa tatattaatt attgccacat actctaatat agattttggt      2580
ggataatttt gtgggtgtgc attttgttct gttttgttgg gttttttgtt tttttttgttt      2640 ttggcagggt cggtggggg gttggttggt tggttggttt tgtcggaacc taggcaaatg      2700
accatattag tgaatctgtt aatagttgta gcttgggatg gttattgtag ttgttttggt      2760
aaaatcttca tttcctggtt ttttttacca ccttatttaa atctcgatta tctgctctct      2820
cttttatata catacacaca cccaaacata acatttataa tagtgtggta gtggaatgta      2880
tcctttttta ggtttccctg ctttccagtt aattttaaa atggtagcgc tttgtatgca      2940
tttagaatac atgactagta gtttatattt cactggtagt ttaaatctgg ttggggcagt      3000
ctgcagatgt ttgaagtagt ttagtgttct agaaagagct attactgtgg atagtgccta      3060
ggggagtgct ccacgccctc tgggcatacg gtagatatta tctgatgaat tggaaaggag      3120
caaaccagaa atggctttat tttctcccc tt ggactaattt ttaagtctcg attggaattc      3180
agtgagtagg ttcataatgt gcatgacaga aataagcttt atagtggttt accttcattt      3240
agctttggaa gttttctttg ccttagtttt ggaagtaaat tctagtttgt agttctcatt      3300
tgtaatgaac acattaacga ctagattaaa atattgcctt caagattgtt cttacttaca      3360
agacttgctc ctacttctat gctgaaaatt gaccctggat agaatactat aaggttttga      3420
gttagctgga aaagtgatca gattaataaa tgtatattgg tagttgaatt tagcaaagaa      3480
atagagataa tcatgattat accttttattt ttacaggaag agatgatgta actagagtat      3540
gtgtctacag gagtaataat ggtttccaaa gagtattttt taaaggaaca aaacgagcat      3600
gaattaactc ttcaatataa gctatgaagt aatagttggt tgtgaattaa agtggcacca      3660
gctagcacct ctgtgtttta agggtctttc aatgtttcta gaataagccc ttattttcaa      3720
gggttcataa caggcataaa atctcttctc ctggcaaaag ctgctatgaa aagcctcagc      3780
ttgggaagat agattttttt ccccccaatt acaaaatcta agtattttgg cccttcaatt      3840
tggaggaggg caaaagttgg aagtaagaag ttttatttta agtactttca gtgctcaaaa      3900
aaatgcaatc actgtgttgt atataatagt tcataggttg atcactcata ataattgact      3960
ctaaggcttt tattaagaaa acagcagaaa gattaaatct tgaattaagt ctgggggggaa      4020 atggccactg cagatggagt tttagagtag taatgaaatt ctacctagaa tgcaaaattg      4080
ggtatatgaa ttcatagca tgttgttggg attttttta atgtgcagaa gatcaaagct      4140
acttggaagg agtgcctata atttgccagt agccacagat taagattata tcttatatat      4200
cagcagatta gctttagctt agggggaggg tgggaaagtt tggggggggg gttgtgaaga      4260 tttagggggga ccttgataga gaactttata aacttcttc tctttaataa agacttgtct      4320
tacaccgtgc tgccattaaa ggcagctgtt ctagagtttc agtcacctaa gtacacccac      4380
```

```
aaaacaatat gaatatggag atcttccttt accccctcaac tttaatttgc ccagttatac    4440
ctcagtgttg tagcagtact gtgatacctg gcacagtgct ttgatcttac gatgccctct    4500
gtactgacct gaaggagacc taagagtcct ttccctttt gagtttgaat catagccttg    4560
atgtggtctc ttgttttatg tccttgttcc taatgtaaaa gtgcttaact gcttcttggt    4620
tgtattgggt agcattggga taagatttta actgggtatt cttgaattgc ttttacaata    4680
aaccaatttt ataatcttta aatttatcaa cttttacat ttgtgttatt ttcagtcagg    4740
gcttcttaga tctacttatg gttgatggag cacattgatt tggagtttca gatcttccaa    4800
agcactattt gttgtaataa cttttctaaa tgtagtgcct ttaaaggaaa aatgaacaca    4860
gggaagtgac tttgctacaa ataatgttgc tgtgttaagt attcatatta aatacatgcc    4920
ttctatatgg aacatggcag aaagactgaa aaataacagt aattaattgt gtaattcaga    4980
attcatacca atcagtgttg aaactcaaac attgcaaaag tgggtggcaa tattcagtgc    5040
ttaacacttt tctagcgttg gtacatctga gaaatgagtg ctcaggtgga ttttatcctc    5100
gcaagcatgt tgttataaga attgtgggtg tgcctatcat aacaattgtt ttctgtatct    5160
tgaaaaagta ttctccacat tttaaatgtt ttatattaga gaattcttta atgcacactt    5220
gtcaaatata tatatatagt accaatgtta ccttttatt ttttgtttta gatgtaagag    5280
catgctcata tgttaggtac ttacataaat tgttacatta ttttttctta tgtaatacct    5340
ttttgtttgt ttatgtggtt caaatatatt ctttccttaa actcttaaaa aaaaaa        5396

<210> SEQ ID NO 30
<211> LENGTH: 504
<212> TYPE: PRT
<213> ORGANISM: Homo sapiens

<400> SEQUENCE: 30

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190
```

```
Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
        210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
        275                 280                 285

Ser Pro Gln Gly Gly Val Met Gly Gly Ser Asn Ser Asn Gln Gln Gln
        290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Ala Met Arg Asn Ile Asn Pro Ser
                325                 330                 335

Thr Ala Asn Ser Pro Lys Cys Gln Glu Leu Ala Leu Arg Ser Gln Leu
            340                 345                 350

Pro Thr Leu Glu Gln Asp Gly Gly Thr Gln Asn Pro Val Ser Ser Pro
        355                 360                 365

Gly Met Ser Gln Glu Leu Arg Thr Met Thr Thr Asn Ser Ser Asp Pro
370                 375                 380

Phe Leu Asn Ser Gly Thr Tyr His Ser Arg Asp Glu Ser Thr Asp Ser
385                 390                 395                 400

Gly Leu Ser Met Ser Ser Tyr Ser Val Pro Arg Thr Pro Asp Asp Phe
                405                 410                 415

Leu Asn Ser Val Asp Glu Met Asp Thr Gly Asp Thr Ile Asn Gln Ser
            420                 425                 430

Thr Leu Pro Ser Gln Gln Asn Arg Phe Pro Asp Tyr Leu Glu Ala Ile
        435                 440                 445

Pro Gly Thr Asn Val Asp Leu Gly Thr Leu Glu Gly Asp Gly Met Asn
450                 455                 460

Ile Glu Gly Glu Glu Leu Met Pro Ser Leu Gln Glu Ala Leu Ser Ser
465                 470                 475                 480

Asp Ile Leu Asn Asp Met Glu Ser Val Leu Ala Ala Thr Lys Leu Asp
                485                 490                 495

Lys Glu Ser Phe Leu Thr Trp Leu
            500
```

<210> SEQ ID NO 31
<211> LENGTH: 5234
<212> TYPE: DNA
<213> ORGANISM: Homo sapiens

<400> SEQUENCE: 31

| | | |
|---|---|---|
| gccgccgcca gggaaaagaa agggaggaag gaaggaacaa gaaaaggaaa taagagaaa | 60 |
| ggggaggcgg ggaaaggcaa cgagctgtcc ggcctccgtc aagggagttg gagggaaaaa | 120 |
| gttctcaggc gccgcaggtc cgagtgcctc gcagcccctc ccgaggcgca gccgccagac | 180 |
| cagtggagcc ggggcgcagg gcggggcgg aggcgccggg gcggggatg cggggccgcg | 240 |
| gcgcagcccc ccggccctga gagcgaggac agcgccgccc ggcccgcagc cgtcgccgct | 300 |
| tctccacctc ggcccgtgga gccggggcgt ccgggcgtag ccctcgctcg cctgggtcag | 360 |

```
ggggtgcgcg tcgggggagg cagaagccat ggatcccggg cagcagccgc cgcctcaacc    420
ggcccccag  ggccaagggc agccgccttc gcagcccccg caggggcagg gcccgccgtc    480
cggacccggg caaccggcac ccgcggcgac ccaggcggcg ccgcaggcac ccccgccgg     540
gcatcagatc gtgcacgtcc gcggggactc ggagaccgac ctggaggcgc tcttcaacgc    600
cgtcatgaac cccaagacgg ccaacgtgcc ccagaccgtg cccatgaggc tccggaagct    660
gcccgactcc ttcttcaagc cgccggagcc caaatcccac tcccgacagg ccagtactga    720
tgcaggcact gcaggagccc tgactccaca gcatgttcga gctcattcct ctccagcttc    780
tctgcagttg ggagctgttt ctcctgggac actgaccccc actggagtag tctctggccc    840
agcagctaca cccacagctc agcatcttcg acagtcttct tttgagatac ctgatgatgt    900
acctctgcca gcaggttggg agatggcaaa gacatcttct ggtcagagat acttcttaaa    960
tcacatcgat cagacaacaa catggcagga ccccaggaag gccatgctgt cccagatgaa   1020
cgtcacagcc cccaccagtc caccagtgca gcagaatatg atgaactcgg cttcagccat   1080
gaaccagaga atcagtcaga gtgctccagt gaaacagcca ccaccctgg ctccccagag    1140
cccacaggga ggcgtcatgg gtggcagcaa ctccaaccag cagcaacaga tgcgactgca   1200
gcaactgcag atggagaagg agaggctgcg gctgaaacag caagaactgc ttcggcagga   1260
gttagccctg cgtagccagt taccaacact ggagcaggat ggtgggactc aaaatccagt   1320
gtcttctccc gggatgtctc aggaattgag aacaatgacg accaatagct cagatccttt   1380
ccttaacagt ggcacctatc actctcgaga tgagagtaca gacagtggac taagcatgag   1440
cagctacagt gtccctcgaa ccccagatga cttcctgaac agtgtggatg agatggatac   1500
aggtgatact atcaaccaaa gcaccctgcc ctcacagcag aaccgtttcc cagactacct   1560
tgaagccatt cctgggacaa atgtggacct tggaacactg aaggagatg gaatgaacat    1620
agaaggagag gagctgatgc caagtctgca ggaagctttg agttctgaca tccttaatga   1680
catggagtct gttttggctg ccaccaagct agataaagaa agctttctta catggttata   1740
gagccctcag gcagactgaa ttctaaatct gtgaaggatc taaggagaca catgcaccgg   1800
aaatttccat aagccagttg cagttttcag gctaatacag aaaaagatga acaaacgtcc   1860
agcaagatac tttaatcctc tattttgctc ttccttgtcc attgctgctg ttaatgtatt   1920
gctgacctct ttcacagttg gctctaaaga atcaaaagaa aaaacttttt tatttctttt   1980
gctattaaaa ctactgttca ttttgggggc tgggggaagt gagcctgttt ggatgatgga   2040
tgccattcct tttgcccagt taaatgttca ccaatcattt taactaaata ctcagactta   2100
gaagtcagat gcttcatgtc acagcattta gtttgttcaa cagttgtttc ttcagcttcc   2160
tttgtccagt ggaaaaacat gatttactgg tctgacaagc caaaatgtt  atatctgata   2220
ttaaatactt aatgctgatt tgaagagata gctgaaacca aggctgaaga ctgttttact   2280
ttcagtattt tcttttcctc ctagtgctat cattagtcac ataatgacct tgatttttatt  2340
ttaggagctt ataaggcatg agacaatttc catataaata tattaattat tgccacatac   2400
tctaatatag attttggtgg ataattttgt gggtgtgcat tttgttctgt tttgttgggt   2460
tttttgtttt ttttgttttt ggcagggtcg gtggggggg  tggttggttg gttggttttg   2520
tcggaaccta ggcaaatgac catattagtg aatctgttaa tagttgtagc ttgggatggt   2580
tattgtagtt gttttggtaa aatcttcatt tcctggtttt ttttaccacc ttatttaaat   2640
ctcgattatc tgctctctct tttatataca tacacacacc caaacataac atttataata   2700
```

```
gtgtggtagt ggaatgtatc cttttttagg tttccctgct ttccagttaa ttttaaaat    2760 ggtagcgctt tgtatgcatt tagaatacat gactagtagt ttatatttca ctggtagttt    2820
aaatctggtt ggggcagtct gcagatgttt gaagtagttt agtgttctag aaagagctat    2880
tactgtggat agtgcctagg ggagtgctcc acgccctctg ggcatacggt agatattatc    2940
tgatgaattg gaaaggagca aaccagaaat ggctttattt tctcccttgg actaattttt    3000
aagtctcgat tggaattcag tgagtaggtt cataatgtgc atgacagaaa taagctttat    3060
agtggtttac cttcatttag ctttggaagt tttctttgcc ttagttttgg aagtaaattc    3120
tagtttgtag ttctcatttg taatgaacac attaacgact agattaaaat attgccttca    3180
agattgttct tacttacaag acttgctcct acttctatgc tgaaaattga ccctggatag    3240
aatactataa ggttttgagt tagctggaaa agtgatcaga ttaataaatg tatattggta    3300
gttgaattta gcaaagaaat agagataatc atgattatac ctttatttt acaggaagag    3360 atgatgtaac tagagtatgt gtctacagga gtaataatgg tttccaaaga gtatttttta    3420
aaggaacaaa acgagcatga attaactctt caatataagc tatgaagtaa tagttggttg    3480
tgaattaaag tggcaccagc tagcacctct gtgttttaag ggtctttcaa tgttctaga    3540 ataagccctt atttttcaagg gttcataaca ggcataaaat ctcttctcct ggcaaaagct    3600
gctatgaaaa gcctcagctt gggaagatag attttttcc ccccaattac aaaatctaag    3660
tattttggcc cttcaatttg gaggagggca aaagttggaa gtaagaagtt ttattttaag    3720
tactttcagt gctcaaaaaa atgcaatcac tgtgttgtat ataatagttc ataggttgat    3780
cactcataat aattgactct aaggctttta ttaagaaaac agcagaaaga ttaaatcttg    3840
aattaagtct ggggggaaat ggccactgca gatggagttt tagagtagta atgaaattct    3900
acctagaatg caaaattggg tatatgaatt acatagcatg ttgttgggat ttttttaat    3960 gtgcagaaga tcaaagctac ttggaaggag tgcctataat ttgccagtag ccacagatta    4020
agattatatc ttatatatca gcagattagc tttagcttag ggggaggtg ggaaagtttg    4080 ggggggggt tgtgaagatt taggggggacc ttgatagaga actttataaa cttctttctc    4140
tttaataaag acttgtctta caccgtgctg ccattaaagg cagctgttct agagtttcag    4200
tcacctaagt acacccacaa acaatatga atatggagat cttcctttac ccctcaactt    4260
taatttgccc agttatacct cagtgttgta gcagtactgt gatacctggc acagtgcttt    4320
gatcttacga tgccctctgt actgacctga aggagaccta agagtccttt cccttttga    4380 gtttgaatca tagccttgat gtggtctctt gttttatgtc cttgttccta atgtaaaagt    4440
gcttaactgc ttcttggttg tattgggtag cattgggata agattttaac tgggtattct    4500
tgaattgctt ttacaataaa ccaatttat aatcttaaa tttatcaact ttttacattt    4560
gtgttatttt cagtcagggc ttcttagatc tacttatggt tgatggagca cattgatttg    4620
gagtttcaga tcttccaaag cactatttgt tgtaataact tttctaaatg tagtgccttt    4680
aaaggaaaaa tgaacacagg gaagtgactt tgctacaaat aatgttgctg tgttaagtat    4740
tcatattaaa tacatgcctt ctatatggaa catggcagaa agactgaaaa ataacagtaa    4800
ttaattgtgt aattcagaat tcataccaat cagtgttgaa actcaaacat tgcaaaagtg    4860
ggtggcaata ttcagtgctt aacacttttc tagcgttggt acatctgaga aatgagtgct    4920
caggtggatt ttatcctcgc aagcatgttg ttataagaat tgtgggtgtg cctatcataa    4980
caattgtttt ctgtatcttg aaaaagtatt ctccacattt taaatgtttt atattagaga    5040
attctttaat gcacacttgt caaatatata tatatagtac caatgttacc tttttatttt    5100
```
ttgttttaga tgtaagagca tgctcatatg ttaggtactt acataaattg ttacattatt    5160
ttttcttatg taatacccttt tgtttgttt atgtggttca aatatattct ttccttaaac    5220
tcttaaaaaa aaaa    5234

<210> SEQ ID NO 32
<211> LENGTH: 449
<212> TYPE: PRT
<213> ORGANISM: Homo sapiens

<400> SEQUENCE: 32

Met Asp Pro Gly Gln Gln Pro Pro Gln Ala Pro Gln Gly Gln
1               5                   10                  15

Gly Gln Pro Pro Ser Gln Pro Gln Gly Gln Gly Pro Ser Gly
                20                  25                  30

Pro Gly Gln Pro Ala Pro Ala Thr Gln Ala Ala Pro Gln Ala Pro
                35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
            210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
            275                 280                 285

Arg Gln Glu Leu Ala Leu Arg Ser Gln Leu Pro Thr Leu Glu Gln Asp
            290                 295                 300

Gly Gly Thr Gln Asn Pro Val Ser Ser Pro Gly Met Ser Gln Glu Leu
305                 310                 315                 320

Arg Thr Met Thr Thr Asn Ser Ser Asp Pro Phe Leu Asn Ser Gly Thr
                325                 330                 335

Tyr His Ser Arg Asp Glu Ser Thr Asp Ser Gly Leu Ser Met Ser Ser

```
              340                 345                 350
Ser Val Pro Arg Thr Pro Asp Asp Phe Leu Asn Ser Val Asp Glu Met
            355                 360                 365

Asp Thr Gly Asp Thr Ile Asn Gln Ser Thr Leu Pro Ser Gln Gln Asn
            370                 375                 380

Arg Phe Pro Asp Tyr Leu Glu Ala Ile Pro Gly Thr Asn Val Asp Leu
385                 390                 395                 400

Gly Thr Leu Glu Gly Asp Gly Met Asn Ile Glu Gly Glu Glu Leu Met
                405                 410                 415

Pro Ser Leu Gln Glu Ala Leu Ser Ser Asp Ile Leu Asn Asp Met Glu
            420                 425                 430

Ser Val Leu Ala Ala Thr Lys Leu Asp Lys Glu Ser Phe Leu Thr Trp
            435                 440                 445

Leu

<210> SEQ ID NO 33
<211> LENGTH: 6344
<212> TYPE: DNA
<213> ORGANISM: Homo sapiens

<400> SEQUENCE: 33
gcggaagtgt gggagggtct gcggggcggg ctcaggaggt ccgcgggagg atggagcagt      60
gagcgggtct gggcggctgc tggcagcgcc atggagacgg tacagctgag gaacccgccg     120
cgccggcagc tgaaaaagtt ggatgaagat agtttaacca acaaccaga agaagtattt      180
gatgtcttag agaaacttgg agaagggtcc tatggcagcg tatacaaagc tattcataaa     240
gagaccggcc agattgttgc tattaagcaa gttcctgtgg aatcagacct ccaggagata     300
atcaaagaaa tctctataat gcagcaatgt gacagccctc atgtagtcaa atattatggc     360
agttatttta agaacacaga cttatggatc gttatggagt actgtggggc tggttctgta     420
tctgatatca ttcgattacg aaataaaacg ttaacagaag atgaaatagc tacaatatta     480
caatcaactc ttaagggact tgaatacctt cattttatga aaaaatacac ccgagatatc     540
aaggcaggaa atattttgct aaatacagaa ggacatgcaa acttgcaga ttttggggta      600
gcaggtcaac ttacagatac catggccaag cggaatacag tgataggaac accattttgg     660
atggctccag aagtgattca ggaaattgga tacaactgtg tagcagacat ctggtccctg     720
ggaataactg ccatagaaat ggctgaagga agccccctt atgctgatat ccatccaatg      780
agggcaatct tcatgattcc tacaaatcct cctcccacat tccgaaaacc agagctatgg     840
tcagataact ttacagattt tgtgaaacag tgtcttgtaa agagccctga gcagagggcc     900
acagccactc agctcctgca gcacccattt gtcaggagtg ccaaaggagt gtcaatactg     960
cgagacttaa ttaatgaagc catggatgtg aaactgaaac gccaggaatc ccagcagcgg    1020
gaagtggacc aggacgatga agaaaactca gaagaggatg aaatggattc tggcacgatg    1080
gttcgagcag tgggtgatga gatgggcact gtccgagtag ccagcaccat gactgatgga    1140
gccaatacta tgattgagca cgatgacacg ttgccatcac aactgggcac catggtgatc    1200
aatgcagagg atgaggaaga ggaaggaact atgaaaagaa gggatgagac catgcagcct    1260
gcgaaaccat cctttcttga atattttgaa caaaagaaa aggaaaacca gatcaacagc    1320
tttggcaaga gtgtacctgg tccactgaaa aattcttcag attggaaaat accacaggat    1380
ggagactacg agtttcttaa gagttggaca gtggaggacc ttcagaagag gctcttggcc    1440
ctggacccca tgatggagca ggagattgaa agatccggc agaagtacca gtccaagcgg    1500
```

```
cagcccatcc tggatgccat agaggctaag aagagacggc aacaaaactt ctgagcaagg   1560
ccaggctgtg agggccccag ctccacccag gctttgggtg aattctggat ggcttgcctc   1620
atgtttgtta gccagcactt ctgctctgtc gtctctccac agcacctttg tgaactcagg   1680
aatgtgcgcc agtgggaagg gctctcttga cagtcagcgt gccatcttga tgtgtgtatg   1740
tacattggtc aggtatatta tctcaaagga tttatattgg cgcttttaac tcagagtttt   1800 aaacccagg aacagagact cctagttgag tgatagctgg gaaagtttta cattgtctgt    1860
ttttcttctc ccaatagctt tcaattgttc tttctggaag acttttaaaa aaatataaat   1920
atgcatatat atatataaat tataaataga ttccccacgc agtgtggtgg catctctgta   1980
caggtacagt tttaaacggt ttgcctcttt tctgtaagat tatggtactg tggaacatga   2040
gggcagagga caccgggagg ctgttagggg gtcactgaat cccaggagcc aacctccccc   2100
tttgcagggc tgcatttaaa aattaggttt gggacagttc ttgtaccgtg gtttcagcct   2160
tgtgtggtca tcactggctt ctggagctat tggtgatgtc caagggaaag ctttgagagt   2220
ttatgtttac tctttgagtc ccaggagaag cctggcaccc tctttgcaaa ttggcctttg   2280
ctctttcaat gcctttcatc catctccact ctctcaactg cctaaagtca cagcacagat   2340
actgcccagt gccttaagag gagacatgat ctctaccagg gactctcagc aaacacggga   2400
ctgtgttcag tccacaaagg aaaagcgttt ttgaagctct cattgttcat gtaaaaatca   2460
tacacgtggc atgttgctcc acattcctta cacacagggg tagaggggat tgcttttgtg   2520
acccacgttc aaatatgtga ctgttttctt ttctctttta ctgctaagca gcctggaaag   2580
gataaatgaa tattagacta agatttgttt tccaggaggc tcaatctgaa cacacagaat   2640
gtcagagctg gaagggacta tagagatcat ctgatctgat cctcttgtac ggatgatcgc   2700
aaaactgagg tgtagagagg ggaatggcca aaatcacaaa gcaagttagc gttaagagct   2760
gagactagaa ttcagggtcc tcactcccag gccaccgaac catgcagccc tttcttggg    2820 ggaagagacc tgtgtcagtc ttggttaatt gttccaggga accttgctaa cagaaacttg   2880
ctcttgcctt ggctcttcag tagatgacct ggctgtaaag agattccctg gacgagccag   2940
atcattcagt ttcagcgagt ccttgagctc cacaacatct accagatata gcagacaagc   3000
acccatggag gcaggtttcg ggcctgaagc agatcagagg gctttgcaaa agacagcata   3060
gagccatctt cctgcaactt tacctctttc cctcagatgg ggagccatga ctgggttgca   3120
cctcaggata ctgtaatttg actccataat tgcttttgct cctgaaacct gggaatcaat   3180
ggaaaggcag ggaatgtgcc tcttctgtgg ccagattctg ttatttgcaa ttaaagcaag   3240 ttttttaaaaa atgcaagagg cagttgttag tcttcagggc ttggcaactg aaatagctat   3300
gtggcggata cggaaaacag aggacaattt gaggatcttg ctggaataat aaatgacagc   3360
taccatttgt tgagcaccta ttatatatca ggcactgagc tgggtaggct ctaaacttca   3420
caataaccct gtgacttaac tactttatct ccatttgta gttgaagaaa taagttcaga    3480
gagaaagatt ccttcccaag gtcatgcagc tagtaaatga tagaatcagg attcatagca   3540
tcactatagg gggtcaatat ttacacaaaa aaggaaagtc acaagcctgt ttaaaatgaa   3600
gtgaccacct tttcttgcat agactaaata actcgaactg gcattttag gttggaagaa   3660 cagctgaatt agtagttaag tctgatagcc aagtaagttt taaaaaccaa agcatccagg   3720
atgcacaccc ctgcaccatt tgctgtgcga attaatagtt ctgtctctct ctctcttct    3780 ttttctttt tattctttga gatggatttt cgctcttgtc gcccaggctg gagtacaatg    3840
```

```
gcacgatctt ggctcactgc aacctccgcc tcccgggttc aagcgattct tctgctggga    3900
ttacagcata tgccaccatg cccagattat ttttttgtat ttgtagtaga gacggggttt    3960
caccatgtca gtcaggctgg tcttgaactc ctgacctcag gtgatccacc cgcctcagcc    4020
tcccacactg ctgggattac aggcatgagc caccgctcct ggcctctctt tcttttttaa    4080
acaaagaact ttgcacttgg ccagagagga ggagaaagcc cattttctcc cttcctaagc    4140
tagatccaaa taaagaaag ttcagttttc ccccataact attcttgggt catgaacttt     4200
gatctggagt ttgttttgtt tcaggaatgt gtgcacccag cttgctgatc aacaaagtc     4260
tattgcttac cagtctagct tgatgaagcc ttttggccag aagtcaattt gttttggatc    4320
agagaaattt cctgacaagg tatatttgtt ttctagtgac agaaaggcaa aggaacaagt    4380
cctagttgtt gttgttgttg ttgaatacta aatttaagat atgtcagctt gctttcaatg    4440
agccttgggc ttctgttatt gcttgagcat ttggaactcg agcttccaga gaaatttgag    4500
gtcctcgctt gttctctgcc ttcaagaaac aatgacctga ttctgtcttt aaaaaaaaaa    4560
atctcagaat tcttttttg tttgtgtttt ttttttttt tgagacagag tctcactctg       4620
ttgcccaggc tggagtgcag tggcgccatc tcggctcact gcaacctccg cctcccaggt    4680
tcaagcaatt ctcctgcctc agcctcccag gtagctgcca ctacaggtgc tgcaccacca    4740
cgcccggcta atttttgtat ttttagtaga cagggtttt caccatatta gccaggtggg      4800
tcttgaactc ctgaccttgt gatccacccg cctcggcctc ccaaagtgct gggattacag    4860
gcgtgagcca ccttgcctgg ccaaaaatct cagaattctt taagactgtt ttaattgctc    4920
catcagtaat tttgaagcac tttccttttt ttttttttt cccctttttg tcccttccc      4980
caagccacca attggatgga tgaatgtttg acggggaaga ggaagggtag gaggatgcat    5040
ggatgagtgg atgagtggat cgatggatgt attgataaat agatagaacc agtcatctga    5100
agcaacttaa gaattgtagc cttgactcct tgagactgta gatttcgatc caggaaacat    5160
ttatttagca cctgccagat gccagaaatt tataccattt aaaactcagt aagtctttta    5220
aatatcagga aggagagaag cgacatcatg atacatccta tgggtattaa aaagccaata    5280
gaatattatg ataatttta tgctaataaa tttaacaact tcaacatcat aaacaaattc      5340
cttgaaaaat aaaaagtacc aaaattcatt caagaagaaa tagataccag cctgagcaac    5400
atggcaaaat cccatctcta caaaacatca aaaaaaaaa aaattagtcg ggcatggtgg     5460
tgcacacctg taatcccagc ttgtcaggag gctgaagtgg gaggatcacc tgagcccagg    5520
gaggtcaagg atgcagtgag ccatggtctc accactgcac tctagcctgg gtgacagaat    5580
gagaccccgt ctcaaaaaaa aagaagaagt agataatctg aatagcccta tatctataga    5640
aacttaatag tgctgggaga tataggtatt attatcctca ttttacagat gtgaaaattg    5700
aggctcagag aagtaaagtc tattgctcaa ggtcatgtgg ctagaatatg gcagagccat    5760
gattcagatc caggtcttct gattcttatt ccagtgtcct ttctagcata ccatgttgcc    5820
tctaaagatt gcagctcctt atttactaga aaattgttcc tgcccaatct acatctccac    5880
ctcaccccat cttttcttaa gcactatgtt tgtgttttta tcagtattat attcattgtc    5940
tttggaatac atgttcttgt ttgtgtttgg aaaaaaaatc tcttttacca gcttgcactc    6000
ggaccaactt ggaaaaaaaa aagcttaaat gttttttgcta tgtacagttt aaaaatgtga   6060
agtttgtagc tttaactttt tgtaagaaaa tctaataaca ctggcttaag tgctgacttg    6120
aaatgctatt ttgtaaggtt tggatgtaag taatcaattg aggtcagcag tttgtatgag    6180
acatagcttc ctccattgcc cccactcctt tttttctttt taagtttgag atgcttcctg    6240
```

-continued

```
tgtttttatg ttagaattgt tgttctcctt cttttcttct tcctataacct catcacgttt    6300 gttttaaata aactgtcctt tggaccacaa aaaaaaaaaa aaaa                     6344
```

<210> SEQ ID NO 34
<211> LENGTH: 487
<212> TYPE: PRT
<213> ORGANISM: Homo sapiens

<400> SEQUENCE: 34

```
Met Glu Thr Val Gln Leu Arg Asn Pro Pro Arg Arg Gln Leu Lys Lys
1               5                   10                  15

Leu Asp Glu Asp Ser Leu Thr Lys Gln Pro Glu Glu Val Phe Asp Val
            20                  25                  30

Leu Glu Lys Leu Gly Glu Gly Ser Tyr Gly Ser Val Tyr Lys Ala Ile
        35                  40                  45

His Lys Glu Thr Gly Gln Ile Val Ala Ile Lys Gln Val Pro Val Glu
    50                  55                  60

Ser Asp Leu Gln Glu Ile Ile Lys Glu Ile Ser Ile Met Gln Gln Cys
65                  70                  75                  80

Asp Ser Pro His Val Val Lys Tyr Tyr Gly Ser Tyr Phe Lys Asn Thr
                85                  90                  95

Asp Leu Trp Ile Val Met Glu Tyr Cys Gly Ala Gly Ser Val Ser Asp
            100                 105                 110

Ile Ile Arg Leu Arg Asn Lys Thr Leu Thr Glu Asp Glu Ile Ala Thr
        115                 120                 125

Ile Leu Gln Ser Thr Leu Lys Gly Leu Glu Tyr Leu His Phe Met Arg
    130                 135                 140

Lys Ile His Arg Asp Ile Lys Ala Gly Asn Ile Leu Leu Asn Thr Glu
145                 150                 155                 160

Gly His Ala Lys Leu Ala Asp Phe Gly Val Ala Gly Gln Leu Thr Asp
                165                 170                 175

Thr Met Ala Lys Arg Asn Thr Val Ile Gly Thr Pro Phe Trp Met Ala
            180                 185                 190

Pro Glu Val Ile Gln Glu Ile Gly Tyr Asn Cys Val Ala Asp Ile Trp
        195                 200                 205

Ser Leu Gly Ile Thr Ala Ile Glu Met Ala Glu Gly Lys Pro Pro Tyr
    210                 215                 220

Ala Asp Ile His Pro Met Arg Ala Ile Phe Met Ile Pro Thr Asn Pro
225                 230                 235                 240

Pro Pro Thr Phe Arg Lys Pro Glu Leu Trp Ser Asp Asn Phe Thr Asp
                245                 250                 255

Phe Val Lys Gln Cys Leu Val Lys Ser Pro Glu Gln Arg Ala Thr Ala
            260                 265                 270

Thr Gln Leu Leu Gln His Pro Phe Val Arg Ser Ala Lys Gly Val Ser
        275                 280                 285

Ile Leu Arg Asp Leu Ile Asn Glu Ala Met Asp Val Lys Leu Lys Arg
    290                 295                 300

Gln Glu Ser Gln Gln Arg Glu Val Asp Gln Asp Glu Glu Asn Ser
305                 310                 315                 320

Glu Glu Asp Glu Met Asp Ser Gly Thr Met Val Arg Ala Val Gly Asp
                325                 330                 335

Glu Met Gly Thr Val Arg Val Ala Ser Thr Met Thr Asp Gly Ala Asn
            340                 345                 350
```

Thr Met Ile Glu His Asp Asp Thr Leu Pro Ser Gln Leu Gly Thr Met
            355                 360                 365

Val Ile Asn Ala Glu Asp Glu Glu Glu Gly Thr Met Lys Arg Arg
    370                 375                 380

Asp Glu Thr Met Gln Pro Ala Lys Pro Ser Phe Leu Glu Tyr Phe Glu
385                 390                 395                 400

Gln Lys Glu Lys Glu Asn Gln Ile Asn Ser Phe Gly Lys Ser Val Pro
                405                 410                 415

Gly Pro Leu Lys Asn Ser Ser Asp Trp Lys Ile Pro Gln Asp Gly Asp
                420                 425                 430

Tyr Glu Phe Leu Lys Ser Trp Thr Val Glu Asp Leu Gln Lys Arg Leu
            435                 440                 445

Leu Ala Leu Asp Pro Met Met Glu Gln Glu Ile Glu Glu Ile Arg Gln
    450                 455                 460

Lys Tyr Gln Ser Lys Arg Gln Pro Ile Leu Asp Ala Ile Glu Ala Lys
465                 470                 475                 480

Lys Arg Arg Gln Gln Asn Phe
                485

<210> SEQ ID NO 35
<211> LENGTH: 2828
<212> TYPE: DNA
<213> ORGANISM: Homo sapiens

<400> SEQUENCE: 35

```
ccgcggagtt acgggaaagt tggtccgagt tcccagagtt tccctctgtg gtgccctagg      60
ctcggccggc cggtgccccg gctccttttcc tcctttcggc cttcgccgtc caccaggtcc    120
ctctctctgt ccccggccgc catggagcag ccgccggcgc ctaagagtaa actaaaaaag    180
ctgagtgaag acagtttgac taagcagcct gaagaagttt ttgatgtatt agagaagctt    240
ggagaagggt cttatggaag tgtatttaaa gcaatacaca aggaatccgg tcaagttgtc    300
gcaattaaac aagtacctgt tgaatcagat cttcaggaaa taatcaaaga aatttccata    360
atgcagcaat gtgacagccc atatgttgta agtactatg gcagttattt taagaataca    420
gacctctgga ttgttatgga gtactgtggc gctggctctg tctcagacat aattagatta    480
cgaaacaaga cattaataga agatgaaatt gcaaccattc ttaaatctac attgaaagga    540
ctagaatatt tgcactttat gagaaaaata cacagagata taaaagctgg aaatattctc    600
ctcaatacag aaggacatgc aaaattggca gattttggag tggctggtca gttaacagat    660
acaatggcaa aacgcaatac tgtaatagga actccatttt ggatggctcc tgaggtgatt    720
caagaaatag gctataactg tgtggccgac atctggtccc ttggcattac ttctatagaa    780
atggctgaag aaaacctcc ttatgctgat atacatccaa tgagggctat ttttatgatt    840
cccacaaatc caccaccaac attcagaaag ccagaacttt ggtccgatga tttcaccgat    900
tttgttaaaa agtgtttggt gaagaatcct gagcagagag ctactgcaac acaactttta    960
cagcatcctt ttatcaagaa tgccaaacct gtatcaatat aagagacct gatcacagaa   1020
gctatggaga tcaaagctaa agacatgag gaacagcaac gagaattgga agaggaagaa   1080
gaaaattcgg atgaagatga gctggatgcc cacaccatgg tgaagactag tgtggagagt   1140
gtgggcacca tgcgggccac aagcacgatg agtgaagggg cccagaccat gattgaacat   1200
aatagcacga tgttggaatc cgacttgggg accatggtga taaacagtga ggatgaggaa   1260
gaagaagatg gaactatgaa aagaaatgca acctcaccac aagtacaaag accatctttc   1320
```

-continued

| | |
|---|---|
| atggactact tgataagca agacttcaag aataagagtc acgaaaactg taatcagaac | 1380 |
| atgcatgaac ccttccctat gtccaaaaac gttttcctg ataactggaa agttcctcaa | 1440 |
| gatggagact ttgactttt gaaaaatcta agtttagaag aactacagat gcggttaaaa | 1500 |
| gcactggacc ccatgatgga acgggagata aagaacttc gtcagagata cactgcgaaa | 1560 |
| agacagccca ttctggatgc gatggatgca agaaaagaa ggcagcaaaa cttttgagtc | 1620 |
| taatttcctc tctgttttta actattctgg agaccaagaa accactagga attgaaggaa | 1680 |
| tatttggata tttttaatcc taagattttg ccctacaatt aggcagaggt caaaaagtga | 1740 |
| caatggtaca tgcccaggta aattcccaaa aggcagaatt gacagttgta tctgctgtgc | 1800 |
| attcactcta agatgaggag aacaaaagaa gtgtattctc ttgttctgtc agctgcatac | 1860 |
| cagtaataaa actgttatga aatggatttt caaggtctct aaaccttgaa atccaaagc | 1920 |
| tattgttgca ttgtacagca ctgaagggct ttatgttaca atattcttta ttcctatcta | 1980 |
| gtatactagg ctatttattg tatcccctta ggtaaactta tttattatg ctattttgct | 2040 |
| ttgtttcatt ttttaaggac aagatcagga tagctttggt gaaggtaggg tcatattaat | 2100 |
| atgatgataa tgtgcaacca atttatactt tctgcaggga gctatggggt acattccttg | 2160 |
| atttccagga tagttttca aataggaaag caataatggc agtagttctc aaatgggcta | 2220 |
| ggcctttttt atattgaagc ataattcca ttttaccct ttgaaatttt gttttttga | 2280 |
| tttttgatgt ttggtacaaa tagaactata tatatttagg taaaatagat ctatcgtgtt | 2340 |
| taaaaccaaa gaaatcaatg gaaccccttgc acaaaaagt gtgataaata tttttaaata | 2400 |
| aaaacttaat acaaatgtaa tttgttaata ttgtttcatg ttttatgtgt agatctaata | 2460 |
| gctgaactga ttcaaactgt aataagctca tcaatttcat ttctatgaaa atgtgctctg | 2520 |
| ttgtcacagg atgtttctgt tgattttat catttcctgg gaattggtaa acatcatgtt | 2580 |
| cctgatgata acccagtagc aaaaacattt gtactgagtg gtacaagcct tggggactga | 2640 |
| aaaaaaaaag attaaaacca ttaaaaagaa actcattttt acgctgaatg aacatttata | 2700 |
| tgattgcatt gggaccagtc atttcctaag ctacatatgg ccatcttgac agtgttttt | 2760 |
| cttttgtgtg tttaattatt atgtgtaaat cataaagaca aataaatttc actgtgccac | 2820 |
| ccagcata | 2828 |

<210> SEQ ID NO 36
<211> LENGTH: 491
<212> TYPE: PRT
<213> ORGANISM: Homo sapiens

<400> SEQUENCE: 36

Met Glu Gln Pro Pro Ala Pro Lys Ser Lys Leu Lys Lys Leu Ser Glu
1               5                   10                  15

Asp Ser Leu Thr Lys Gln Pro Glu Glu Val Phe Asp Val Leu Glu Lys
            20                  25                  30

Leu Gly Glu Gly Ser Tyr Gly Ser Val Phe Lys Ala Ile His Lys Glu
        35                  40                  45

Ser Gly Gln Val Val Ala Ile Lys Gln Val Pro Val Glu Ser Asp Leu
    50                  55                  60

Gln Glu Ile Ile Lys Glu Ile Ser Ile Met Gln Cys Asp Ser Pro
65                  70                  75                  80

Tyr Val Val Lys Tyr Tyr Gly Ser Tyr Phe Lys Asn Thr Asp Leu Trp
                85                  90                  95

Ile Val Met Glu Tyr Cys Gly Ala Gly Ser Val Ser Asp Ile Ile Arg

```
            100                 105                 110
Leu Arg Asn Lys Thr Leu Ile Glu Asp Glu Ile Ala Thr Ile Leu Lys
            115                 120                 125

Ser Thr Leu Lys Gly Leu Glu Tyr Leu His Phe Met Arg Lys Ile His
    130                 135                 140

Arg Asp Ile Lys Ala Gly Asn Ile Leu Leu Asn Thr Glu Gly His Ala
145                 150                 155                 160

Lys Leu Ala Asp Phe Gly Val Ala Gly Gln Leu Thr Asp Thr Met Ala
                165                 170                 175

Lys Arg Asn Thr Val Ile Gly Thr Pro Phe Trp Met Ala Pro Glu Val
            180                 185                 190

Ile Gln Glu Ile Gly Tyr Asn Cys Val Ala Asp Ile Trp Ser Leu Gly
        195                 200                 205

Ile Thr Ser Ile Glu Met Ala Glu Gly Lys Pro Pro Tyr Ala Asp Ile
    210                 215                 220

His Pro Met Arg Ala Ile Phe Met Ile Pro Thr Asn Pro Pro Pro Thr
225                 230                 235                 240

Phe Arg Lys Pro Glu Leu Trp Ser Asp Asp Phe Thr Asp Phe Val Lys
                245                 250                 255

Lys Cys Leu Val Lys Asn Pro Glu Gln Arg Ala Thr Ala Thr Gln Leu
            260                 265                 270

Leu Gln His Pro Phe Ile Lys Asn Ala Lys Pro Val Ser Ile Leu Arg
        275                 280                 285

Asp Leu Ile Thr Glu Ala Met Glu Ile Lys Ala Lys Arg His Glu Glu
    290                 295                 300

Gln Gln Arg Glu Leu Glu Glu Glu Glu Asn Ser Asp Glu Asp Glu
305                 310                 315                 320

Leu Asp Ser His Thr Met Val Lys Thr Ser Val Glu Ser Val Gly Thr
                325                 330                 335

Met Arg Ala Thr Ser Thr Met Ser Glu Gly Ala Gln Thr Met Ile Glu
            340                 345                 350

His Asn Ser Thr Met Leu Glu Ser Asp Leu Gly Thr Met Val Ile Asn
        355                 360                 365

Ser Glu Asp Glu Glu Glu Asp Gly Thr Met Lys Arg Asn Ala Thr
    370                 375                 380

Ser Pro Gln Val Gln Arg Pro Ser Phe Met Asp Tyr Phe Asp Lys Gln
385                 390                 395                 400

Asp Phe Lys Asn Lys Ser His Glu Asn Cys Asn Gln Asn Met His Glu
                405                 410                 415

Pro Phe Pro Met Ser Lys Asn Val Phe Pro Asp Asn Trp Lys Val Pro
            420                 425                 430

Gln Asp Gly Asp Phe Asp Phe Leu Lys Asn Leu Ser Leu Glu Glu Leu
        435                 440                 445

Gln Met Arg Leu Lys Ala Leu Asp Pro Met Met Glu Arg Glu Ile Glu
    450                 455                 460

Glu Leu Arg Gln Arg Tyr Thr Ala Lys Arg Gln Pro Ile Leu Asp Ala
465                 470                 475                 480

Met Asp Ala Lys Lys Arg Arg Gln Gln Asn Phe
                485                 490

<210> SEQ ID NO 37
<211> LENGTH: 5388
<212> TYPE: DNA
<213> ORGANISM: Homo sapiens
```

<400> SEQUENCE: 37

```
aaaatgttgg agatctgcct gaagctggtg ggctgcaaat ccaagaaggg gctgtcctcg      60
tcctccagct gttatctgga agaagccctt cagcggccag tagcatctga ctttgagcct     120
cagggtctga gtgaagccgc tcgttggaac tccaaggaaa accttctcgc tggacccagt     180
gaaaatgacc ccaaccttt cgttgcactg tatgattttg tggccagtgg agataacact      240
ctaagcataa ctaaaggtga aaagctccgg gtcttaggct ataatcacaa tggggaatgg     300
tgtgaagccc aaaccaaaaa tggccaaggc tgggtcccaa gcaactacat cacgccagtc     360
aacagtctgg agaaacactc ctggtaccat gggcctgtgt cccgcaatgc cgctgagtat     420
ctgctgagca gcgggatcaa tggcagcttc ttggtgcgtg agagtgagag cagtcctggc     480
cagaggtcca tctcgctgag atacgaaggg agggtgtacc attacaggat caacactgct     540
tctgatggca agctctacgt ctcctccgag agccgcttca cacccctggc cgagttggtt     600
catcatcatt caacggtggc cgacgggctc atcaccacgc tccattatcc agccccaaag     660
cgcaacaagc ccactgtcta tggtgtgtcc cccaactacg acaagtggga gatggaacgc     720
acggacatca ccatgaagca caagctgggc ggggccagt acggggaggt gtacgagggc      780
gtgtggaaga atacagcct gacggtggcc gtgaagacct tgaaggagga caccatggag      840
gtggaagagt tcttgaaaga agctgcagtc atgaaagaga tcaaacaccc taacctggtg     900
cagctccttg gggtctgcac ccgggagccc ccgttctata tcatcactga gttcatgacc     960
tacgggaacc tcctggacta cctgagggag tgcaaccggc aggaggtgaa cgccgtggtg    1020
ctgctgtaca tggccactca gatctcgtca gccatggagt acctggagaa gaaaaacttc    1080
atccacagag atcttgctgc ccgaaactgc ctggtagggg agaaccactt ggtgaaggta    1140
gctgattttg gcctgagcag gttgatgaca ggggacacct acacagccca tgctggagcc    1200
aagttcccca tcaaatggac tgcacccgag agcctggcct acaacaagtt ctccatcaag    1260
tccgacgtct gggcatttgg agtattgctt tgggaaattg ctacctatgg catgtcccct    1320
tacccgggaa ttgacctgtc ccaggtgtat gagctgctag agaaggacta ccgcatggag    1380
cgcccagaag gctgcccaga aaggtctat gaactcatgc gagcatgttg gcagtggaat    1440
ccctctgacc ggccctcctt tgctgaaatc caccaagcct ttgaaacaat gttccaggaa    1500
tccagtatct cagacgaagt ggaaaaggag ctggggaaac aaggcgtccg tggggctgtg    1560
agtaccttgc tgcaggcccc agagctgccc accaagacga ggacctccag gagagctgca    1620
gagcacagag acaccactga cgtgcctgag atgcctcact ccaagggcca gggagagagc    1680
gatcctctgg accatgagcc tgccgtgtct ccattgctcc ctcgaaaaga gcgaggtccc    1740
ccggagggcg gcctgaatga agatgagcgc cttctcccca agacaaaaa gaccaacttg    1800
ttcagcgcct tgatcaagaa gaagaagaag acagccccaa ccctccaa acgcagcagc     1860
tccttccggg agatggacgg ccagccgag cgcagagggg ccggcgagga gagggccga     1920
gacatcagca acggggcact ggctttcacc cccttggaca cagctgaccc agccaagtcc    1980
ccaaagccca gcaatgggc tgggtcccca aatggagccc tcgggagtc cgggggctca     2040
ggcttccggt ctccccacct gtggaagaag tccagcacgc tgaccagcag ccgcctagcc    2100
accggcgagg aggagggcgg tggcagctcc agcaagcgct tcctgcgctc ttgctccgcc    2160
tcctgcgttc cccatgggc caaggacacg gagtggaggt cagtcacgct gcctcgggac    2220
ttgcagtcca cggaagaca gttttgactcg tccacatttg gagggcacaa aagtgagaag    2280
```

-continued

```
ccggctctgc ctcggaagag ggcaggggag aacaggtctg accaggtgac ccgaggcaca    2340
gtaacgcctc cccccaggct ggtgaaaaag aatgaggaag ctgctgatga ggtcttcaaa    2400
gacatcatgg agtccagccc gggctccagc ccgcccaacc tgactccaaa acccctccgg    2460
cggcaggtca ccgtggcccc tgcctcgggc ctcccccaca aggaagaagc tggaaagggc    2520
agtgccttag ggaccnctgc tgcagctgag ccagtgaccc ccaccagcaa agcaggctca    2580
ggtgcaccag ggggcaccag caagggcccc gccgaggagt ccagagtgag gaggcacaag    2640
cactcctctg agtcgccagg gagggacaag gggaaattgt ccaggctcaa acctgccccg    2700
ccgcccccac cagcagcctc tgcagggaag gctggaggaa agccctcgca gagcccgagc    2760
caggaggcgg ccggggaggc agtcctgggc gcaaagacaa aagccacgag tctggttgat    2820
gctgtgaaca gtgacgctgc caagcccagc cagccgggag agggcctcaa aaagcccgtg    2880 ctccccggcca ctccaaagcc acagtccgcc aagccgtcgg gaccccat cagcccagcc    2940 cccgttccct ccacgttgcc atcagcatcc tcggccctgg caggggacca gccgtcttcc    3000
accgccttca tccctctcat atcaacccga gtgtctcttc ggaaaacccg ccagcctcca    3060
gagcggatcg ccagcggcgc catcaccaag ggcgtggtcc tggacagcac cgaggcgctg    3120
tgcctcgcca tctctaggaa ctccgagcag atggccagcc acagcgcagt gctggaggcc    3180
ggcaaaaacc tctacacgtt ctgcgtgagc tatgtggatt ccatccagca aatgaggaac    3240
aagtttgcct tccgagaggc catcaacaaa ctggagaata atctccggga gcttcagatc    3300
tgcccggcga cagcaggcag tggtccagcg ccactcagg acttcagcaa gctcctcagt    3360
tcggtgaagg aaatcagtga catagtgcag aggtagcagc agtcagggt caggtgtcag    3420 gcccgtcgga gctgcctgca gcacatgcgg gctcgcccat accgtgaca gtggctgaca    3480 agggactagt gagtcagcac cttggcccag gagctctgcg ccaggcagag ctgagggccc    3540
tgtggagtcc agctctacta cctacgtttg caccgcctgc cctccgcac cttcctcctc    3600 cccgctccgt ctctgtcctc gaatttatc tgtggagttc ctgctccgtg gactgcagtc    3660
ggcatgccag gacccgccag ccccgctccc acctagtgcc ccagactgag ctctccaggc    3720
caggtgggaa cggctgatgt ggactgtctt tttcattttt ttctctctgg agcccctcct    3780
cccccggctg ggcctccttc ttccacttct ccaagaatgg aagcctgaac tgaggccttg    3840
tgtgtcaggc cctctgcctg cactccctgg ccttgcccgt cgtgtgctga agacatgttt    3900
caagaaccgc atttcgggaa gggcatgcac gggcatgcac acggctggtc actctgccct    3960
ctgctgctgc ccggggtggg gtgcactcgc catttcctca cgtgcaggac agctcttgat    4020
ttgggtggaa acagggtgc taaagccaac cagcctttgg gtcctgggca ggtgggagct    4080
gaaaaggatc gaggcatggg gcatgtcctt tccatctgtc cacatcccca gagcccagct    4140
cttgctctct tgtgacgtgc actgtgaatc ctggcaagaa agcttgagtc tcaagggtgg    4200
caggtcactg tcactgccga catccctccc ccagcagaat ggaggcaggg gacaagggag    4260
gcagtggcta gtggggtgaa cagctggtgc caaatagccc cagactgggc ccaggcaggt    4320
ctgcaagggc ccagagtgaa ccgtcctttc acacatctgg gtgccctgaa agggcccttc    4380
ccctccccca ctcctctaag acaaagtaga ttcttacaag gcccttttcct ttggaacaag    4440 acagccttca cttttctgag ttcttgaagc atttcaaagc cctgcctctg tgtagccgcc    4500
ctgagagaga atagagctgc cactgggcac ctgcgcacag gtgggaggaa agggcctggc    4560
cagtcctggt cctggctgca ctcttgaact gggcgaatgc cttatttaat taccgtgagt    4620
gacatagcct catgttctgt gggggtcatc agggagggtt aggaaaacca caaacggagc    4680
```

-continued

```
ccctgaaagc ctcacgtatt tcacagagca cgcctgccat cttctccccg aggctgcccc    4740
aggccggagc ccagatacgg gggctgtgac tctgggcagg gacccggggt ctcctggacc    4800
ttgacagagc agctaactcc gagagcagtg ggcaggtggc cgcccctgag gcttcacgcc    4860
gggagaagcc accttcccac cccttcatac cgcctcgtgc cagcagcctc gcacaggccc    4920
tagctttacg ctcatcacct aaacttgtac tttattttc tgatagaaat ggtttcctct     4980
ggatcgtttt atgcggttct tacagcacat cacctctttg cccccgacgg ctgtgacgca    5040
gccggaggga ggcactagtc accgacagcg gccttgaaga cagagcaaag cgcccaccca    5100
ggtcccccga ctgcctgtct ccatgaggta ctggtccctt ccttttgtta acgtgatgtg    5160
ccactatatt ttacacgtat ctcttggtat gcatctttta tagacgctct tttctaagtg    5220
gcgtgtgcat agcgtcctgc cctgcccct cggggggctg tggtggctcc ccctctgctt     5280
ctcggggtcc agtgcatttt gtttctgtat atgattctct gtggtttttt ttgaatccaa    5340
atctgtcctc tgtagtattt tttaaataaa tcagtgttta cattagaa                 5388
```

<210> SEQ ID NO 38
<211> LENGTH: 1130
<212> TYPE: PRT
<213> ORGANISM: Homo sapiens

<400> SEQUENCE: 38

```
Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
```

```
                245                 250                 255
Tyr Glu Gly Val Trp Lys Lys Tyr Ser Leu Thr Val Ala Val Lys Thr
                260                 265                 270
Leu Lys Glu Asp Thr Met Glu Val Glu Phe Leu Lys Glu Ala Ala
            275                 280                 285
Val Met Lys Glu Ile Lys His Pro Asn Leu Val Gln Leu Leu Gly Val
        290                 295                 300
Cys Thr Arg Glu Pro Pro Phe Tyr Ile Ile Thr Glu Phe Met Thr Tyr
305                 310                 315                 320
Gly Asn Leu Leu Asp Tyr Leu Arg Glu Cys Asn Arg Gln Glu Val Asn
                325                 330                 335
Ala Val Val Leu Leu Tyr Met Ala Thr Gln Ile Ser Ser Ala Met Glu
            340                 345                 350
Tyr Leu Glu Lys Lys Asn Phe Ile His Arg Asp Leu Ala Ala Arg Asn
            355                 360                 365
Cys Leu Val Gly Glu Asn His Leu Val Lys Val Ala Asp Phe Gly Leu
        370                 375                 380
Ser Arg Leu Met Thr Gly Asp Thr Tyr Thr Ala His Ala Gly Ala Lys
385                 390                 395                 400
Phe Pro Ile Lys Trp Thr Ala Pro Glu Ser Leu Ala Tyr Asn Lys Phe
                405                 410                 415
Ser Ile Lys Ser Asp Val Trp Ala Phe Gly Val Leu Leu Trp Glu Ile
            420                 425                 430
Ala Thr Tyr Gly Met Ser Pro Tyr Pro Gly Ile Asp Leu Ser Gln Val
            435                 440                 445
Tyr Glu Leu Leu Glu Lys Asp Tyr Arg Met Glu Arg Pro Glu Gly Cys
        450                 455                 460
Pro Glu Lys Val Tyr Glu Leu Met Arg Ala Cys Trp Gln Trp Asn Pro
465                 470                 475                 480
Ser Asp Arg Pro Ser Phe Ala Glu Ile His Gln Ala Phe Glu Thr Met
                485                 490                 495
Phe Gln Glu Ser Ser Ile Ser Asp Glu Val Glu Lys Glu Leu Gly Lys
            500                 505                 510
Gln Gly Val Arg Gly Ala Val Ser Thr Leu Leu Gln Ala Pro Glu Leu
            515                 520                 525
Pro Thr Lys Thr Arg Thr Ser Arg Arg Ala Ala Glu His Arg Asp Thr
        530                 535                 540
Thr Asp Val Pro Glu Met Pro His Ser Lys Gly Gln Gly Glu Ser Asp
545                 550                 555                 560
Pro Leu Asp His Glu Pro Ala Val Ser Pro Leu Leu Pro Arg Lys Glu
                565                 570                 575
Arg Gly Pro Pro Glu Gly Gly Leu Asn Glu Asp Glu Arg Leu Leu Pro
            580                 585                 590
Lys Asp Lys Lys Thr Asn Leu Phe Ser Ala Leu Ile Lys Lys Lys Lys
            595                 600                 605
Lys Thr Ala Pro Thr Pro Pro Lys Arg Ser Ser Ser Phe Arg Glu Met
        610                 615                 620
Asp Gly Gln Pro Glu Arg Arg Gly Ala Gly Glu Glu Gly Arg Asp
625                 630                 635                 640
Ile Ser Asn Gly Ala Leu Ala Phe Thr Pro Leu Asp Thr Ala Asp Pro
                645                 650                 655
Ala Lys Ser Pro Lys Pro Ser Asn Gly Ala Gly Val Pro Asn Gly Ala
            660                 665                 670
```

```
Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
        690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
        770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Gly Lys Gly Ser Ala Leu Gly Thr Pro Ala Ala Ala
        835                 840                 845

Glu Pro Val Thr Pro Thr Ser Lys Ala Gly Ser Gly Ala Pro Gly Gly
        850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Ala Ala Ser Ala Gly Lys Ala Gly Gly
            900                 905                 910

Lys Pro Ser Gln Ser Pro Ser Gln Glu Ala Ala Gly Glu Ala Val Leu
        915                 920                 925

Gly Ala Lys Thr Lys Ala Thr Ser Leu Val Asp Ala Val Asn Ser Asp
        930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ala Leu
            980                 985                 990

Ala Gly Asp Gln Pro Ser Ser Thr Ala Phe Ile Pro Leu Ile Ser Thr
        995                 1000                1005

Arg Val Ser Leu Arg Lys Thr Arg Gln Pro Pro Glu Arg Ile Ala
        1010                1015                1020

Ser Gly Ala Ile Thr Lys Gly Val Val Leu Asp Ser Thr Glu Ala
        1025                1030                1035

Leu Cys Leu Ala Ile Ser Arg Asn Ser Glu Gln Met Ala Ser His
        1040                1045                1050

Ser Ala Val Leu Glu Ala Gly Lys Asn Leu Tyr Thr Phe Cys Val
        1055                1060                1065

Ser Tyr Val Asp Ser Ile Gln Gln Met Arg Asn Lys Phe Ala Phe
        1070                1075                1080
```

```
Arg Glu Ala Ile Asn Lys Leu Glu Asn Asn Leu Arg Glu Leu Gln
    1085            1090                1095

Ile Cys Pro Ala Thr Ala Gly Ser Gly Pro Ala Ala Thr Gln Asp
    1100            1105                1110

Phe Ser Lys Leu Leu Ser Ser Val Lys Glu Ile Ser Asp Ile Val
    1115            1120                1125

Gln Arg
    1130
```

TARGETS IN MULTIPLE MYELOMA AND OTHER DISORDERS

CLAIM FOR PRIORITY

This application claims priority under 35 USC 371 to International Application No. PCT/IB2013/059908, filed on Nov. 5, 2013, which claims priority to U.S. Provisional Patent Application No. 61/722,518, which was filed on Nov. 5, 2012, each of which is hereby incorporated by reference in its entirety.

FIELD OF THE INVENTION

The present invention relates to treatment and diagnosis of hematopoietic disorders. The invention relates to agents that increase YAP1 levels in cells associated with a hematopoietic disorder and methods for identifying further such agents.

BACKGROUND TO THE INVENTION

Continuous DNA double strand break (DSB) formation, followed by the activation of the DNA damage response (DDR), occurs in both premalignant conditions and established cancers of the epithelial lineage. However, in normal tissues and in precancerous settings, robust senescence and apoptotic responses are mounted, the so-called 'tumorigenesis barrier', that thwarts the progression to malignancy (Halazonetis et al., 2008). During the transition toward cancer, functional inactivation of the tumor suppressor TP53 (p53) suppresses the apoptotic and senescence responses triggered by DSBs and DDR, thereby allowing unfettered tumor cell growth and survival. Hence, in epithelial tumors, p53 loss represents the foremost mechanism by which tumor cells acquire unconstrained genomic instability that allows for the acquisition of additional, favorable mutations and genomic rearrangements, which ultimately promote cancer growth (Halazonetis et al., 2008).

The role of DDR and p53 inactivation is largely unexplored in hematological disorders, albeit evidences of ongoing DNA damage are starting to emerge also in this group of diseases. In a mouse model of acute myeloid leukemia driven by MLL (MLL-AML), activation of the MLL-ENL oncogene induced phosphorylation of histone variant H2A.X ($\gamma$-H2A.X) and activation of the DDR through phosphorylation of ATR and ATM (pATR and pATM) kinases, followed by senescence. Bone marrow biopsies from 3 MLL-rearranged AML patients were positive for pATR, pATM and $\gamma$H2A.X, suggesting that MLL-ENL is associated with a similar response also in humans (Takacova et al., 2012). Variable levels of $\gamma$-H2A.X and pATM have been reported in AML and myelodysplastic syndromes as well (Boehrer et al., 2009). Importantly, the prototype of ongoing DNA damage in a hematological disorders is multiple myeloma (MM), since $\gamma$-H2A.X and pATM have been detected both in the premalignant condition MGUS (Monoclonal Gammopathy of Undetermined Significance), as well as in almost all MM patient cells and cell lines (Walters et al., 2011). However, unlike epithelial cancers, p53 mutations are relatively rare in hematological disorders and appear late during the course of these diseases. In MM for example, p53 mutations and deletions are absent in MGUS, rare in newly diagnosed patients (5-10%), and considered to be a late event in disease progression, being present in 10-20% of patients with relapsed and refractory MM (Xu-Monette et al., 2012). Mutations or loss-of-heterozygosity of ATM and ATR, commonly reported in other cancers as means to overcome DDR-associated apoptosis, are even rarer in MM, and no mutations affecting CHK2 and CHK1 have been identified (Chapman et al., 2011). Therefore, the model proposed for epithelial cancers, whereby p53 mutations allow premalignant cells to overcome senescence and apoptosis despite intense DNA damage to become full-blown tumor cells, might not hold true for hematological disorders.

A pathway downstream of ATM/ATR and alternative to p53 has been described, which is activated after DSB and able to induce apoptosis (Baskaran et al., 1997; Kharbanda et al., 1995; Shafman et al., 1997; Yuan et al., 1996; Yuan et al., 1997). It is centered on the proto-oncoprotein ABL1, commonly translocated in chronic myeloid leukemia (CML) and in acute lymphoblastic leukemia (ALL). Imatinib, a kinase inhibitor that reversibly binds to the ATP kinase pocket of ABL1 and blocks its function, induces apoptosis in the leukemic cells with this translocation and has transformed the treatment and outcome of affected patients since its introduction in the clinic. On the other hand, treatment of cell lines with high-dose DNA damaging agents such as doxorubicin, etoposide and cisplatin results in relocalization of ABL1 from cytoplasm to the nucleus, where it elicits an apoptotic response; therefore, in this context ABL1 acts as a pro-apoptotic gene. Importantly, to date, ABL1 relocalization in the nucleus has been demonstrated only in in vitro settings (tumor cell lines) and has been reported to occur exclusively after drug-induced DNA damage. Therefore, its functional and potential clinical relevance is unknown.

Multiple myeloma is the second most frequent hematological cancer after non-Hodgkin's lymphoma and is characterized by the accumulation of neoplastic plasma cells in the bone marrow. Despite recent advances in therapies and improved patient outcomes, MM remains an incurable cancer with a median survival of 6 years (Palumbo and Anderson, 2011), hence novel therapies are urgently needed.

SUMMARY OF INVENTION

Genomic instability is a hallmark of cancer cells. While epithelial cells inactivate the tumor suppressor p53 to prevent the ensuing apoptosis, in hematological disorders the relevance of ongoing DNA damage and the mechanisms undertaken by hematopoietic cells to survive genomic instability are largely unknown. The inventors identified a p53-independent network in multiple myeloma and other hematopoietic disorders centered on the nuclear relocalization of the pro-apoptotic ABL1 kinase as a result of widespread DNA damage.

It is demonstrated herein that ABL1 is relocalized in the nucleus in MM cells and other hematopoietic disorder cells as a consequence of widespread DNA damage. Nonetheless MM cells are able to survive by genetically inactivating or by exploiting the low expression levels of the Hippo co-transcriptor factor YAP1 levels. The data provided herein shows that increased YAP1 levels in myeloma promote apoptosis by increasing the stability of the tumor suppressor p73 and its downstream targets. Importantly, functional or pharmacological inhibition of STK4, a serine-threonine kinase controlling YAP1 levels, is shown to restore YAP1 levels and induce robust apoptosis, thereby harnessing the ongoing DNA damage present in MM cells as a potential Achilles' heel. Therefore novel therapies targeting STK4 now represent a promising novel therapeutic strategy to improve patient outcome in MM. A synthetic-lethal approach is disclosed whereby myeloma cells with endogenous DNA damage could be selectively targeted.

According to a first aspect of the invention there is provided an agent that increases YAP1 levels for use in the treatment of hematopoietic disorders. Preferably the agent increases YAP1 levels in a hematopoietic cell.

Preferably the hematopoietic disorder has been identified as having reduced YAP1 levels. Preferably the reduced YAP1 levels are in hematopoietic cells associated with the hematopoietic disorder.

Preferably the hematopoietic disorder has also been identified as having nuclear localisation of ABL1. Preferably the nuclear localisation of ABL1 is in hematopoietic cells associated with the hematopoietic disorder.

The term YAP1 level as used herein preferably refers to YAP1 level in hematopoietic cells.

The term "reduced level" or "reduced YAP1 level" as used herein refers to reduced level of YAP1 relative to that of a non-diseased cell, preferably a non-diseased hematopoietic cell, or relative to YAP1 levels of a group of reference patients. The reference patients may be presenting with "high" levels for YAP1, and reduced level is relative to such high levels. The non-diseased cell may be from the same subject to be treated.

The term reduced level preferably requires there to be some YAP1 present. The phrase "hematopoietic disorder has been identified as having reduced YAP1 levels" preferably does not include hematopoietic disorders which have homozygous deletion of YAP1.

The present invention also provides an agent that provides a polynucleotide that encodes YAP1 for use in treatment of hematopoietic disorders. In some embodiments this agent may be used for treating hematopoietic disorders which have homozygous deletion of YAP1.

The level of YAP1 may be controlled at the transcription, translation and post-transcriptional level, for example by non-coding RNAs. The level of YAP1 may also be controlled by processes such as ubiquitylation, sumoylation and acetylation.

In preferred embodiments, the agent is an inactivator of STK4. In this context the inactivator of STK4 prevents STK4 from reducing YAP1 levels. The inactivator of STK4 may have been identified using a screening method of the present invention.

In some embodiments the inactivator prevents or reduces expression of STK4. In some of these embodiments the inactivator is a short hairpin RNA (shRNA), a short interfering RNA (siRNA), or an "miRNA", i.e., small RNAs (20-25 nucleotides in length) that can repress mRNA translation or facilitate mRNA degradation within a cell. Preferably the inactivator is a shRNA. In one embodiment, the agent comprises a shRNA with a sequence of SEQ ID NO: 1, 2, 3 or 4.

In preferred embodiments, the inactivator is an antagonist of STK4. In various embodiments the antagonist prevents or reduces phosphorylation activity of STK4. In one embodiment the antagonist specifically prevents or reduces phosphorylation activity of STK4. In one embodiment the agent is SKI-606 or HKI-272.

In another embodiment the inactivator is located upstream of STK4 in the STK4/YAP1 pathway and the inactivator has an effect on the pathway that causes STK4 to be unable to reduce YAP1 levels.

In another embodiment the inactivator is located downstream of STK4 in the STK4/YAP1 pathway and the inactivator has an effect on the pathway that causes STK4 to be unable to reduce YAP1 levels.

In various embodiments, the agent is comprised within a vector. A vector is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. Examples of vectors used in recombinant DNA techniques include plasmids, chromosomes, artificial chromosomes or viruses.

Examples of viral vectors include lentiviral vectors, retroviral vectors, Murine Leukemia Virus (MLV) vectors, adenovirus vectors, pox viral vectors and vaccinia viral vectors. Examples of retroviral vectors include murine leukemia virus (MLV), human immunodeficiency virus (HIV-1), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al., 1997, "retroviruses", Cold Spring Harbour Laboratory Press Eds: J M Coffin, S M Hughes, H E Varmus pp 758-763.

Preferably, the viral vector is a targeted vector, that is it has a tissue tropism which is altered compared to the native virus, so that the vector is targeted to particular cells.

More preferably, the viral vector preferentially targets a certain hematopoietic cell type or hematopoietic cell types. Preferably the viral vector targets only hematopoietic cells that have a hematopoietic disorder.

In a preferred embodiment the vector is derivable from a lentivirus.

In some embodiments the vector comprises a shRNA which reduces STK4 expression. In some embodiments the shRNA has a sequence of SEQ ID NO: 1, 2, 3 or 4.

In preferred embodiments, the hematopoietic disorder is selected from the group consisting of multiple myeloma, leukaemia or lymphoma. Preferably the hematopoietic disorder is multiple myeloma. In some embodiments the hematopoietic disorder is Waldestrom Macroglobulinemia, ALL or AML.

According to a second aspect of the present invention there is provided use of the agent useful in the invention for the manufacture of a medicament for treating hematopoietic disorders.

According to a third aspect of the present invention there is provided a method of treating a hematopoietic disorder in a subject comprising administering to said subject an effective amount of an agent that increases YAP1 levels, wherein said subject has been identified as having a hematopoietic disorder with reduced YAP1 levels. Preferably the subject has further been identified as having a nuclear localisation of ABL1 in cells associated with the disorder.

This method of treating a hematopoietic disorder may comprise:

A) a method of identifying a hematopoietic disorder with reduced levels of YAP1 in a subject, wherein said method comprises:
  (i) providing a sample from a subject,
  (ii) determining the YAP1 levels in said sample,
  (iii) comparing YAP1 levels in said sample with YAP1 levels in a sample from a healthy subject, a previous sample from said subject, or sample from a reference subject, and
  optionally (iv) identifying whether ABL1 is present in the nucleus of the hematopoietic cells, and B) a method of treating said subject, wherein said treatment comprises administering to said subject an effective amount of an agent that increases YAP1 levels.

In step A (iii), one or more samples may be compared with sample of step (i).

The reference subject may be presenting with "high" levels for YAP1, and reduced level is relative to such high levels. Samples may also be compared with samples from a reference subject presenting with "low" levels for YAP1.

The agent used in the second and third aspects of the invention may be an agent defined by the first aspect of the invention.

Agents useful in the invention may be used together with other types of cancer treatment. For example the agents may be used together with known chemotherapy drugs.

According to a fourth aspect of the present invention there is provided a method of diagnosis or prognosis of a hematopoietic disorder in a subject, wherein said method comprises
(i) providing a sample from said subject,
(ii) determining YAP1 levels in said sample,
(iii) comparing YAP1 levels in said sample with YAP1 levels in a sample from a healthy subject, reference subject or a, previous sample from said subject.

In this method reduced YAP1 levels may be an indicator of disease or poor prognosis.

In step (iii), one or more samples may be compared with sample of step (i).

The reference subject may be presenting with "high" levels for YAP1, and reduced level is relative to such high levels. Samples may also be compared with samples from a reference subject presenting with "low" levels for YAP1, According to a fifth aspect of the present invention there is provided a method for monitoring the progress of hematopoietic disorder in a subject comprising the steps of:
(i) providing a first sample from a subject,
(ii) determining YAP1 levels in said first sample,
(iii) providing a second sample from the subject wherein said second sample is obtained from the subject after said first sample,
(iv) comparing YAP1 levels in the second sample with YAP1 levels in the first sample wherein a decrease in YAP1 levels in the second sample relative to the first sample indicates disease progression.

Comparing the YAP1 levels in the second sample with YAP1 levels in the first sample may be done directly or indirectly. The method may comprise determining YAP1 levels by comparing the YAP1 level in the first and/or second sample with a sample from a healthy subject or a reference subject. Samples from one or more healthy subjects and/or one or more reference subjects may be used. Samples from reference subjects presenting with "high" levels for YAP1 may be used. Samples, may also be compared with samples from a reference subject presenting with "low" levels for YAP1, In one embodiment the method is used to determine progression of multiple myeloma. The progression may be classified in terms of progression from normal plasma cells to Multiple Myeloma (MM). The progression may also be classified in terms of normal plasma cells to Monoclonal Gammopathy of Undetermined Significance (MGUS) and/or MGUS to MM, and/or from MGUS to Smoldering MM, and/or from Smoldering MM to MM.

In one embodiment of this method the second sample is obtained from the subject at least 10, 20, 50, 100, 200 or 300 days after the first sample.

The methods of the present invention comprise the step identifying nuclear localisation of ABL1 in the cells of said sample.

In particularly preferred embodiments of the methods of the present invention, the subject is a human subject.

In some embodiments the methods are for monitoring the progress of a hematopoietic disorder including cancer in response to treatment of hematopoietic disorder including cancer.

In preferred embodiments the methods are for monitoring the progress of a hematopoietic disorder in response to treatment with an agent defined in the first aspect of the present invention.

According to a sixth aspect of the present invention there is provided an antibody directed against YAP1 for use in the treatment or diagnosis of a hematopoietic disorder. The YAP1 antibody may be used together with one or more other antibodies. Preferably the YAP1 antibody is used together with an ABL1 antibody. In one embodiment the diagnostic test is performed in vitro. Preferably the diagnostic test is performed in a sample from a subject.

The present invention also provides YAP1 PCR primers for use in a diagnostic test for hematopoietic disorders.

The present invention also provides YAP1 in situ hybridisation probes for use in a diagnostic test for a hematopoietic disorder.

The present invention provides screening methods for identifying an agent capable of inducing apoptosis in hematopoietic cells associated with a hematopoietic disorder and for identifying an STK4 inactivator. The agent may be a naturally occurring macromolecule or a synthetic one such as a drug.

According to a seventh aspect of the present invention there is provided a method for identifying an agent capable of inducing apoptosis in cells associated with a hematopoietic disorder, said method comprising:
(i) providing a first sample comprising a cell, group of cells, animal model or human; (ii) administering said agent to said first sample;
(iii) determining YAP1 levels in said first sample;
(iv) providing a second sample comprising a cell, group of cells, animal model or human wherein said agent is not administered to said second sample; and
(v) comparing YAP1 levels in the first sample with YAP1 levels in the second sample, wherein an increase in YAP1 levels in the first sample relative to the second sample indicates ability of said agent to induce apoptosis in hematopoietic cells.

According to another aspect of the present invention there is provided a method for identifying an agent capable of inducing apoptosis in hematopoietic cells associated with a hematopoietic disorder, said method comprising:
(i) providing a sample comprising a cell, group of cells, animal model or human;
(ii) contacting said sample with an agent; and
(iii) determining the YAP1 levels in said sample prior to and after contact with said agent;
(iv) wherein an increase in YAP1 levels after contact with said agent indicates ability of said agent to induce apoptosis in hematopoietic cells associated with a hematopoietic disorder.

Preferably the agent identified by the above methods of the present invention is an inactivator of STK4.

The present invention provides a method for identifying an agent capable of inducing apoptosis in cells associated with a hematopoietic disorder comprising the step of identifying an agent that inactivates STK4.

A further screening method is also provided by the present invention. This method is a method for identifying an agent capable of inducing apoptosis in cells associated with a hematopoietic disorder wherein said agent is an STK4 inactivator, said method comprising:

(i) identifying an agent that is an STK4 inactivator,
(ii) providing a first sample comprising a cell, group of cells, animal model or human;
(iii) administering said agent that is an STK4 inactivator to said first sample;
(iv) determining YAP1 levels in said first sample;
(v) providing a second sample comprising a cell, group of cells, animal model or human wherein said agent is not administered to said second sample; and
(vi) comparing YAP1 levels in the first sample with the level of the YAP1 in the second sample, wherein an increase in YAP1 levels in the first sample relative to the second sample indicates ability of said agent to induce apoptosis in cells associated with a hematopoietic disorder.

In preferred embodiments of the screening methods of the present invention the samples comprise haematopoietic cells or cells of cell lines that are derived from haematopoietic cells. Preferably these cells have been identified as having ABL1 present in their nucleus.

In some embodiments of the screening methods of the present invention the group of cells is a cell culture.

In some embodiments of methods of the present invention YAP1 levels are determined by quantitative PCR, an immuno-assay or flow cytometry.

The present invention also provides kits comprising YAP1 PCR primers or YAP1 antibodies for use in testing for YAP1 levels in diagnostic methods of the present invention. These kits may also comprise ABL1 antibodies.

According to the present invention the hematopoietic disorder may be for example selected from the group consisting of multiple myeloma, leukaemia or lymphoma. Preferably the hematopoietic disorder is multiple myeloma. In some embodiments the hematopoietic cancer is Waldestrom Macroglobulinemia, ALL or AML.

In another aspect of the present invention there is provided an antibody, method or agent for use substantially as described herein.

Further preferred features and embodiments of the present invention will now be described by way of non-limiting example and with reference to the accompanying drawings in which:

DESCRIPTION OF THE DRAWINGS

FIG. 1A—Left panel: γ-H2A.X staining of MM cell lines. Upper right panel: Quantitative evaluation of γ-H2A.X foci number. Mean values±SD derived from triplicate experiments are shown. Lower right panel: Western blot analysis of γ-H2A.X in MM cell lines. Peripheral Blood Mononuclear Cells (PBMCs) and HeLa cells treated with 1 µM doxorubicin for m24 hours represent the negative and positive controls, respectively. GAPDH as loading control.

FIG. 1B—Western blot analysis and immunofluorescence staining of γ-H2A.X in PBMCs and two MM patients.

FIG. 1C—Western blot analysis of pATM (Ser1981), pCHK2 (Thr68), pATR (Ser428), and pCHK1 (Ser296) and their corresponding unmodified forms in MM cell lines and patient samples.

FIG. 1D—Left panel: Annexin V-FITC/PI staining and western blot analysis of cleaved caspase 3/Cleaved PARP in MM.1S and H929 MM cell lines and in two patients. Right panel: Immunofluorescence staining for γ-H2A.X-Texas Red, cleaved caspase 3-Alexa 488, and DAPI in MM.1S cells and MM patient cells. As positive control, cell lines and patient cells were treated with 5 nM Bortezomib (BTZ) for 48 h.

FIG. 2A—Subcellular fractionation of TP53-WT and TP53-mutant MM cell lines. Equivalent cell lysates from cytoplasmic (C) and nuclear (N) fractions were analyzed by Western blot for ABL1 expression. α-tubulin and Histone H3 were used as loading controls for C and N fractions, respectively.

FIG. 2B—Immuno-histochemical ABL1 staining on two representative patient samples. Left panel, patient 3, 400×. Middle panel, patient 4, 400×. Right panel, patient 4, 1000× magnification.

FIG. 2C—MM cell lines were treated with DMSO or 2-10 µM ATM kinase inhibitor Ku55933 for 1-2 hours in MM.1S and for 2 hours in UTMC-2, JJN-3 and KMS-20 cells. Lysates were blotted for ABL1, α-tubulin (C loading control), and p84 (N loading control).

FIG. 2D—MM cell lines were treated with DMSO or 10 µM SAPK/JNK1 inhibitor SP600125 for 2 hours. Lysates were blotted as in (A).

FIG. 3A—Immunofluorescence staining for γ-H2A.X and Western blot analysis for γ-H2A.X, p-ATM (Ser1981) and p-SAPK/JNK (Thr183/Tyr185) on total lysates, as well as ABL1, Histone H3, α-tubulin in U266 cells, before and after Doxorubicin (DOXO; 40 nM) treatment.

FIG. 3B—Annexin V-FITC/PI staining (upper panel) and MTT absorbance assay (lower panel) in U266 cells at 48 h (DOXO, 40 nM; imatinib, 10 µM). Data are mean values±SD of triplicates.

FIG. 3C—Western blot for ABL1, Histone H3, α-tubulin in MM.1S and UTMC-2 cells, before and after Doxorubicin (DOXO; 40 nM) treatment. Annexin V-FITC/PI staining and MTT absorbance assay in MM.1 S and UTMC-2 cells at 48 h as in (B)

FIG. 4A—YAP1 mRNA expression in solid tumors and hematological cancers (Oncomine at www.oncomine.org; Wooster Cell Line dataset).

FIG. 4B—Gene dosage comparison across cell lines and tumors demonstrating homozygous deletions at the YAP1 locus. Number 1 corresponds to data derived from (Keats et al., 2007), 2 from (Carrasco et al., 2006), and 3 from (Walker et al., 2010).

FIG. 4C—Survival curve relative to YAP1 expression in MM patients, obtained from www.canevolve.org and based on GSE2658.

FIG. 4D—Expression data comparing plasma cells from healthy individuals, MGUS, MM, and cell lines (CL), combining data from GSE5900, GSE2658 and from the MMRC collection (http://www.broadinstitute.org/mmgp), probe set 224895_at. Statistical comparisons between each patient subgroup and cell lines are not shown.

FIG. 4E—YAP1 gene, expression and protein levels in various MM cell lines and patient MM cells. Top panel: Non-quantitative PCR on genomic DNA from YAP1-deleted MM cell lines KMS-18 and KMS-20 and additional cell lines. Middle panel: mRNA levels measured by qPCR analysis and calculated as fold changes on a panel of MM cell lines. Bottom panel: Western blot analysis of YAP1 in MM cell lines and patient MM samples. As positive control, lysates from 293T cells transfected with YAP1-EGFP vector were used (band at 98 kD).

FIG. 5B—YAP1 silencing in UTMC-2 MM cell line using a lentiviral delivery system. Left panel: qPCR and western blot analysis as in (A) in cells transfected with a control vector (pLKO.1-scrambled) or shRNA#1/shRNA#3 after antibiotic selection. Middle panel: as in (A). Right panel: Apoptosis is measured with Annexin V-FITC/PI staining. The percentage of dead cells is the sum of Annexin V+PI+, Annexin V+, PI− and Annexin V−, PI+ cells.

FIG. 5C—YAP1 re-expression in UTMC-2 MM cell line transfected as in (A). YAP1 levels were evaluated at 72 hours as in (A). The two bands present in the western blot correspond to basally expressed, wild type YAP1 (64 kD) and to YAP1-EGFP (98 kD). Right panel: cell growth and apoptosis are measured.

FIG. 5D—Growth inhibition was evaluated by MTT absorbance assay in UTMC2 and in KMS-20 cells respectively, after treatment with 40 nM Doxorubicin (DOXO) for 48 hours.

FIG. 5E—YAP1 re-expression in MM.1S MM cell line transfected as in (A). YAP1 levels were evaluated at 72 hours as in (A). Cell viability is measured by MTT absorbance assay, and cellular growth by cell counting with trypan blue exclusion, as in (A). PI staining was performed as in (A).

FIG. 5F—YAP1 re-expression in combination with imatinib treatment. KMS-20 transfected cells with pLENTI4-YAP1-EGFP versus control (pLENTI4-LACZ) were incubated with 10 μM imatinib from day 0 of transfection. Cellular counting was performed in triplicate for each condition, with trypan blue exclusion. Right panel: Apoptosis by Annexin V-PE/7AAD, gating on GFP-positive cells. The percentage of viable cells (Annexin V-PE-/7AAD-cells) is shown at 48 hours.

FIG. 6A—Western blot analysis of YAP1, p73, and p73-target gene protein levels in MM.1S and U266 non-treated cells or after incubation with 40 nM doxorubicin (DOXO) alone or with 10 μM imatinib.

FIG. 6B—Left panel: Western blot analysis for p73, p73-target genes (BAX, PUMA, p21), and NOXA in KMS-20 pLENTI4-YAP1-EGFP and LACZ transfected cells. Right panel: P73 mRNA levels (Delta delta Ct method) are shown in both KMS-20 YAP1-EGFP versus KMS-20 LACZ-transfected cells, and UTMC-2 YAP1-silenced cells versus UTMC-2 scrambled infected cells.

FIG. 7B—Cells treated with 10 μM of SKI-606 and HKI-272 for 24-72 hours. Left panel, total lysates obtained at 24 hours. Middle panel, Annexin V-FITC/PI staining Right panel, MTT absorbance assay. Mean values±SD of triplicates of two experiments are shown.

FIG. 7C—MTT assay of quadruplicate cultures, expressed as a percentage of untreated control. Data represent mean±SD.

FIG. 7D—MM.1S cells cultured for 24 hours with DMSO, 10 μM SKI-606, and 10 μM HKI-272, with or without 20-40 nM DOXO.

FIG. 7E—Model for the ABL1/YAP1/p73 axis in MM and the effect of STK4 inhibition on YAP1 levels.

FIGS. 8A-8D show representative YAP1 nucleotide and amino sequences

FIG. 8A—Representative mRNA nucleotide sequence (SEQ ID NO: 29) coding YAP1 polypeptide. This sequence is also shown in GenBank Accession number: NM_001130145.

FIG. 8B—Representative amino acid sequence (SEQ ID NO: 30) of YAP1 polypeptide. This sequence is also shown in GenBank Accession number: NP_001123617.1.

FIG. 8C—Representative mRNA nucleotide sequence (SEQ ID NO: 31) encoding YAP1-isoform2 (YAP2): polypeptide. This sequence is also shown in GenBank Accession number: NM_006106.4.

FIG. 8D—Representative amino acid sequence (SEQ ID NO: 32) of YAP1-isoform2 (YAP2): This sequence is also shown in GenBank Accession number: NP_006097.2.

FIG. 9A—Representative mRNA nucleotide sequence (SEQ ID NO: 33) encoding STK4 polypeptide. This sequence is also shown in GenBank Accession number: NM_006282.2

FIG. 9B—Representative amino acid sequence (SEQ ID NO: 34) of STK4 polypeptide. This sequence is also shown in GenBank Accession number: NP_006273.1.

FIG. 9C—Representative mRNA nucleotide sequence (SEQ ID NO: 35) encoding STK3 (a homologue of STK4) polypeptide. This sequence is also shown in GenBank Accession number: NM_006281.3

FIG. 9D—Representative amino acid sequence (SEQ ID NO: 36) of STK3 (a homologue of STK4) polypeptide. This sequence is also shown in GenBank Accession number: STK3: NP_006272.2

FIGS. 10A-10B show representative ABL1 nucleotide and amino sequences

FIG. 10A—Representative mRNA nucleotide sequence (SEQ ID NO: 37) encoding ABL1 polypeptide. This sequence is also shown in GenBank Accession number: NM_005157.41

FIG. 10B—Representative amino acid sequence of ABL1 polypeptide. This sequence is also shown in GenBank Accession number: NP_005148.2.

SUPPLEMENTAL FIGURES 1E-1F.

Figure 1A:
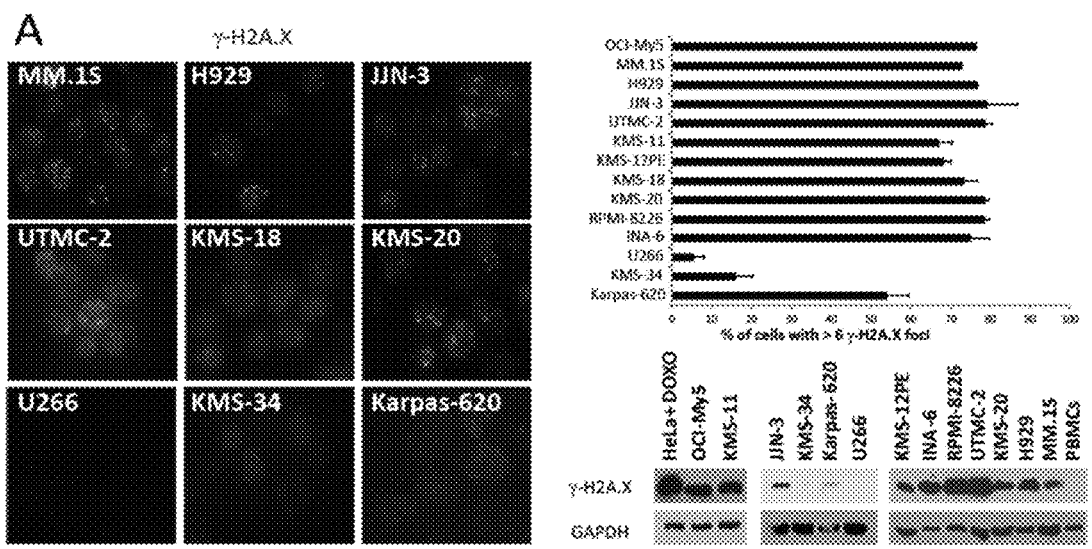
FIGS. 1A-E. Despite active DNA damage, MM cells do not demonstrate ongoing apoptosis.
Figure 1B:
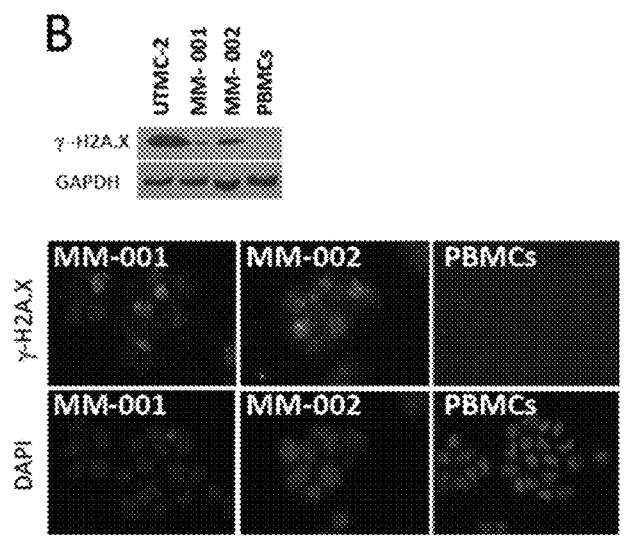
Figure 1E:
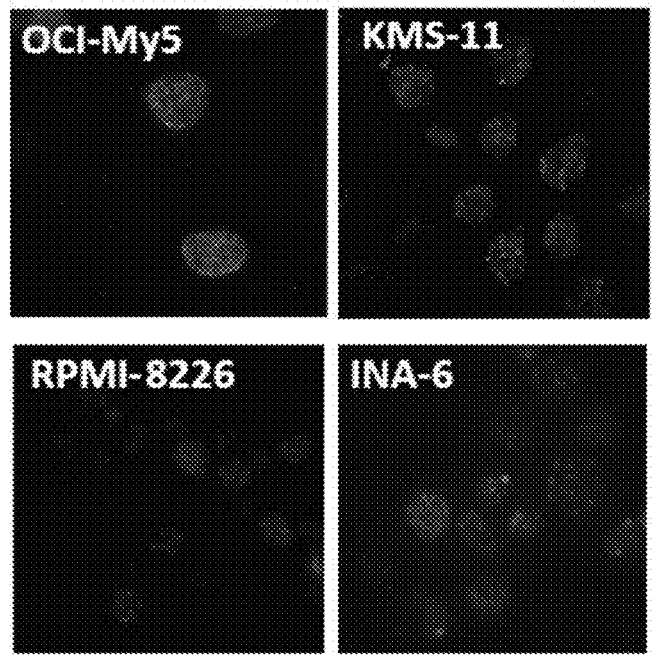

FIG. 1E—γ-H2A.X and nuclear content (DAPI) immunofluorescence staining on other MM cell lines.

Figure 1F:
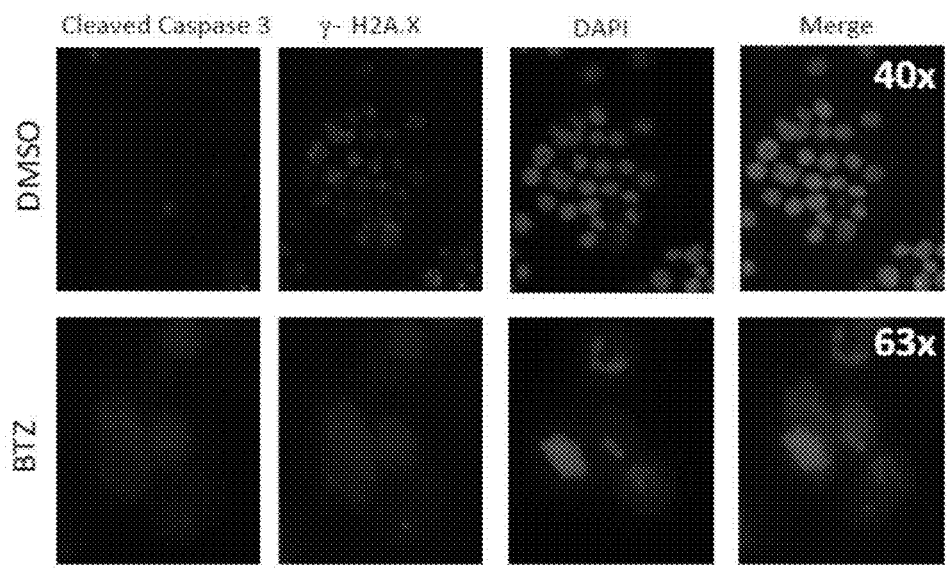

FIG. 1F—Immunofluorescence staining of γ-H2A.X-Texas Red, cleaved caspase 3-Alexa 488, and nuclear content (DAPI) in H929 MM cells treated with 5 nM bortezomib (BTZ) for 48 hours.

SUPPLEMENTAL FIGURES 2E-2J.

Figure 2A:
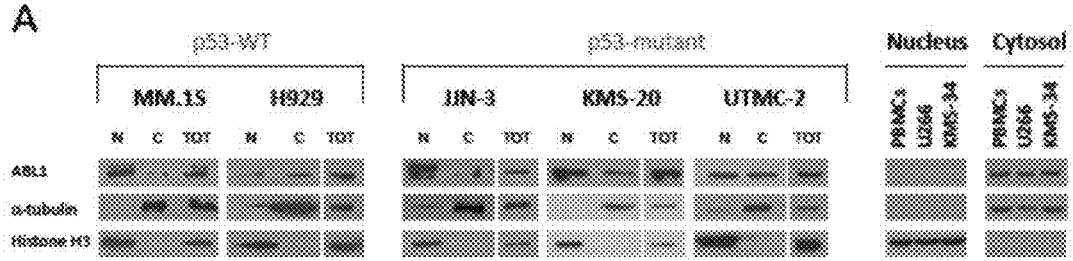
FIGS. 2A-D. ABL1 localization in the nucleus of MM cells is reversed by ATM or SAPK/JNK-signaling inhibition.
Figure 2B:
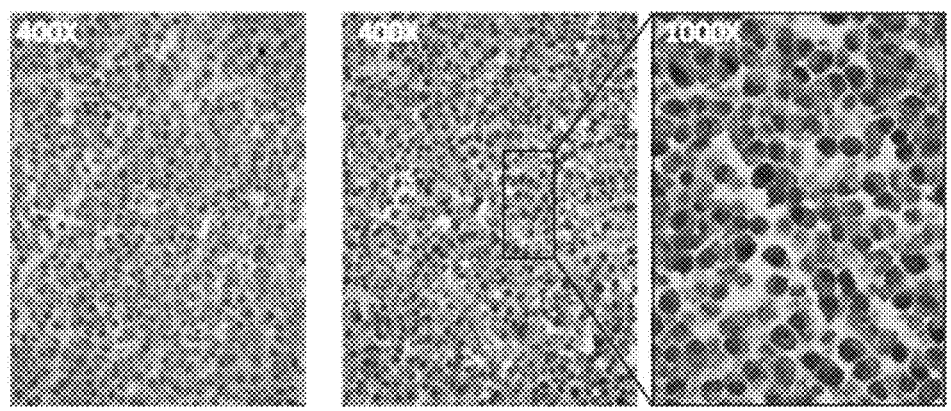
Figure 2C:
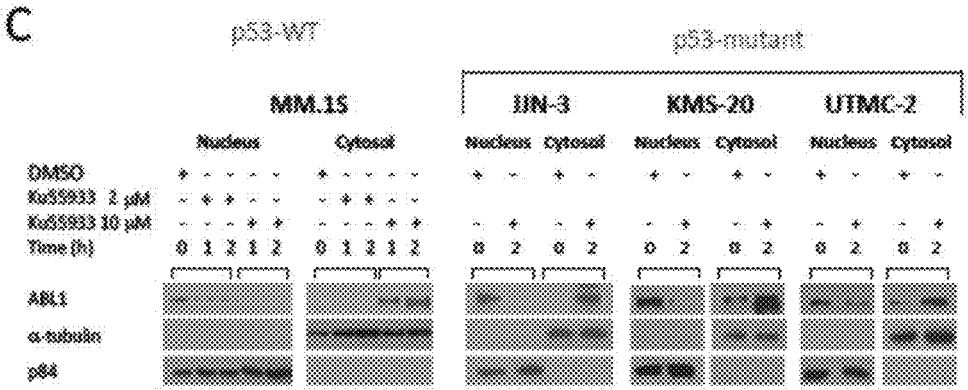
Figure 2D:
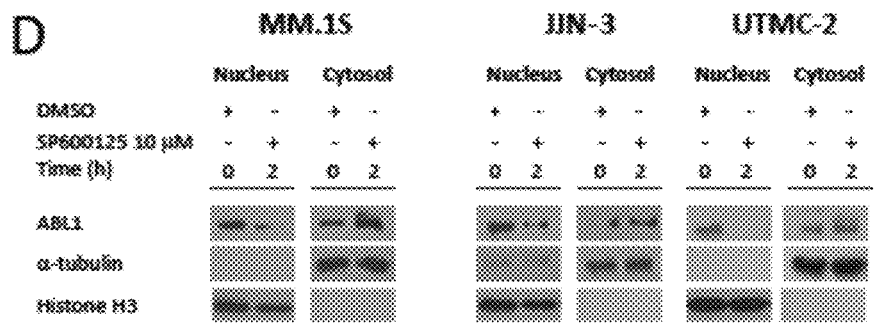
Figure 2E:
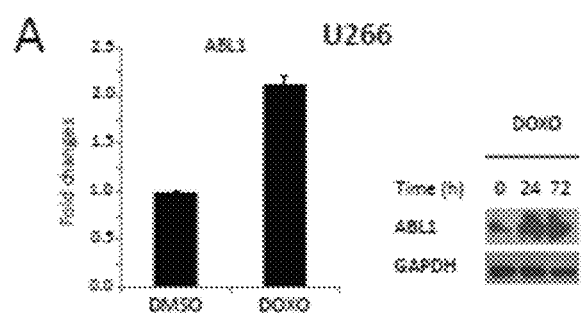

FIG. 2E—ABL1 mRNA and protein levels in untreated-U266 and after incubation with 40 nM Doxorubicin (DOXO) for 24-72 hours. mRNA modifications are shown as fold changes, calculated using delta delta Ct method.

Figure 2F:
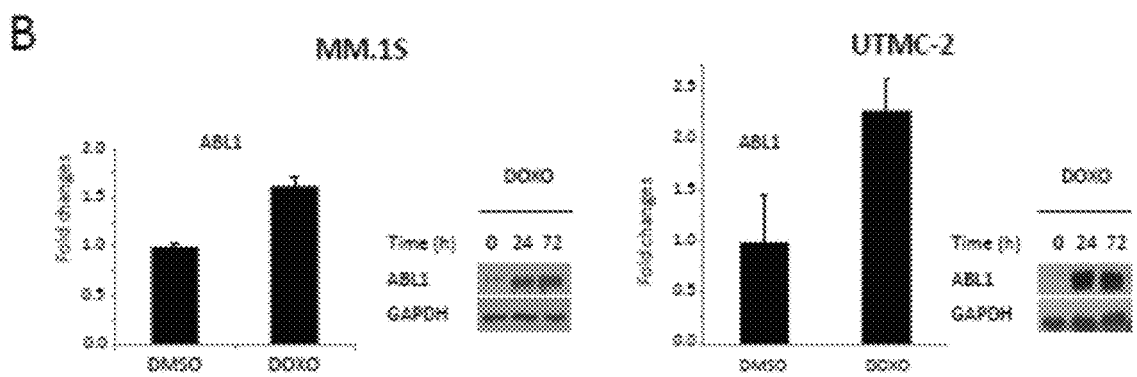

FIG. 2F—ABL1 mRNA and protein levels in untreated-MM.1S and untreated-UTMC-2 and after incubation with 40 nM DOXO for 24-72 hours. mRNA modifications are calculated as in (E).

Figures 2G, 2H:
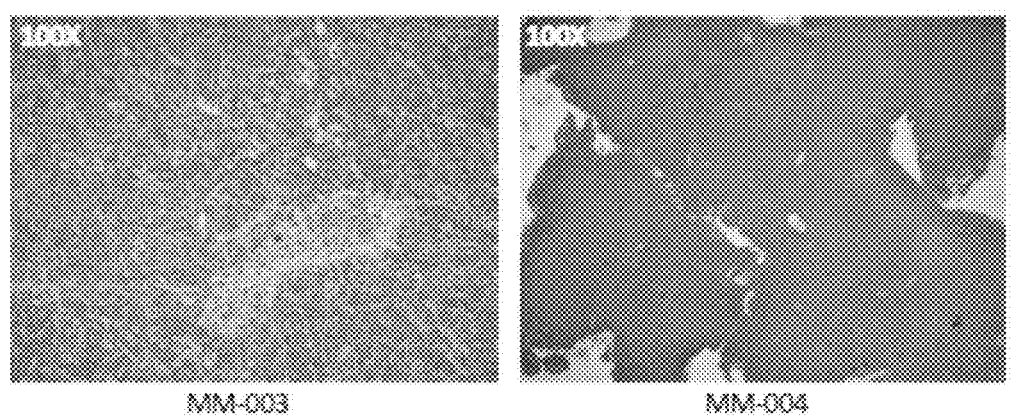

FIG. 2G—Immuno-histochemical ABL1 staining in patient samples. Left panel, patient 3, 100×. Right panel, patient 4, 100× magnification.

FIG. 2H—H929 MM cell line was treated with DMSO or 10 μM ATM kinase inhibitor Ku55933 for 6-24 hours. Cellular fractionation was performed, and cell lysates were blotted with ABL1, α-tubulin, and p84 (as loading control) and phospho-CHK2 (Thr68) (as control of Ku55933 activity).

Figure 2I:
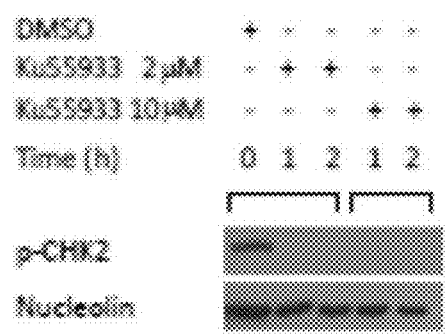

FIG. 2I—Western blot for phospho-CHK2 (Thr68) in MM.1S cells treated with DMSO or 2-10 μM Ku55933 for 1 or 2 hours.

Figure 2J:
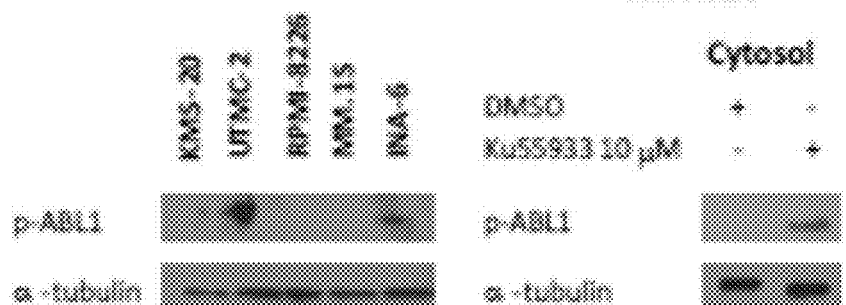

FIG. 2J—Western blot analysis for phospho-ABL1 (Thr735) at basal conditions in total lysates or after incubation with 10 μM Ku55933 for 2 hours in MM.1S cytosolic fraction.

SUPPLEMENTAL FIGURES 3D-3F.

Figure 3A:
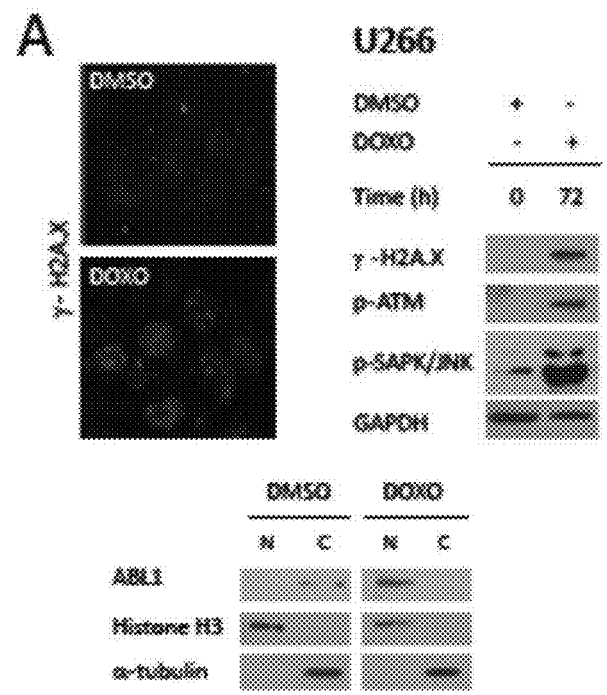
FIGS. 3A-3C. ABL1 mediates doxorubicin-induced apoptosis.
Figure 3B:
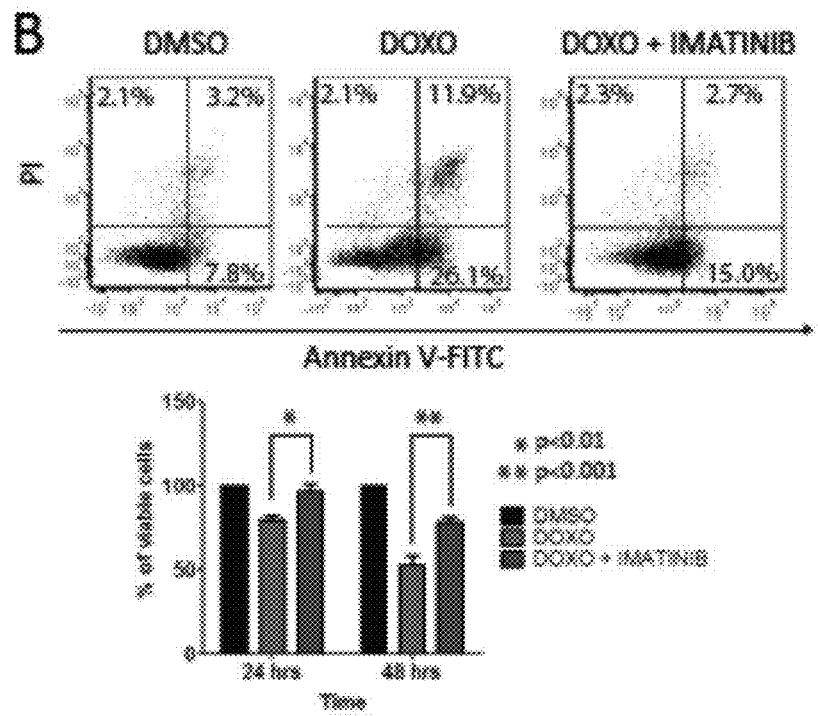
Figure 3C:
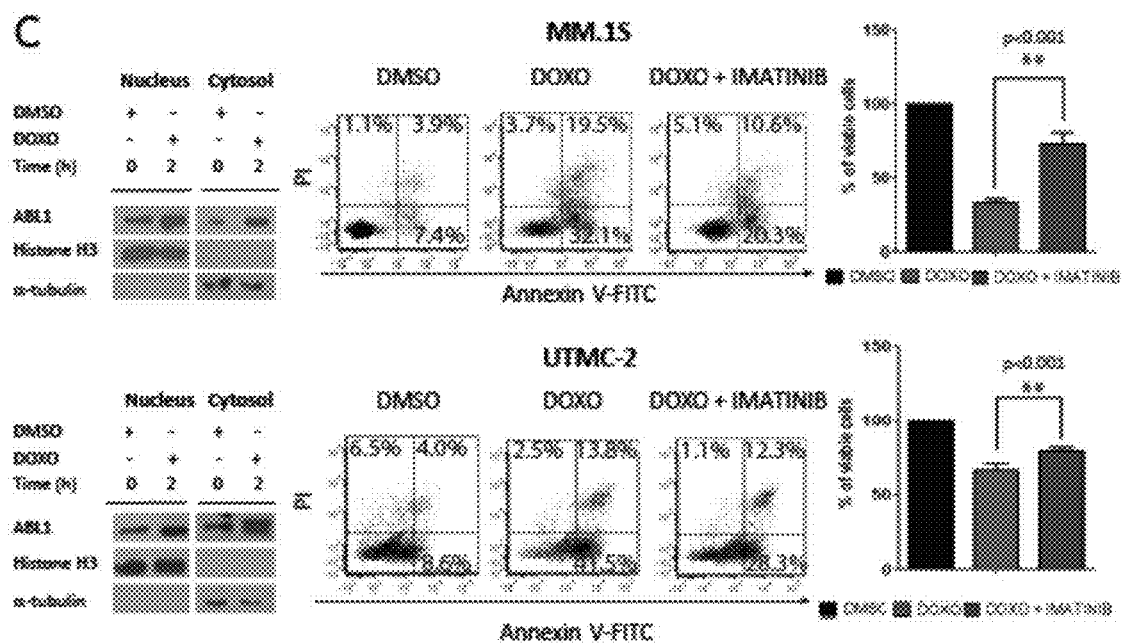
Figure 3D:
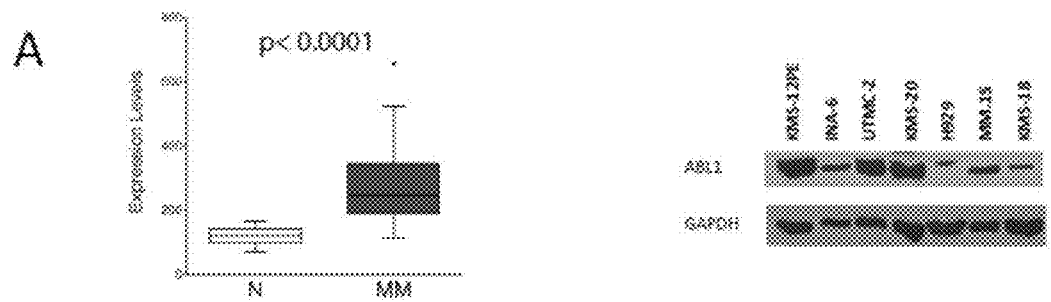

FIG. 3D—ABL1 expression in MM. Left panel: ABL1 mRNA levels in normal plasma cells versus MM patient samples. ABL1 Affymetrix probe: 202123_s_at, data set GSE4452. Right panel: ABL1 protein expression in MM cell lines.

Figure 3E:
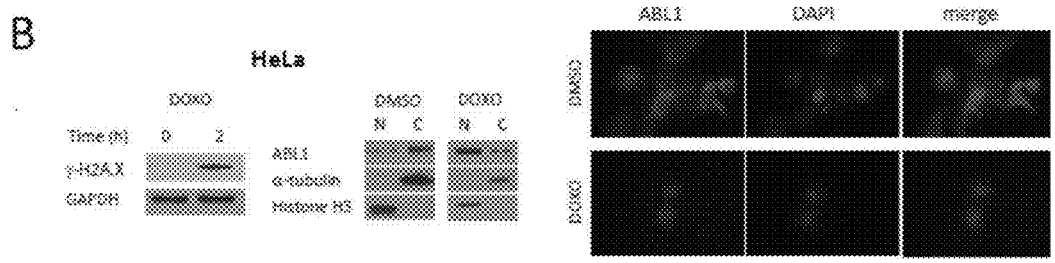

FIG. 3E—ABL1 cellular localization in HeLa cell line. HeLa were incubated for 2 hours with DMSO or 1 μM doxorubicin (DOXO). Left panel: Western blot with total lysates for γ-H2.AX and with nuclear (N) and cytosolic (C) fractions for ABL1, α-tubulin, and histone H3 are shown. Right panel: Immunofluorescence for ABL1 and nuclear content (DAPI) after two-hour incubation with DMSO or 1 μM DOXO.

Figure 3F:
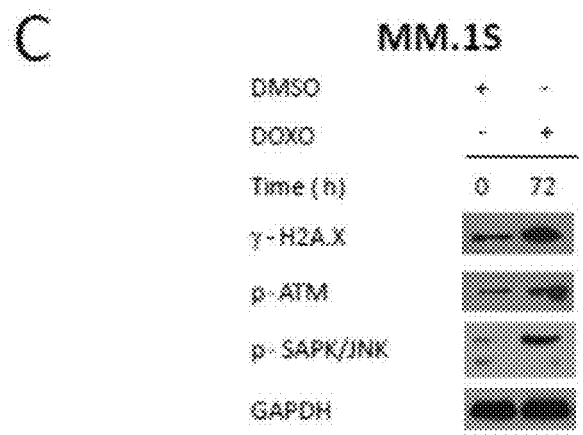

FIG. 3F—Western blot analysis of γ-H2A.X, p-ATM (Ser1981), and p-SAPK/JNK (Thr183/Tyr185) in MM.1S untreated cells and after incubation with 40 nM DOXO for 72 hours.

SUPPLEMENTAL FIGURES 4F-4H.

Figure 4A:
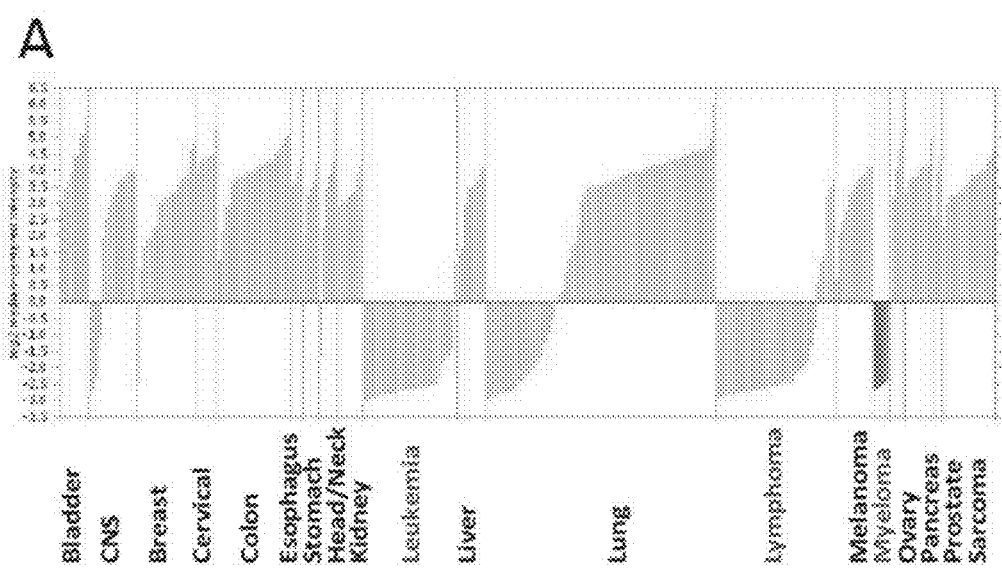
FIGS. 4A-4E. YAP1 Deletions and Expression in MM Cell Lines and Patient Samples.
Figure 4B:
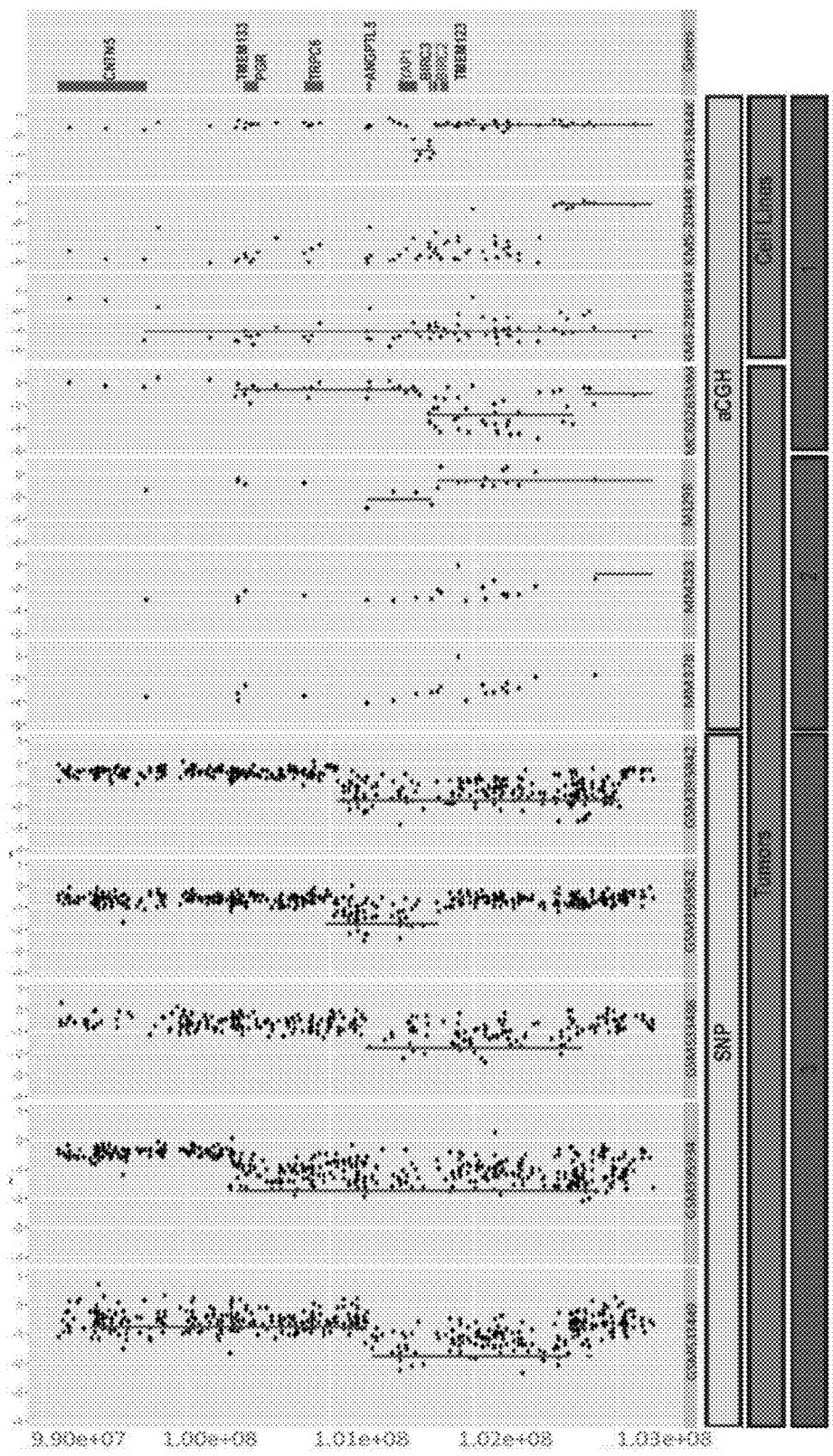
Figure 4C:
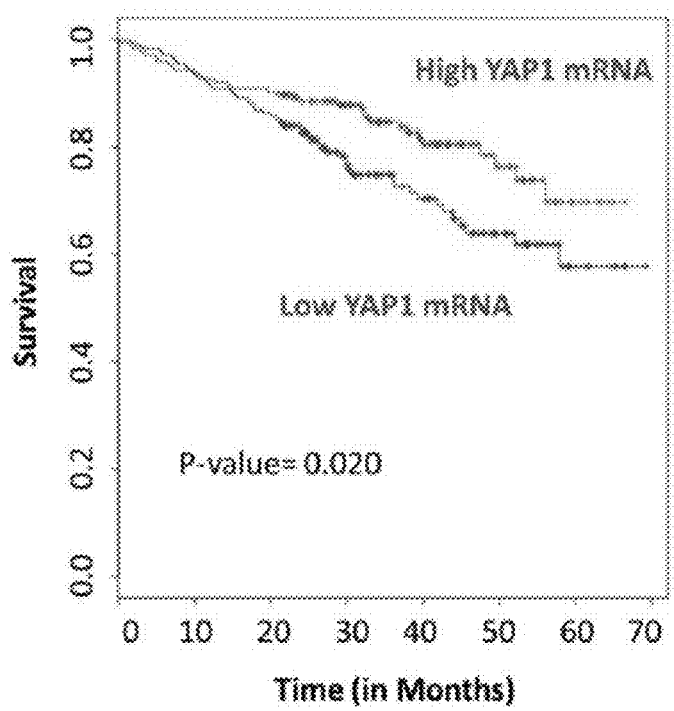
Figure 4D:
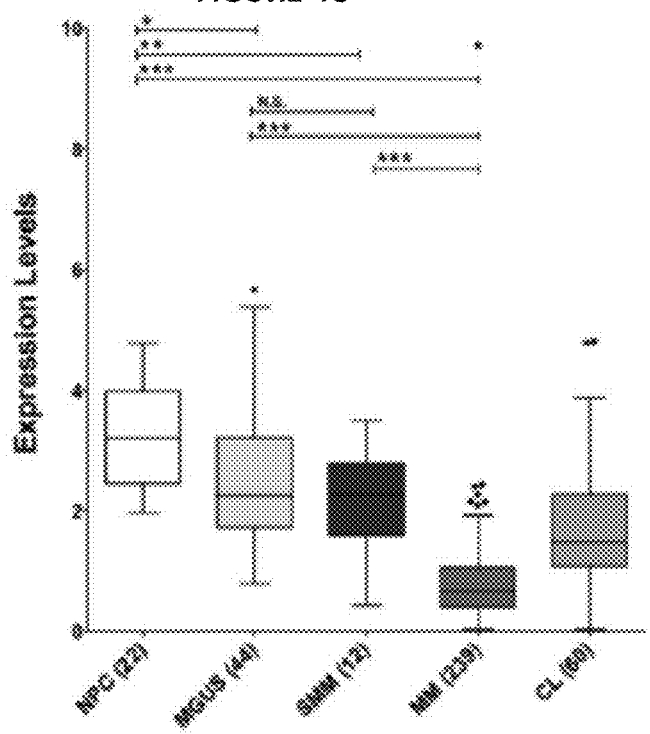
Figure 4E:
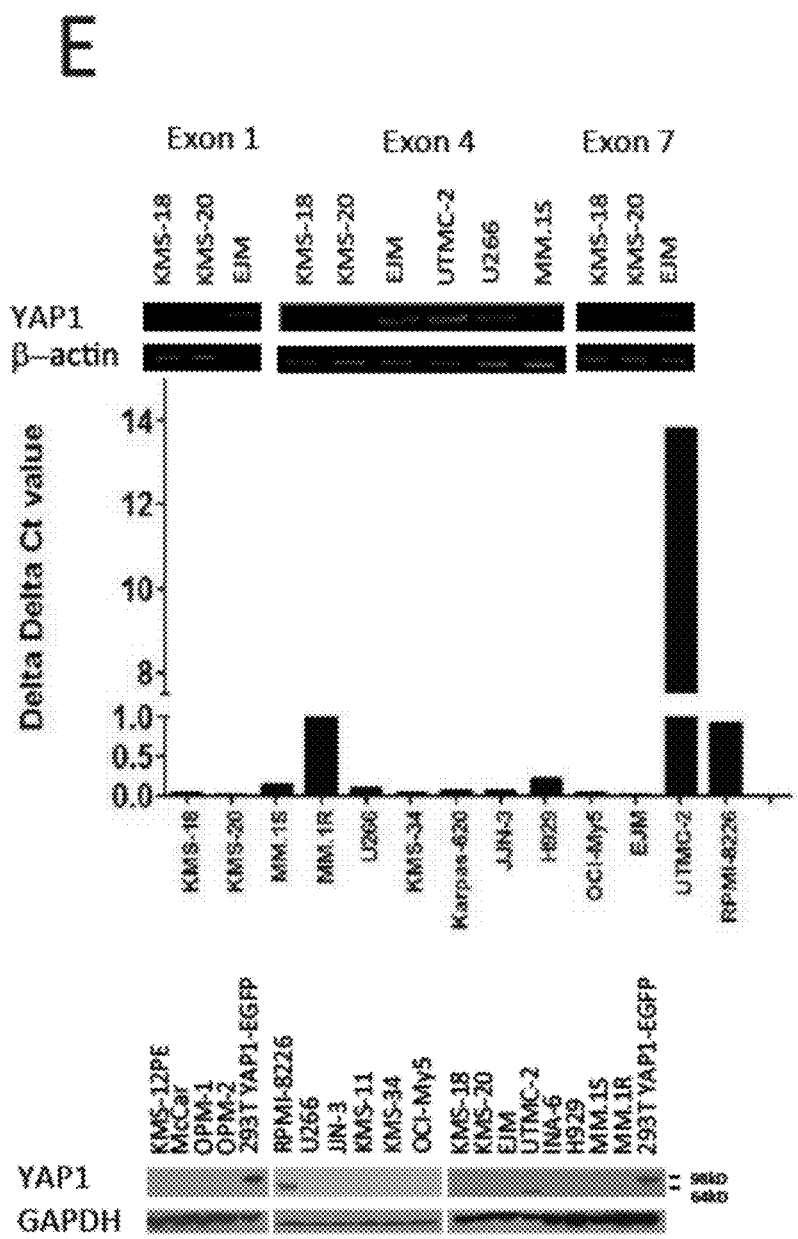
Figure 4F:
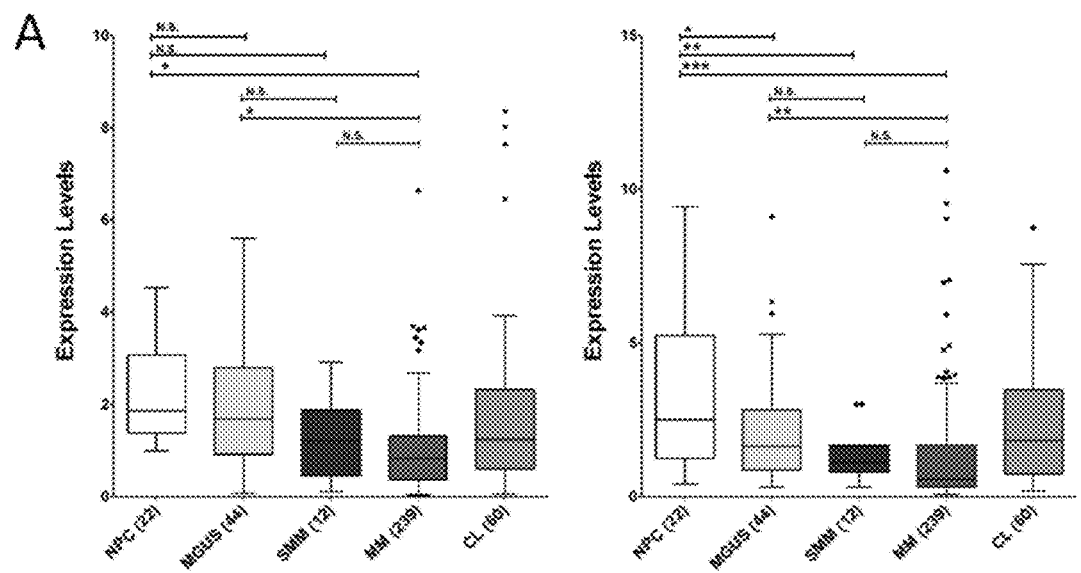

FIG. 4F—YAP1 expression in the same dataset as in FIG. 4. On the left panel, probe set 228494_at, on the right panel 213342_at. GSE2658 (559 newly diagnosed MM tumors) and GSE5900 (22 NPC, 44 MGUS, 12 SMM) provide U133_Plus_2 data normalized with MAS software, version 5.01 (Affymetrix, Santa Clara, Calif.). The data was log transformed, normalized to the 75th percentile, and normalized to the median of specific probe sets using GeneSpring0.

Figure 4G:
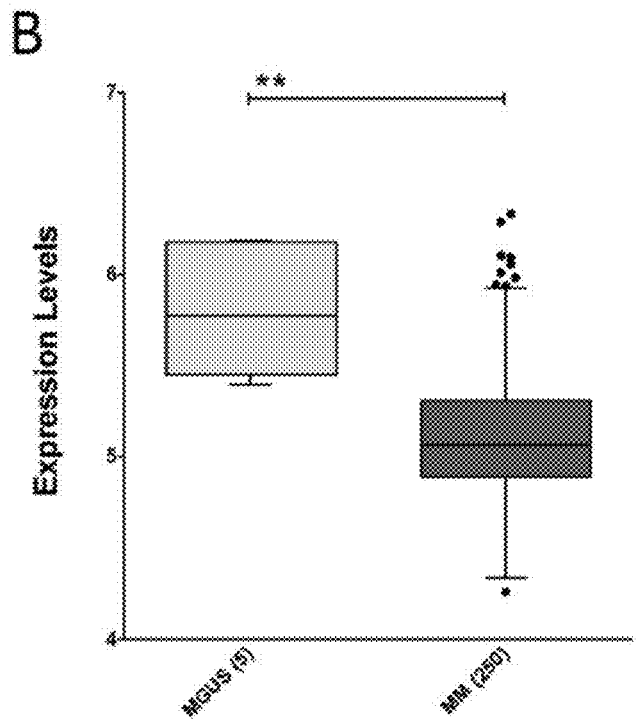
Figure 4H:
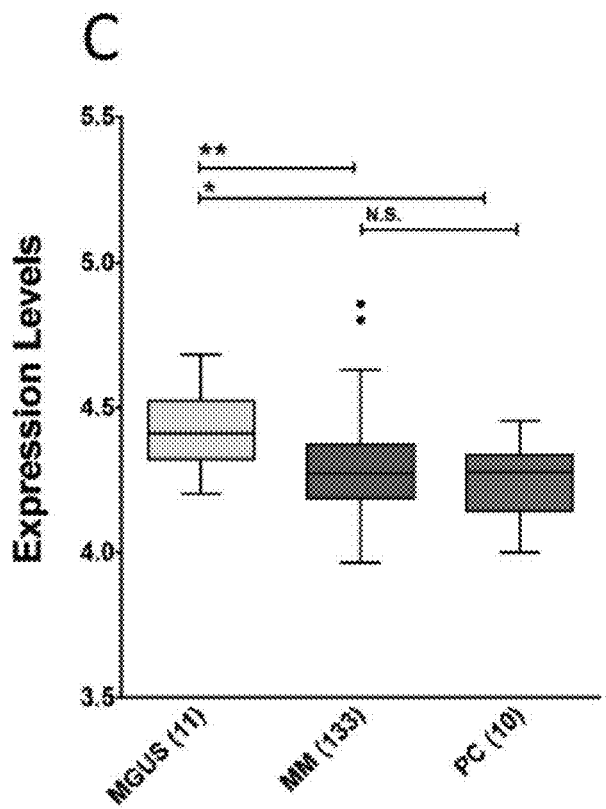

FIG. 4G—YAP1 expression in MGUS and MM patients obtained from E-MTAB-372, probe set 224895_at FIG. 4H—YAP1 expression in MGUS, MM and Plasma Cell Leukemia (PCL) patients obtained from the GSE13591 dataset.

SUPPLEMENTAL FIGURES 5H-5K.

Figure 5A:
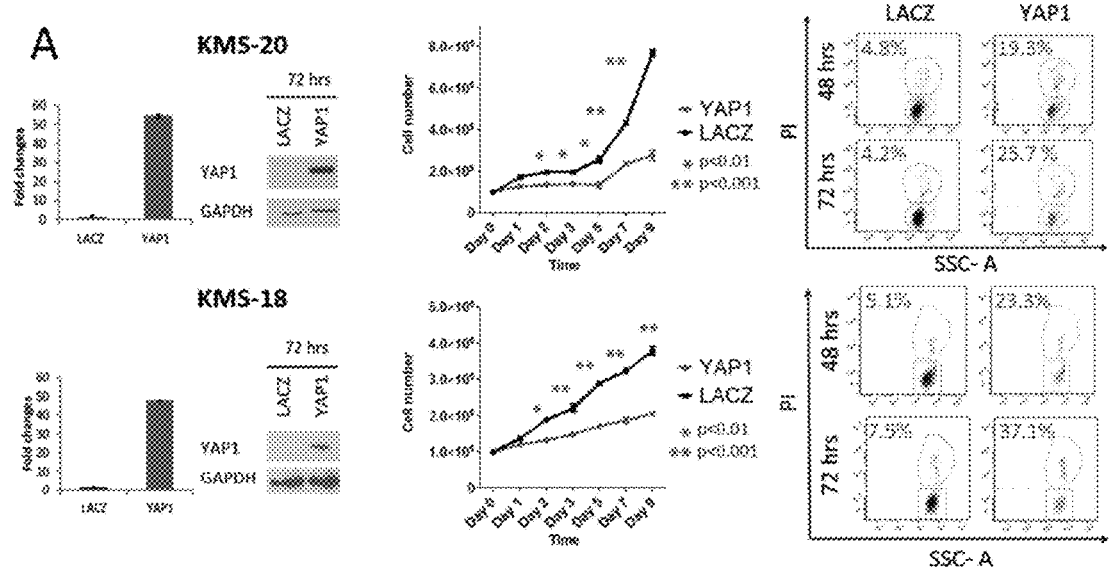
FIGS. 5A-5F. YAP1 re-expression leads to ABL1-dependent reduced proliferation and cell death FIG. 5A—YAP1 re-expression in KMS-20 (upper) and KMS-18 (lower) MM cells using AMAXA electroporation. Left panel: qPCR (Delta delta Ct) and western blot analysis at 72 hours. Middle panel: cell growth evaluated with cell counting with trypan blue exclusion. Mean values±SD of triplicate of two experiments are shown. Right panel: PI staining was used to detect dead cells after gating on GFP-positive cells.
Figure 5B:
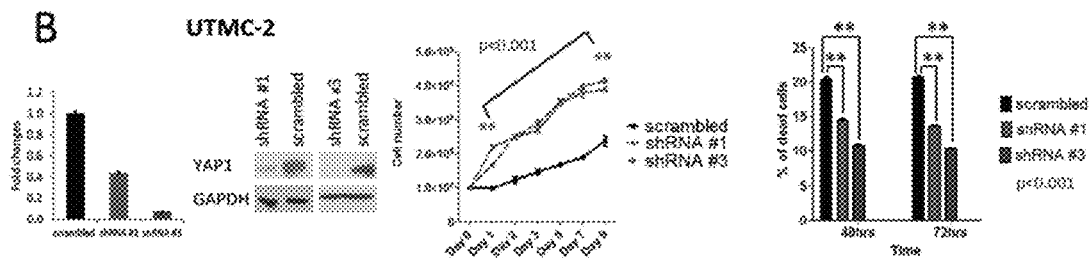
Figure 5C:
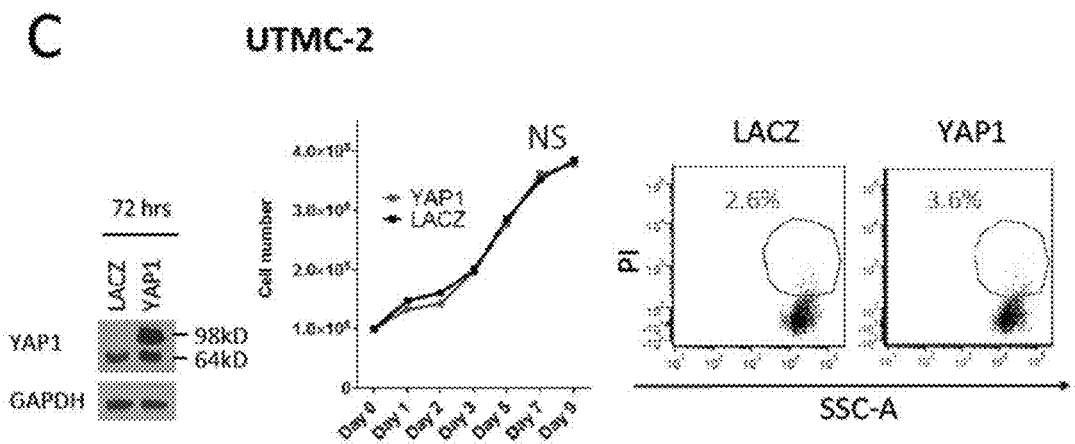
Figure 5D:
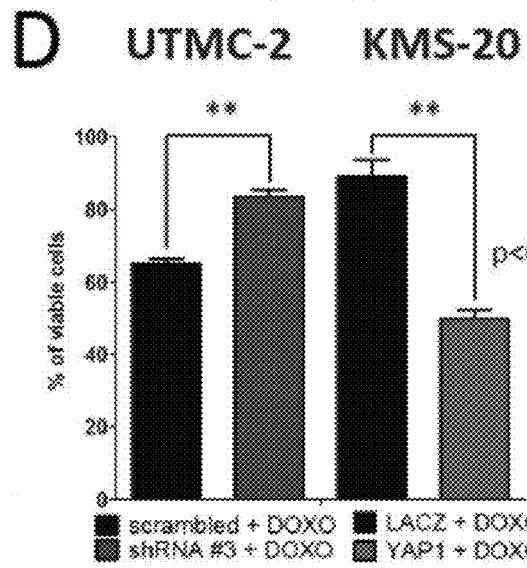
Figure 5E:
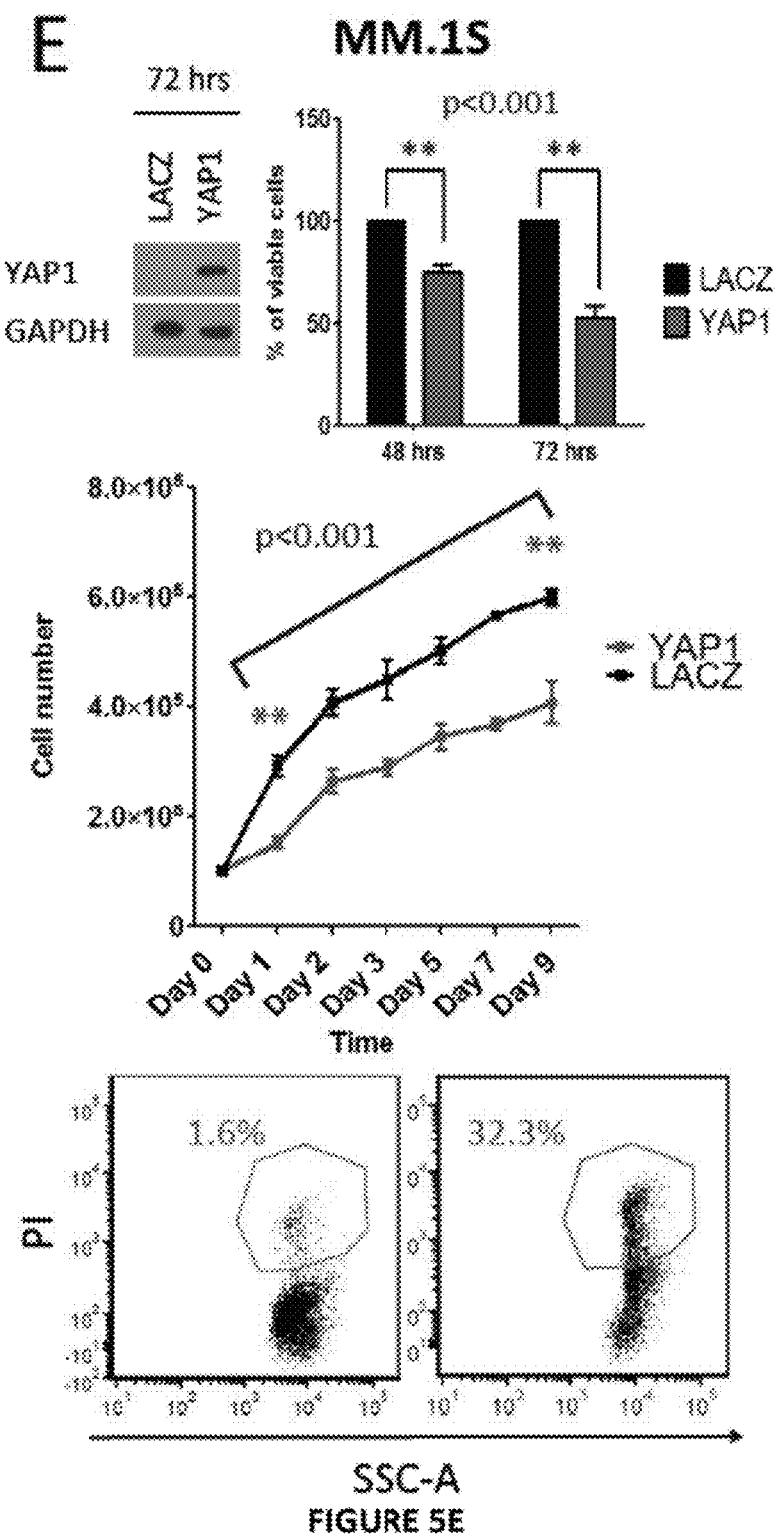
Figure 5F:
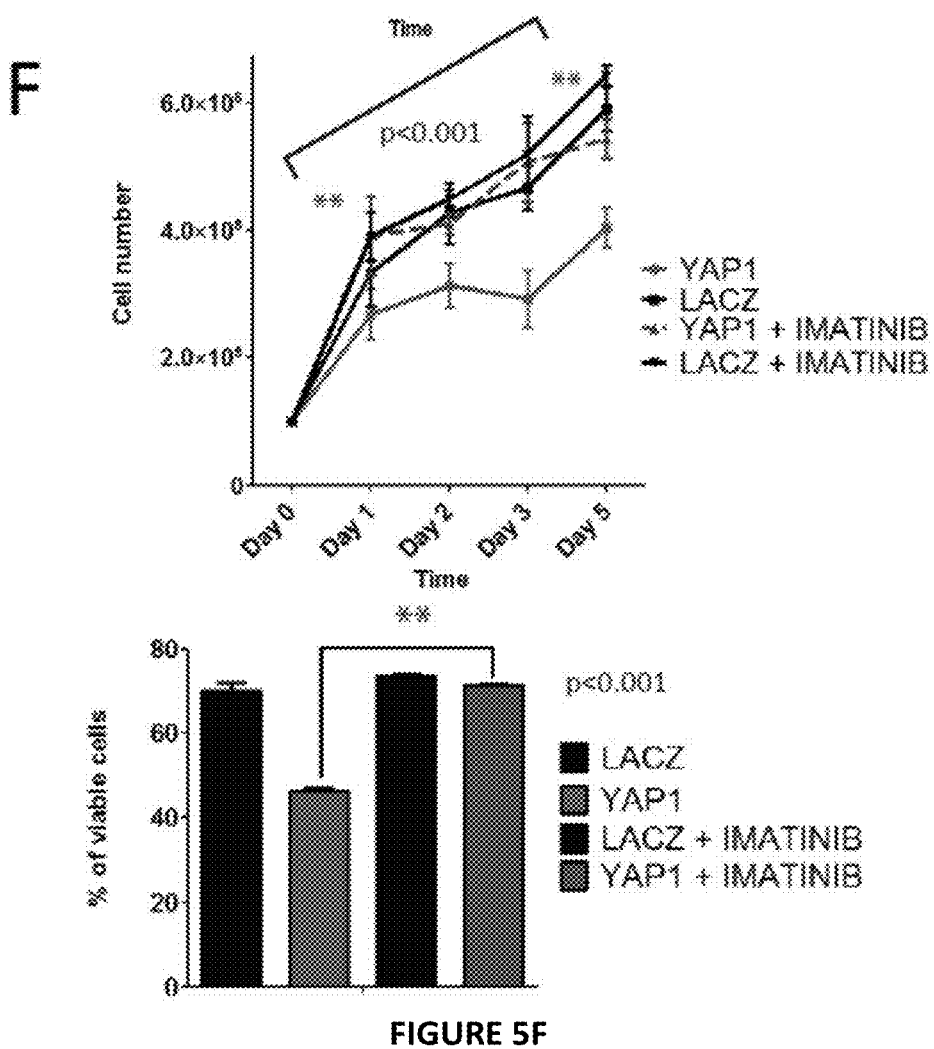
Figure 5G:
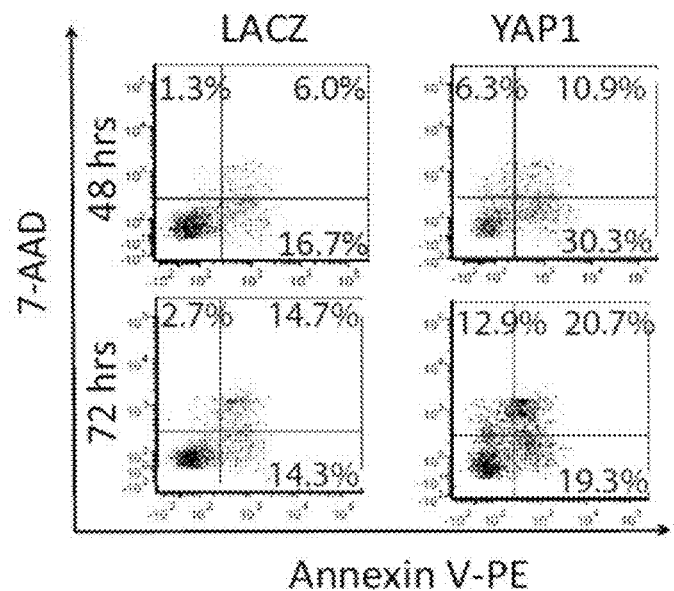
Figure 5H:
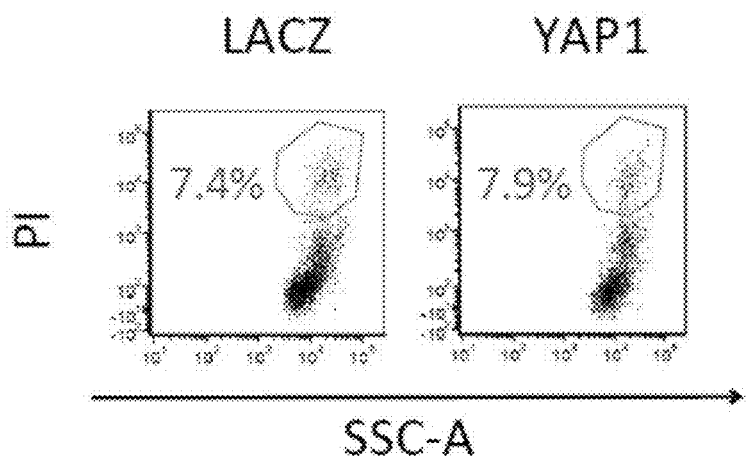
Figure 5I:
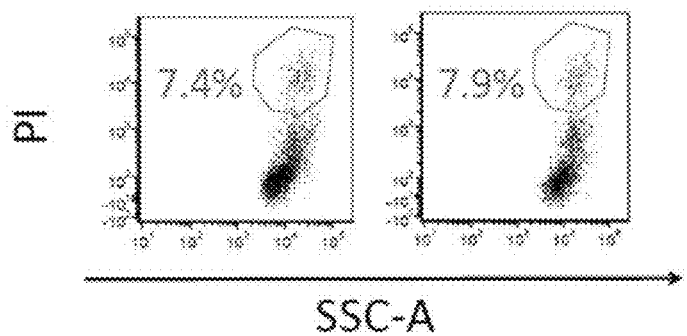
Figure 5J:
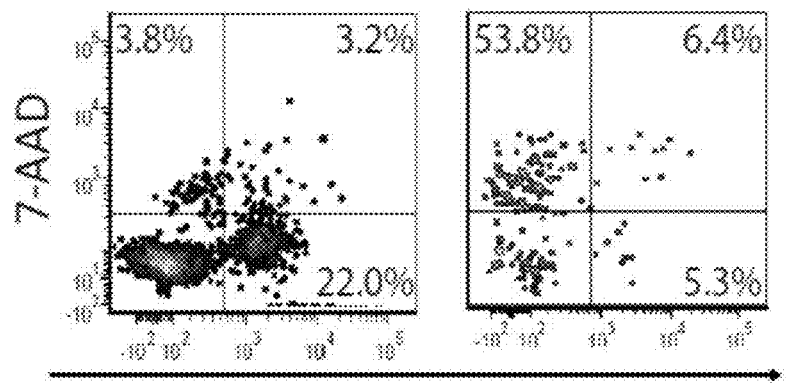

FIG. 5H and FIG. 5J—Apoptosis is measured after Annexin V-PE-7AAD staining, gating on GFP-positive KMS-20 cells (A) or MM.1S cells (C) at 48 hours and 72 hours after transfection with pLENTI4-YAP1-EGFP versus control pLENTI4-LACZ and in MM.1S.

Figure 5K:
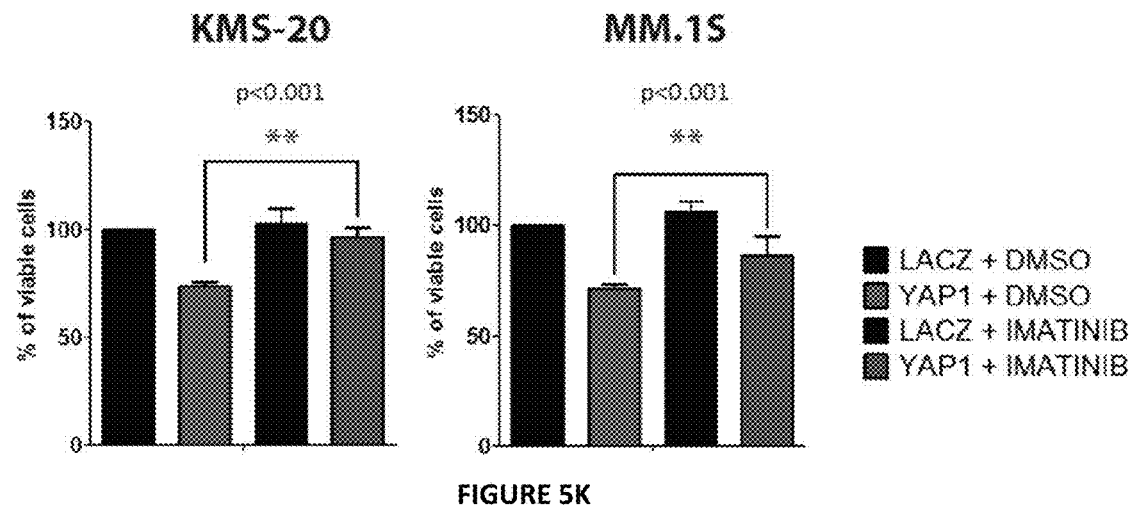

FIG. 5I—Apoptosis by PI staining in RPMI-8226 MM cells after transfection with pLENTI4-YAP1-EGFP versus control pLENTI4-LACZ using AMAXA electroporation technique FIG. 5K—Cell viability is measured by MTT absorbance assay in KMS-20 and MM.1S transfected cells described in FIG. 5A and FIG. 5E after treatment with 10 μM imatinib initiated at day 0 of transfection. Percentage of viable cells was calculated normalizing to absorbance values of LACZ+ DMSO. Mean values±SD of triplicates of two experiments are shown. **corresponds to p<0.001. 48 hour viability KMS-20: YAP1: 73.8%±4.5%; LACZ+imatinib: 102.9%±15.2%; YAP1+imatinib: 96.7%+8.9%; 48 hour viability MM.1S: YAP1: 71.4%+4.1%; LACZ+imatinib: 106.2% 10.3%; YAP1+imatinib: 86.1%±20.6%.

SUPPLEMENTAL FIGURE 6C.

Figure 6A:
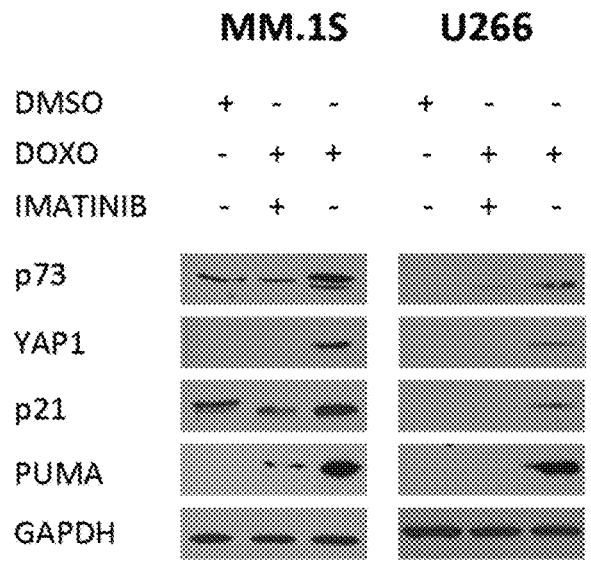
FIGS. 6A-6B. p73 expression and functional role in MM
Figure 6B:
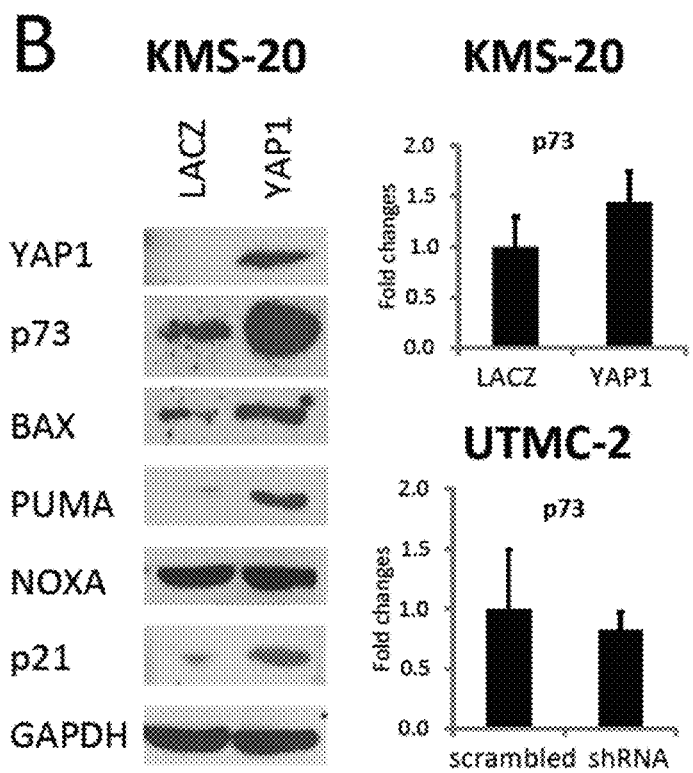
Figure 6C:
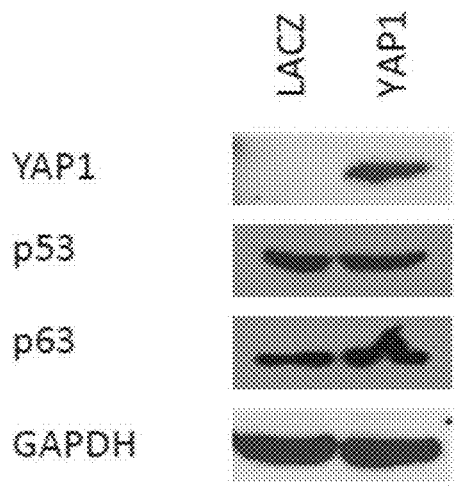

FIG 6C—Western blot analysis for p53 and p63 in KMS-20 pLENTI4-YAP1-EGFP and KMS-20 LACZ transfected cells.

SUPPLEMENTAL FIGURES 7F-7I.

Figure 7A:
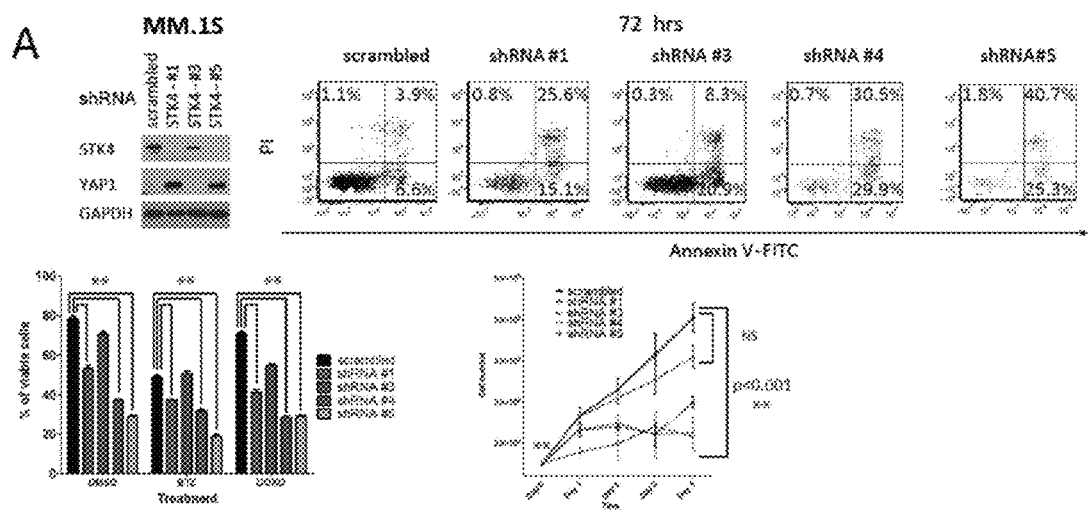
FIGS. 7A-7E. STK4 blockade by shRNAs and specific inhibitors triggers YAP1 re-expression and reduces MM cell growth FIG. 7A—STK4 silencing using lentiviral delivery system (after 48 hrs puromycin selection). Upper panel (from left to right): Western blot showing YAP1 and STK4 protein levels in STK4 silenced cells (3 representative shRNAs); Annexin V-FITC/PI staining. Lower panel: Apoptosis in stable infected cells after 48 hours incubation with various compounds (triplicate of two experiments) and growth curve in basal conditions.
Figure 7B:
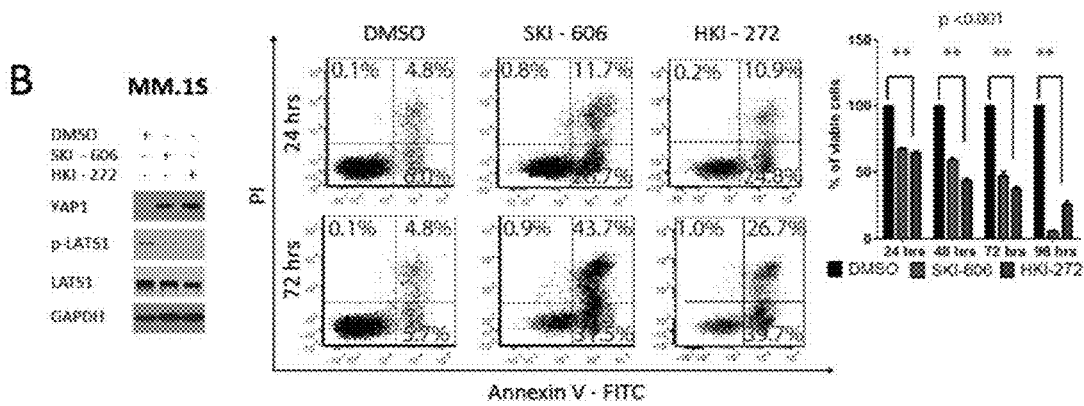
Figure 7C:
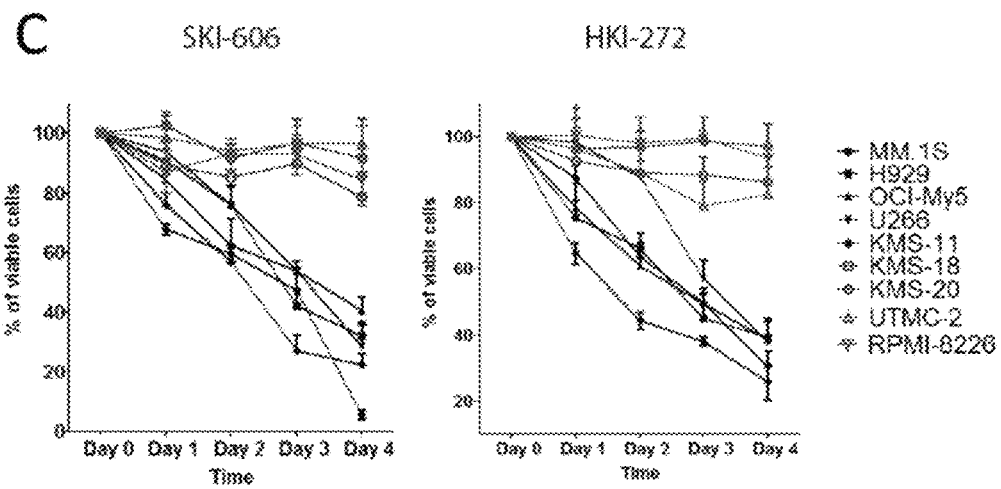
Figure 7D:
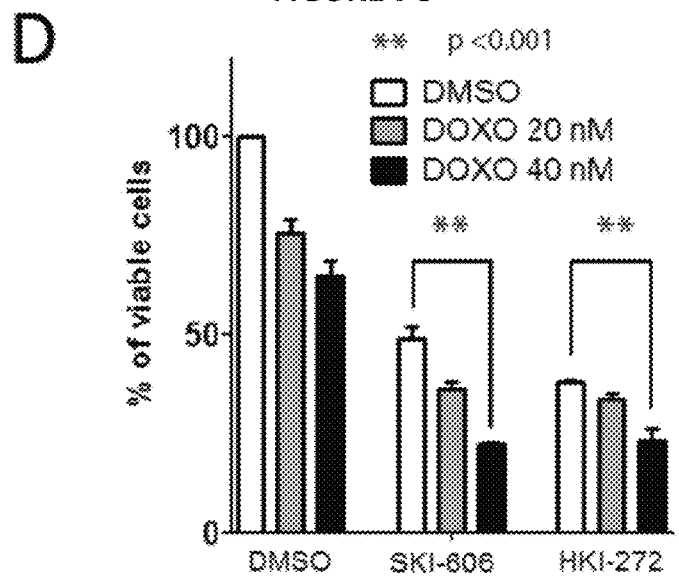
Figure 7E:
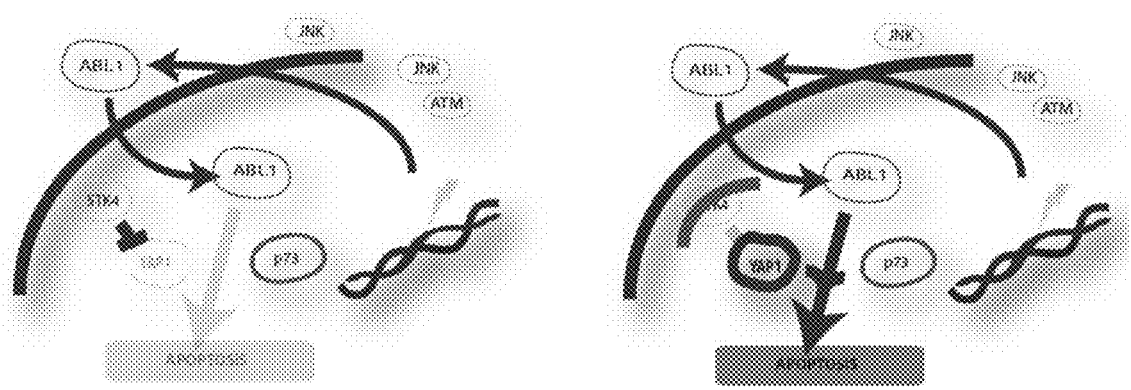
Figure 7F:
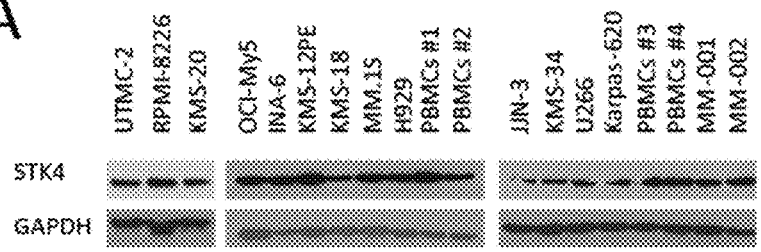

FIG. 7F—Western blot analysis of STK4 in MM cell lines, patient MM cells, and PBMCs. GAPDH is used as loading control.

Figure 7G:
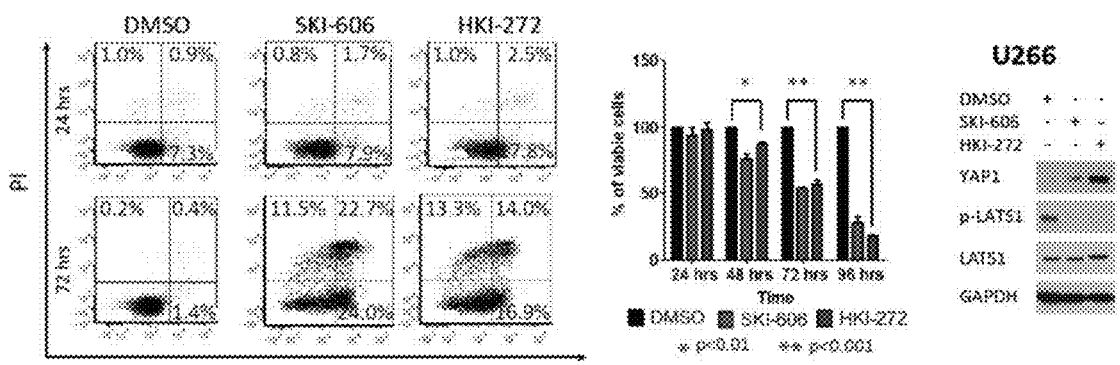

FIG. 7G—U266 cell line was treated with 10 μM SKI-606 and 10 μM HKI-272 for 24 hours and 72 hours. Apoptosis was detected by Annexin V-PI staining. Growth inhibitory effects were evaluated using MTT absorbance assay. Mean values±SD of triplicate of two experiments are shown. 24 hour viability: SKI-606: 93.8%+12.1%% and HKI-272: 98.2%±10.6%; 48 hour viability: SKI-606: 76.1%±5.8% and HKI-272: 87.8%±2.1%; 72 hour viability: SKI-606: 53.8%±1.2% and HKI-272: 56.9%+5.7%; 96 hour viability: SKI-606: 28.5%±7.4% and HKI-272: 17.9%±2.2%. Percentage of viable cells was calculated normalizing to absorbance values of DMSO. Total lysates obtained at 24 hours and were blotted with YAP1, phospho-LATS1 and total LATS1, and GAPDH as loading control, antibodies.

Figure 7H:
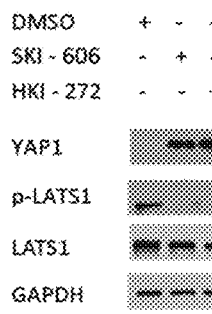

FIG. 7H—Western blot for YAP1, phospho-LATS1, LATS1 and GAPDH using lysates obtained from H929 cell after 24 hour-incubation with 10 μM SKI-606 and 10 μM HKI-272.

Figure 7I:
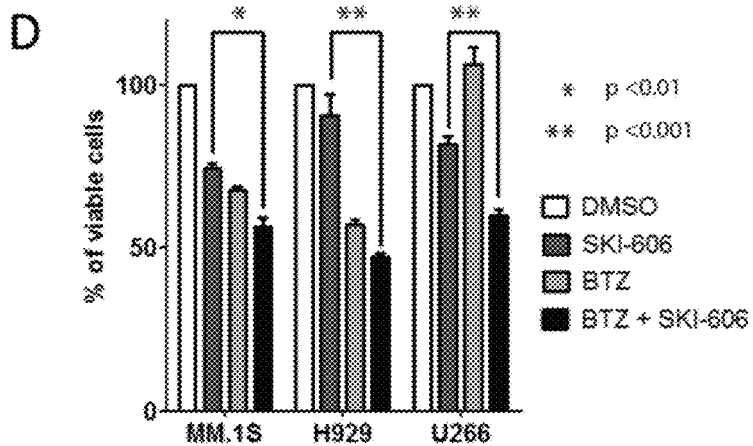

FIG 7I—MM.1S, H929, and U266 MM cells were cultured for 24 hours with DMSO or 10 μM SKI-606, in the presence or absence of 2.5 BTZ. Cytotoxicity was assessed as in (G).

SUPPLEMENTAL FIGURE 8E.

Shows a map of pLenti4'V5-DEST™ Gateway® Vector

SUPPLEMENTAL FIGURES 9E-9J.

Figure 9E:
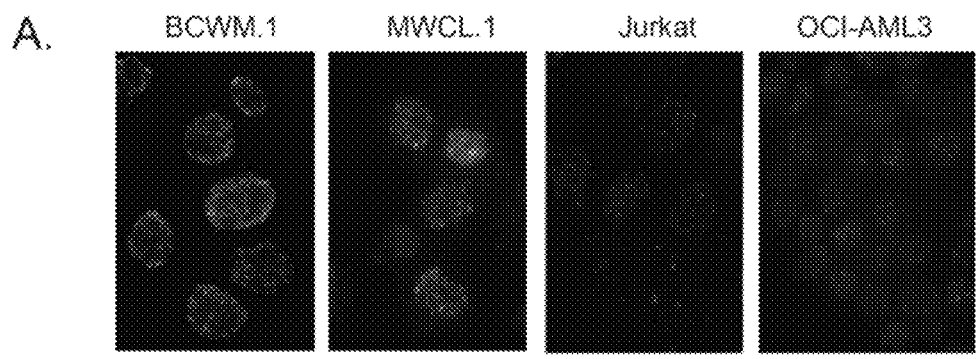
FIGS. 9A-9D show representative STK4 nucleotide and amino sequences

FIG. 9E—γ-H2A.X and nuclear content (DAPI) immunofluorescence staining on 2 waldestrom macroglobulinemia cell lines, Jurkat (T-ALL) and OCI-AML3 (AML)

Figure 9F:
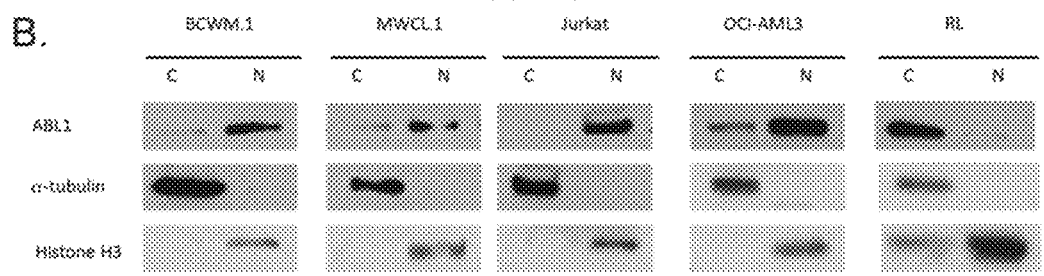

FIG. 9F—Subcellular fractionation of 2 waldestrom macroglobulinemia cell lines, Jurkat, OCI-AML3 and RL cell line. Cell lysates from cytoplasmic (C) and nuclear (N) fractions were analyzed by Western blot for ABL1 expression. α-tubulin and Histone H3 were used as loading controls for C and N fractions, respectively.

Figure 9G:
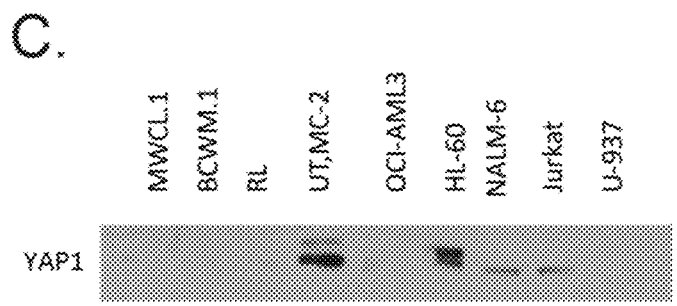
Figure 9H:
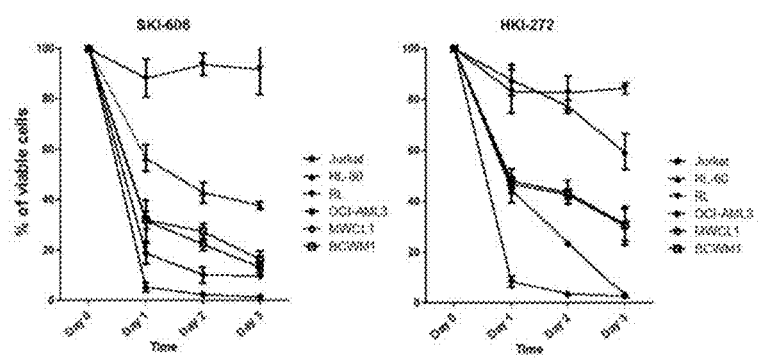
Figure 9I:
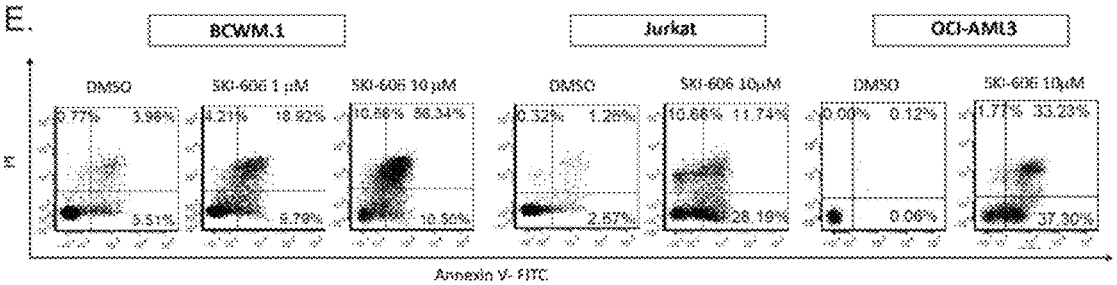

FIG. 9G—YAP1 expression levels in a panel of cell lines derived from hematological disorders FIG. 9H—Cytotoxic effects for SKI-606 and HKI-272 tested by MTT assay in different leukemia and lymphoma cell lines FIG. 9I—BCWM.1, WMCL.1, Jurkat and OCI-AML3 cell lines were treated with 1-10 μM SKI-606 for 24 and 48 hours and 72 hours. Apoptosis was detected by Annexin V-PI staining FIG. 9J—YAP1 expression levels after treatment with 10 μM SKI-606 in a panel of leukemia and lymphoma cell lines

DETAILED DESCRIPTION

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, N.Y. Each of these general texts is herein incorporated by reference.

YAP1

YAP1 is a protein and the term YAP1 as used herein encompasses homologues and fragments of YAP1 as well as derivatives of YAP1. In particular, the term YAP1 as used herein encompasses YAP1 isoforms such as the 4 different YAP1 mRNA isoforms. In preferred embodiments of the present invention the YAP −1 isoform is isoform 1 or 2. Isoform 1 has NCBI protein accession numbers NM_001130145 and NP_001123617.1 and isoform 2 (YAP 2) has NM_006106 and NP_006097.

STK4

STK4 is a protein and the term STK4 as used herein encompasses homologues and fragments of STK4 as well as derivatives of STK4. In particular, the term STK4 as used herein encompasses the STK4 homologue STK 3. STK4 has NCBI protein accession numbers NM_006282.2 and NP_006273.1 and STK3 has NCBI protein accession numbers NM_006281 and NP_006272.2. Further, caspase 3-mediated cleavage of STK4 has been reported, generating a 34KD isoform and the term STK4 encompasses both the full form and short isoform of STK4.

STK4 inactivators that are useful in the invention enable YAP1 levels to be increased in hematopoietic cells that have reduced YAP1 levels. These inactivators may be STK4 antagonists. As used herein, "antagonist" is understood within the scope of the invention to include any agent, which may include any compound, substance or molecule, e.g. a protein, polypeptide or polypeptide fragment capable of antagonising STK4's ability to reduce YAP1 levels.

ABL1

ABL1 is a protein that is a tyrosine kinase that has been implicated in processes of cell differentiation, cell division, cell adhesion, and stress response. ABL1 is a protein and the term ABL1 as used herein encompasses homologues and fragments of ABL1 as well as derivatives of ABL1. ABL1 has NCBI protein accession numbers NM_005157.4 and NP_005148.2.

Hematopoietic Disorder

The term "hematopoietic disorder" as used herein refers to any type of disorder that affects hematopoietic cells. These include but are not limited to hematopoietic cancers. Non limiting examples of hematopoietic cancers include multiple myeloma, leukaemias and lymphomas. A non-limiting list of further hematopoietic disorders is provided below:

Aplastic Anemia, Myelodysplasia, and Related Bone Marrow Failure Syndromes
Polycythemia Vera and Other Myeloproliferative Diseases
Acute and Chronic Myeloid Leukemia
Malignancies of Lymphoid Cells
Less Common Hematologic Malignancies
Plasma Cell Disorders
Multiple Myeloma Multiple myeloma is a malignant neoplasm of plasma cells in the bone marrow associated with an overproduction of monoclonal (M)-protein often causing characteristic osteolytic lesions, anemia, renal failure, and hypercalcemia. (Kyle R A et al. Multiple myeloma. N Engl J Med 2004; 351(18): 1860-1873) Monoclonal gammopathy of unknown significance (MGUS) is an asymptomatic plasma cell dyscrasia that is present in more than 3% of the general white population older than age 50 and has an average multiple myeloma progression risk of 1% per year. (Kyle R A et al. Prevalence of monoclonal gammopathy of undetermined significance. N Engl J Med 2006; 354(13):1362-1369). Smoldering multiple myeloma (SMM) is another asymptomatic plasma cell disorder but carries a higher risk of progression to frank multiple myeloma (10% per year the first 5 years) compared with MGUS. (Kyle R A et al. Clinical course and prognosis of smoldering (asymptomatic) multiple myeloma. N Engl J Med 2007; 356(25):2582-2590).

It will be appreciated that the present invention is useful for MGUS and SMM as well as multiple myeloma.

Leukaemia

Leukaemias are described as lymphoid or myeloid leukaemias, depending on which type of hematopoitic cell the abnormal leukaemia cells develop from. Leukaemias start in the bone marrow and the abonormal cells can spread from there into the bloodstream and to other parts of the body. Non limiting examples of leukaemia include acute lymphoblastic leukaemia (ALL), adult T cell leukaemia (ATL), acute myeloblastic leukaemia (AML), chronic lymphocytic leukaemia (CLL) and chronic myeloid leukaemia (CML).

Lymphoma

Lymphomas start in lymphocytes. Abnormal lymphocytes can build up in lymph nodes, bone marrow and/or the spleen. Non limiting examples of lymphomas include non-Hodgkin's lymphomas such as Waldestrom Macroglobulinemia, Burkitt lymphoma, Mantle cell lymphoma, diffuse large B cell lymphoma and follicular lymphoma.

Hematopoietic Cells

The term "hematopoietic cells" as used herein includes all the blood cell types including those from the myeloid lineage (monocytes and macrophages, neutrophils, basophils, eosinophils, erythrocytes, megakaryocytes/platelets, dendritic cells), and lymphoid lineages (T-cells, B-cells, NK-cells).

Sample

A "sample" in the context of diagnostic and prognostic methods is understood within the scope of the invention to refer to a sample which is derived from a subject. The biological sample may be obtained directly from the subject or may be derived from cultured cells obtained from said subject. Preferably the sample will include hematopoietic cells.

A non-limiting list of samples includes bone marrow aspirates or bone marrow biopsy (for myeloma, leukemias and other hematopoietic disorders), lymph node samples (for lymphomas and other hematopoietic disorders) and peripheral blood samples (for leukemias and other hematopoietic disorders). The sample may be of a particular type of hematopoietic cell, for example a population of T lymphocytes.

A "sample" in the context of screening assays is understood within the scope of the invention to refer to a suitable cell, group of cells, animal model or human. These samples do not have to be derived from a subject. A sample in this context can be a group of cells from a cell line. Preferably cell lines are derived from a hematopoietic disorder.

Protein

A "protein" such as a YAP1, STK4 or ABL-1 protein, is understood within the scope of the invention to include single-chain polypeptide molecules, as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. Portions of the protein may be referred to as a "subunit" or a "domain" or "fragment" as applicable.

The term protein also encompasses proteins that have been modified e.g. glycoproteins, lipoproteins etc.

Subject

A "subject" refers to either a human or non-human animal Examples of non-human animals include vertebrates, e.g., mammals, such as non-human primates (particularly higher primates), dogs, rodents (e.g., mice, rats, or guinea pigs), pigs and cats, etc. In a preferred embodiment, the subject is a human.

By a healthy subject it is meant a corresponding subject that does not have a hematopoietic disorder.

Detecting YAP1 and STK4 Levels and Nuclear ABL1 Relocalisation

Methods of the present invention involve detecting YAP1 levels. This can be measured at the RNA and/or protein level.

For detection at the RNA level, RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilising ribonucleic acid hybridisation include nuclear run-on assays, RT-PCR, quantitative PCR, RNase protection assays (Melton et al., Nuc. Acids Res. 12:7035), Northern blotting and In Situ hybridization. Gene expression can also be detected by microarray analysis. Such techniques are well known in the art.

For detection at the polypeptide level, altered protein levels may also be detected by measuring the YAP1 polypeptides. This may be achieved by using molecules which bind to the YAP1 polypeptides.

The above techniques may also be used to detect STK4 expression in screening methods of the present invention.

Nuclear localisation of ABL1 may be measured at the protein level. This may be achieved using molecules which bind to ABL1 polypeptides.

Suitable molecules/agents which bind either directly or indirectly to the polypeptides in order to detect the presence of the YAP1, STK4 or ABL1 include naturally occurring molecules such as peptides and proteins, for example antibodies, or they may be synthetic molecules. The polypeptides may be detected by immuno-assays, flow cytometry, PET, SELDI-TOF MS or 2-D PAGE. A non-limiting list of immuno-assays includes enzyme-linked immunosorbent assay (ELISA), radioimmuno-assay (RIA), immunofluorescence assay (IFA), enzyme linked assay (EIA) and luminescence immuno-assay (LIA), Western Blot assay (WB). Flow cytometry may be used in conjunction with an intracellular staining protocol.

Nuclear localisation of ABL1 may be detected using molecules which bind to ABL1 polypeptides together with molecules which bind to components of the nucleus such as nuclear proteins and DNA. Cells may also be treated to separate nuclei from the cytosol to enable ABL1 levels in nuclei to be compared to the cytosol using techniques known in the art. The localisation of ABL1 in the nucleus may also be detected using techniques such as immunohistochemistry.

Antibodies

An "antibody" is understood within the scope of the invention to refer to an antibody that is an intact molecule as well as fragments or portions thereof, such as Fab, F(ab')2, Fv and scFv.

YAP1 antibodies and ABL1 antibodies may be derived from commercial sources or through techniques which are familiar to those skilled in the art. Methods for production of antibodies are known by those skilled in the art.

If polyclonal antibodies are desired, a selected mammal (e.g. mouse, rabbit, goat, horse, etc.) is immunised. Serum from the immunised animal is collected and treated according to known procedures. If the serum contains polyclonal antibodies to other antigens, the polyclonal antibodies can be purified by immunoaffinity chromatography. Techniques for producing and processing polyclonal antisera are known in the art.

Monoclonal antibodies directed against antigens used in the invention can also be readily produced by those skilled in the art. The general methodology for making monoclonal antibodies by hybridomas is well known. Immortal antibody-producing cell lines can be created by cell fusion and also by other techniques such as direct transformation of B-lymphocytes with oncogenic DNA or transfection with Epstein-Barr virus. Panels of monoclonal antibodies produced against antigens can be screened for various properties, for example for isotype and epitope affinity An alternative technique involves screening phage display libraries where, for example, the phage express scFv fragments on the surface of their coat with a large variety of complementary determining regions (CDRs). This technique is well known in the art.

Antibodies, both monoclonal and polyclonal, which are directed against antigens are particularly useful in diagnosis, and those which are neutralising are useful in passive immunotherapy. Monoclonal antibodies in particular may be used to raise anti-idiotype antibodies. Anti-idiotype antibodies are immunoglobulins which carry an "internal image" of the antigen of the infectious agent against which protection is desired.

Techniques for raising anti idiotype antibodies are known in the art. These anti-idiotype antibodies may also be useful for treatment, as well as for an elucidation of the immunogenic regions of antigens.

Screening Methods

The present invention provides methods for identifying an agent capable of inducing apoptosis in cells associated with a hematopoietic disorder, which determine whether an agent is capable of increasing YAP1 levels.

Preferably the methods involve detecting whether an agent induces apoptosis. Apoptosis is quick and easy to identify using routine techniques such as those disclosed in the Examples herein. Thus in some embodiments of the present invention agents that are expected to increase YAP1 levels are tested to see if they induce apoptosis prior to testing whether they are capable of increasing YAP1 levels.

Preferably the methods of the invention will involve testing several candidate agents at the same time.

A candidate agent may first be identified as an STK4 inactivator. The STK4 inactivator may reduce expression of STK4 or be an STK4 antagonist.

Screening for STK4 Inactivators that Reduce Expression of STK4 shRNAs consist of short inverted repeats separated by a small loop sequence and this is rapidly processed by the cellular machinery into 19-22 nt siRNA, thereby suppressing the target gene expression. These can be introduced into cells using techniques known in the art.

For example, cells can be transfected using a plasmid or transducing a viral vector encoding a short hairpin RNA (shRNA) driven by a RNA polymerase (pol) III promoter, including U6, H1, 7SK and tRNA promoters (Brummelkamp T R et al., A system for stable expression of short interfering RNAs in mammalian cells. Science 296: 550-553, 2002, Gou D et al Gene silencing in mammalian cells by PCR-based short hairpin RNA. FEBS Lett 548: 113-118, 2003, Paul C P et al Effective expression of small interfering RNA in human cells. Nat Biotechnol 20: 505-508, 2002, Sui G et al. A DNA vector-based RNAi technology to suppress gene expression in mammalian cells. Proc Natl Acad Sci USA 99: 5515-5520, 2002), or a pol II promoter such as CMV or SP-C (Gou D et al Gene silencing in alveolar type II cells using cell-specific promoter in vitro and in vivo. Nucleic Acids Res 32: e134, 2004, Stegmeier F et al. A lentiviral microRNA-based system for single-copy polymerase II-regulated RNA interference in mammalian cells. Proc Natl Acad Sci USA 102: 13212-13217, 2005).

U.S. patent application Ser. No. 12/192,356 (published as 2009-0087910 A1) describes the advantages of such systems to include first the use of plasmid to express shRNA is fairly inexpensive and has been shown to achieve long-term target gene suppression in cells and whole organisms. Second, the efficient delivery and stable integration of these shRNA expression cassettes into the host genome can be efficiently achieved by using various viral systems. Third, inducible or cell-specific gene silencing can be obtained in vivo by using a DNA-based shRNA vector.

U.S. patent application Ser. No. 12/192,356 (published as 2009-0087910 A1) demonstrates that shRNA sequences can be routinely designed for silencing a gene whose sequence is known.

miRNAs are small (22-25 nucleotides in length) noncoding RNAs that can effectively reduce the translation of target mRNAs by binding to their 3' untranslated region (UTR). These can also be used to reduce expression of genes using techniques known in the art.

Agents that increase YAP1 levels may also include agents that affect ubiquitylation, sumoylation and acetylation.

Inactivators that reduce expression of STK4 may be tested using cells that naturally express STK4. Alternatively STK4 can be identified using cells that are transformed using an STK4 expression vector. This can for example be achieved by:
  i) transforming cells with a STK4 expression vector;
  ii) applying candidate agents to the transfointed cells;
  iii) investigating whether the expression of STK4 in the cells is reduced or not, compared with that in control cells (which have not had candidate agents applied to them).

The expression vector can be introduced in normal cells or cells associated with a hematopoietic disorder using any transformation method known in the art.

Inactivators that reduce expression of STK4 may also be tested using cell-free systems such as cell-free translation systems instead of cells. These systems may involve the use of cellular compartments, such as a membrane, cell envelope or cell wall.

The levels of STK4 expression may be determined at the protein or mRNA level using techniques disclosed for measuring YAP1 levels.

Screening for STK4 Inactivators that are Antagonists of STK4

STK4 is a kinase, thus STK4 antagonists can be identified using methods known in the art for screening for kinase antagonists. These involve detecting whether agents are capable of inhibiting STK4 phosphorylation. Such techniques can involve:
  i) providing a first reaction mixture comprising STK4 and an STK4 phosphorylation substrate in conditions that permit STK phosphorylation;
  ii) administering a candidate agent to the first reaction mixture;
  iii) determining phosphorylation of the STK4 phosphorylation substrate;
  iv) providing a second reaction mixture comprising STK4 and an STK phosphorylation substrate in conditions that permit STK phosphorylation wherein said candidate agent is not administered to said second reaction mixture; and
  v) comparing the phosphorylation level of the STK4 substrate in the first reaction mixture with the phosphorylation level of the STK4 substrate in the second reaction mixture, wherein a decrease in phosphorylation level of the STK4 substrate indicates ability of said agent to act as an STK4 antagonist.

Phosphorylation of STK4 targets such as Axltide can be detected using techniques known in the art.

Several such agents may be tested together using arrays, microarrays and the like.

An example of a high throughput assay that measures kinase activity is provided in example the online version of Anastassiadis et al., 2011 article which is copied below:

"In vitro profiling of the 300 member kinase panel was performed at Reaction Biology Corporation (www.reactionbiology.com, Malvern, Pa.) using the "HotSpot" assay platform. Briefly, specific kinase/substrate pairs along with required cofactors were prepared in reaction buffer; 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2). Compounds were delivered into the reaction, followed, ~20 minutes later by addition of a mixture of ATP (Sigma, St. Louis Mo.) and 33P ATP (Perkin Elmer, Waltham Mass.) to a final concentration of 10 µM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. IC50 values and curve fits were obtained using Prism (GraphPad Software). Kinome tree representations were prepared using Kinome Mapper (http://www.reactionbiology.com/apps/kinome/mapper/LaunchKinome.htm)".

While this method was designed to test kinase selectivity of a variety of kinases using a variety of substrates, it will be appreciated that the above method can be readily adapted for testing several candidate agents for their activity in relation to antagonising STK4 phosphorylation of a single substrate such as Axltide.

Other techniques for detecting phosphorylation of STK4 substrates an include the use of antibodies that recognise the phosphorylated form of STK4 substrates to enable immunassays for example to be performed. These techniques are well known in the art (see for example Yao Z, Seger R., Immunological detection of phosphorylation, Curr Protoc Cell Biol. 2001 May; Chapter 14:Unit 14.2). Phosphorylation may also be detected using 2D-gel analysis.

Candidate agents suitable for STK4 antagonist screens may also be found using high-throughput screening techniques (which are known in the art) of available large-compound libraries or through known structure-based (de novo) ligand design methodologies (see e.g. Lenz G R, Nash H M, Jindal S 2000 Chemical ligands, genomics and drug discovery. Drug Discov Today 5:145-156). Agents that are predicted to bind to STK4 are preferred candidates. Techniques for identifying proteins that bind to a particular protein are also known in the art.

Agents that are known to inhibit other kinases are also preferred candidates. See for example the techniques used in Anastassiadis et al., 2011 and Davis et al., 2011.

Determining Whether an Agent is Capable of Increasing YAP1 Levels

Agents, including those that have already been identified as STK4 inactivators using methods described above, can be tested for their ability to induce apoptosis in hematopoetic cells by applying the agents to suitable cells to see whether YAP1 levels are increased. This involves administering the agent to samples that comprise cells associated with a hematopoietic disorder or cells of cell lines that are derived from cells associated with a hematopoietic disorder. These cells will have been previously identified as having reduced YAP1 levels. Preferably these cells will also have been previously identified as having ABL1 present in their nucleus.

Introduction of Polypeptides, Polypeptide Fragments and Nucleic Acid Sequences into Cells An agent for use in the invention may be a polypeptide or a polynucleotide. Polynucleotides and polypeptides may also need to be introduced into cells as part of the screening assays of the present invention.

Where the invention makes use of a polypeptide, they may be administered directly e.g. as the polypeptide itself or by introducing nucleic acid constructs/viral vectors encoding the polypeptide into cells under conditions that allow for expression of the polypeptide in a cell of interest.

Transfer of the polynucleotide, polypeptide may be performed by any of the methods known in the art which physically or chemically permeabilize the cell membrane or by the use of liposomes. Cell-penetrating peptides may also be used to transfer a polypeptide into a cell.

The polynucleotides for use in the invention may be contained in a gene transfer vector. The vector of the may be delivered to a target site by a viral or non-viral vector. Non-limiting examples of a suitable virus vector include adenovirus, adeno-associated virus, and a retrovirus including lentivirus.

The vector may be an expression vector. Expression vectors as described herein comprise regions of nucleic acid containing sequences capable of being transcribed. Thus, sequences encoding mRNA, tRNA and rRNA are included within this definition.

Expression vectors preferably comprise a polynucleotide for use in the invention is preferably operably linked to a control sequence that is capable of providing for the expression of the coding sequence by the host cell. The term "operably linked" means that the components described are in a relationship permitting them to function in their intended manner. A regulatory sequence "operably linked" to a coding sequence is ligated in such a way that expression of the coding sequence is achieved under condition compatible with the control sequences. The control sequences may be modified, for example by the addition of further transcriptional regulatory elements to make the level of transcription directed by the control sequences more responsive to transcriptional modulators.

Non-viral delivery systems include but are not limited to DNA transfection methods and calcium phosphate precipitation. Here, transfection includes a process using a non-viral vector to deliver a gene to a target mammalian cell. Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

Administration

Even though the agents for use in the present invention can be administered alone, they will generally be administered in admixture with a pharmaceutical carrier, excipient or diluent, particularly for human therapy.

Dosage

A person of ordinary skill in the art can easily determine an appropriate dose of one of the instant agents to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

It is to be appreciated that all references herein to treatment include curative, palliative and prophylactic treatment.

The treatment of mammals is particularly preferred. Both human and veterinary treatments are within the scope of the present invention.

Combinations

In a particularly preferred embodiment, the one or more agents for use according to the invention are administered in combination with one or more other active agents, for example, existing drugs available on the market. In such cases, agents may be administered consecutively, simultaneously or sequentially with the one or more other active agents.

The major advantages of combining chemotherapeutic drugs are that it may promote additive or possible synergistic effects through biochemical interactions and also may decrease the emergence of resistance.

EXAMPLES

Methods

Materials, Reagents and Cell Lines

All the antibodies and assay reagents were obtained from commercial sources. All the MM cell lines were purchased from American Type Culture Collection (ATCC), established in our laboratory or kindly provided by our collaborators.

Antibodies

YAP1 antibody (used for western blot purposes as in FIG. 4E) was obtained from Cell Signaling ID #4912 http://www.cellsignal.com/products/4912.html ABL1 antibody (used for both western blots and IHC): Santa Cruz, sc-131 (K12) http://www.scbt.com/datasheet-131-c-abl-k-12-antibody.html Reagents Bortezomib and doxorubicin were purchased from Selleck Chemicals LLC and Sigma, respectively; ATM inhibitor (Ku55933) and JNK inhibitor (SP600125) were obtained from Calbiochem. Imatinib, an ABL1 inhibitor, was purchased from Novartis. SKI-606 and HKI-272, both kinase inhibitors, were provided by Dr. Nathanael Gray (Dana Farber Cancer Institute, Boston).

Cell Lines and Culture

The MM cell lines UTMC2, EJM, U266, H929, RPMI-8226, KMS-11, KMS-12PE, KMS-18, KMS-20, KMS-34, OCI-My5, JJN-3 and Karpas-620 were available in the labs, kindly provided by other researchers or purchased from American Type Culture Collection (ATCC). MM Dex-sensitive (MM.1S) or resistant (MM.1R) human MM cell lines were kindly provided by Dr. Steven Rosen (Northwestern University, Chicago, Ill.). IL-6-dependent INA-6 cell line was provided by Dr. Renate Burger (University of Kiel, Germany). UTMC-2 and EJM human MM cell lines were established in our laboratory. BCWM1, an IgM secreting lymphoplasmacytic cell line was obtained from a patient with WM. The BCWM1 was a kind gift from Dr. Treon (Dana-Farber Cancer Institute, Boston, Mass.). Jurkat, R L, HL-60 and U-937 were purchased from ATCC and OCI-AML3 and NALM-6 cells from DSMZ (Deutsche Sammlung von Mikroorganismen und Zellkulturen GmbH). All MM and leukemia and lymphoma cell lines were cultured in RPMI-1640 media containing 10% fetal bovine serum (FBS, Sigma Chemical Co.), 2 µM L-glutamine, 100 U/mL penicillin, 100 µg/mL streptomycin (GIBCO), with 2.5 ng/mL of IL-6 only in INA-6 cells. 293T cells, HeLa and HCT-116 cell lines were purchased from ATCC and were cultured in DMEM containing 10% fetal bovine serum (FBS, Sigma Chemical Co.), 2 µM L-glutamine, 100 U/mL penicillin, and 100 µg/mL streptomycin (P/S, GIBCO).

Primary Cells

Blood samples collected from healthy volunteers were processed by Ficoll-Paque (GE Healthcare) gradient to obtain peripheral blood mononuclear cells (PBMCs). Patient MM cells were obtained from bone marrow samples after informed consent was obtained in accordance with the Declaration of Helsinki and approval by the Institutional Review Board of the Dana-Farber Cancer Institute. Mononuclear cells were separated using Ficoll-Paque density sedimentation, and plasma cells were purified (>95% CD138+) by positive selection with anti-CD138 magnetic activated cell separation micro beads (Miltenyi Biotec).

Cell Culture and Molecular Methods

Methods for cell culture, DNA and RNA extraction, mRNA abundance evaluation, subcellular fractioning, immunoblotting, immunofluorescence, assays for viability, cellular growth and apoptosis are described below.

DNA Extraction and Genomic Deletion Evaluation by PCR

Genomic DNA was extracted using DNA extraction kit (Qiagen). To identify and confirm YAP1 deletion in MM cell lines the following primers were used:

| Primer name | Sequence |
| --- | --- |
| YAP1 exon1-F | CTTCTCCACCTCGGCCC |
| YAP1-exon1-R | TCCAGGTCGGTCTCCGAGTC |
| YAP1-exon4-F | CATCGAATATCCCAAATTGC |
| YAP1-Intron4/5-R | CAAAAGTGGAAGGCTGGTT |
| YAP1-exon7-F | CAGCCCTGATGTTAGCTTTTC |
| YAP1-exon7-R | AAATTTCCGGTGCATGTGTC |

Starting with 100 ng of genomic DNA, the following protocol was used: 94° C. for 30 sec as initiation step; 94° C. for 15 sec as denaturating phase; 58° C. or 59° C. for 15 sec, according to primer set used, as annealing step; 72° C. for 1 min as elongation step; repeating them for 25-30 cycles; and then 72° C. for 5 min as final elongation. PCR products were visualized on 1.0% TAE agarose gel after running for 1 hour.

RNA Extraction and Reverse Transcription Polymerase Chain Reaction

RNA was extracted using Trizol (Invitrogen) and quantified by a Nanodrop spectrophotometer (Labtech). Specifically, 5×106 cells were pelleted, washed with cold PBS, and resuspended in 1 mL Trizol. They were then incubated with 1-Bromo-3-chloropropane (Sigma), washed first with Isopropyl alcohol and then with 75% Ethanol, and resuspended in Nuclease Free-water (Invitrogen). After quantification, 2000 ng of RNA was used to synthesize cDNA via the Superscript II First strand synthesis Kit (Invitrogen), according to the manufacturer's instructions. To evaluate the expression levels of YAP1, p'73, ABL1 and GAPDH reverse transcription polymerase chain reaction (RT-PCR) was performed using SYBR GREEN PCR Master Mix (Applied Biosystem), after optimization of the primer conditions. cDNAs were diluted 1:100 or 1:1000 and amplified in a 20 µL reaction. Primers were used at 200 nmol or 400 nmol concentration. Thermal cycling conditions were: 10 minutes at 95° C., 40 cycles at 95° C. for 15 seconds, followed by 1 minute at 60° C. Real-time quantitative PCR was performed on ABI Prism 7300 Sequence Detection System (Applied Biosystems). Data were analyzed using the delta delta Ct method. GAPDH was used as a loading control.

| Primer name | Sequence |
|---|---|
| YAP1-F | CAATAGCTCAGATCCTTTCCT |
| YAP1-R | TAGTATCACCTGTATCCATCTC |
| TA-p73-F | GCACCACGTTTGAGCACCTCT |
| TA-p73-R | GCAGATTGAACTGGGCCATGA |
| ABL1-F | CCCAACCTTTTCGTTGCACTGT |
| ABL1-R | CGGCTCTCGGAGGAGACGTAGA |
| GAPDH-F | GAAGGTGAAGGTCGGAGTCA |
| GAPDH-R | GGGGTCATTGATGGCAACAATA |

Western Blotting

MM cells were harvested and lysed using lysis buffer: 50 mMTris-HCl (pH 7.4), 150 mM NaCl, 1% NP-40, 5 mM EDTA, 5 mM NaF, 2 mM Na3VO4, 1 mM PMSF, 5 µg/mL leupeptine, and 5 µg/mL aprotinin. Nuclear extracts were prepared using Nuclear Extraction Kit (Panomics). Cell lysates were subjected to sodium dodecyl sulfate-polyacrylamide gel electrophoresis SDS-PAGE, transferred to nitrocellulose membranes, and immunoblotted with different antibodies: ATM, phospho-ATM (Ser1981), ATR, phospho-ATR (Ser428), CHK2, phospho-CHK2 (Thr68), CHK1, phospho-CHK1 (Ser296), p21, p53, phospho-p53 (ser127), STK4, LATS1, phospho-LATS1 (Ser909), phospho-ABL1 (Thr735), cleaved caspase 3, cleaved PARP, histone H3, SAPK/JNK, phospho-SAPK/JNK (Thr183/Tyr185), GM130, GAPDH, and α-tubulin (Cell Signaling); STK4, Nuclear Matrix Protein p84 (Abeam), p73 (BD), phospho-H2A.X (Ser139) (Millipore); as well as ABL1, BAX, Puma, Noxa, actin and nucleolin (Santa Cruz Biotechnology).

Immunofluorescence Staining 15,000 cells from MM cell lines, PBMCs or MM patient samples were cytospun for 5 minutes at 350-500 rpm, fixed in 4% paraformaldehyde (PFA) for 15 minutes, washed three times with PBS, and incubated with 0.1M glycin for 10 minutes to quench PFA autofluorescence. After washing again, cells were permeabilized and stained for 90 minutes with a solution of 0.1% Triton X-100/PBS+BSA1% containing primary antibodies at a ratio of 1:100. Cells were washed and incubated for 45 minutes with appropriate secondary-fluorescent antibodies. Alexa Fluor 488 and Alexa Fluor 647 anti-rabbit and Alexa Fluor 488 and Alexa Fluor 568 anti-mouse antibodies were purchased from Invitrogen. After washes, the nuclear content was stained with DAPI reagent (Invitrogen) for 5 minutes and washed. The entire procedure was performed at room temperature. The slides were then mounted with ProLong Gold Antifade Reagent (Invitrogen), and images were taken using a Zeiss microscope (Carl Zeiss) equipped with Hamamatsu ORCA-ER camera (Hamamatsu Photonics) and analyzed with ImageJ software. Anti-phospho-H2A.X was obtained from Millipore, Anti-ABL1 from Santa Cruz and ANTI-cleaved caspase 3 from Cell signaling.

γ-H2A.X Foci Quantification

MM cell lines and patient MM cells were stained and images acquired as described above. For each sample, at least three different images were taken, representative of different fields of the slide. Each image contained a field of at least 30 cells. Cells were considered positive if they have more than 6 foci. Mean and standard deviation were calculated among the triplicates.

Immunohistochemistry

For immunohistochemistry on clinical samples, polyclonal antibody (code, dilution 1:200) from Santa Cruz Biotechnology (Santa Cruz, Calif., USA) was applied on 4 micron-thick sections, obtained from formalin-fixed, paraffin-embedded human specimens of multiple myeloma, after antigen retrieval Tris-EDTA at pH 9, at 970C, for 30 minutes. The reaction was developed with Ultravision detection system HRP-Polymer (Thermo Scientific, Waltham, Mass., USA) and developed with DAB (Thermo Scientific). Sections were counterstained with hematoxylin.

Stable Gene Knockdown Using Lentiviral Vectors

Lentiviral short hairpin RNAs (shRNA) were used to knockdown YAP1 and STK4 expression in MM cells. Scrambled control pLKO.1 shRNA vectors and specific YAP1 and STK4 shRNA constructs were kindly provided by Dr. William Hahn (Dana-Farber Cancer Institute).

| Primer name | Sequence |
|---|---|
| YAP1 shRNA clone #1 (SEQ ID NO: 5) | CCCAGTTAAATGTTCACCAAT |
| YAP1 shRNA clone #3 (SEQ ID NO: 6) | CAGGTGATACTATCAACCAAA |
| STK4 shRNA clone #1 (SEQ ID NO: 1) | AGTTGAGTGATAGCTGGGAAA |
| STK4 shRNA clone #3 (SEQ ID NO: 2) | GCCCTCATGTAGTCAAATATT |
| STK4 shRNA clone #4 (SEQ ID NO: 3) | GCCAAGCGGAATACAGTGATA |
| STK4 shRNA clone #5 (SEQ ID NO: 4) | CTAAGAAGAGACGGCAACAAA |

Further details of which are provided below:

| Clone ID | Clone Name | Target Gene | Target Gene Symbol | Vector | Match Position | Match Region | Target Sequence | Forward Oligo Sequence | Reverse Oligo Sequence |
|---|---|---|---|---|---|---|---|---|---|
| TRCN0000001622 SEQ ID NO 1 | NM_006282.x-1776s1c1 | 6789 | STK4 | pLKO.1 | 1776 | 3UTR | AGTTGAGT GATAGCTG GGAAA | CCGGAGTT GAGTGATA GCTGGGAA ACTCGAGT TTCCCAGC TATCACTC AACTTTTT TG | AATTCAAA AAAGTTGA GTGATAGC TGGGAAAC TCGAGTTT CCCAGCTA TCACTCAA CT |

-continued

| Clone ID | Clone Name | Target Gene | Target Gene Symbol | Match Vector | Match Position | Match Region | Target Sequence | Forward Oligo Sequence | Reverse Oligo Sequence |
|---|---|---|---|---|---|---|---|---|---|
| TRCN0000001624 SEQ ID NO 2 | NM_006282. x-287s1c1 | 6789 | STK4 | pLKO.1 | 287 | CDS | GCCCTCAT GTAGTCAA ATATT | CCGGGCCC TCATGTAG TCAAATAT TCTCGAGA ATATTTGA CTACATGA GGGCTTTT TG | AATTCAAA AAGCCCTC ATGTAGTC AAATATTC TCGAGAAT TCGAGAAT ATTTGACT ACATGAGG GC |
| TRCN0000001625 SEQ ID NO 3 | NM_006282. x-577s1c1 | 6789 | STK4 | pLKO.1 | 577 | CDS | GCCAAGCG GAATACAG TGATA | CCGGGCCA AGCGGAAT ACAGTGAT ACTCGAGT ATCACTGT ATTCCGCT TGGCTTTT TG | AATTCAAA AAGCCAAG CGGAATAC AGTGATAC TCGAGTAT CACTGTAT TCCGCTTG GC |
| TRCN0000001626 SEQ ID NO 4 | NM_006282. x-1478s1c1 | 6789 | STK4 | pLKO.1 | 1478 | CDS | CTAAGAAG AGACGGC AACAAA | CCGGCTAA GAAGAGAC GGCAACAA ACTCGAGT TGTTGCC GTCTCTTC TTAGTTTT TG | AATTCAAA AACTAAGA AGAGACGG CAACAAAC TCGAGTTT GTTGCCGT CTCTTCTT AG | p-ENTR-YAP1-EGFP plasmid: two plasmids were kindly provided by Dr. Mario Sudol. The human YAP1 full length in pCDNA3.1 was from Espanel and Sudol, Journal of Biochemical Chemistry, 2001, 276(17):14514-23. The plasmid GFP-YAP1 is from Basu et al., Molecular Cell, 2003, 11:11-23.

pLENTI4-V5DEST Vector:

The pLenti4'V5-DEST™ Gateway® Vector is a Gateway®-adapted ViraPower™ lentiviral expression vector for lentiviral-based expression of a target gene in dividing and non-dividing mammalian cells. The vector has the CMV promoter for driving constitutive expression of the target gene and the Zeocin™ selection marker for stable selection in mammalian cells. It is commercially available from Invitrogen Life Technologies. The datasheet data for this can be found at http://products.invitrogen.com/ivgn/product/V49810 and a map of this vector is shown in Figure 8E.

The efficacy of each shRNA in silencing gene expression was tested in HCT-116 and HeLa cell lines using Mirus Bio Trans-IT LT1 transfection reagent. To obtain stable silenced clones with YAP1/STK4 shRNA or pLKO.1 control plasmid, the following protocol was used. 293T cells were plated (300,000 cells on 6-cm plates) in DMEM/10% FBS/0.1% P/S. After 24 hours when cells were 60-70% confluent, 1000 ng of vector of interest together with 100 ng p-VSV-G and 900 ng delta 8.94 (both packaging vectors purchased from Addgene) were co-transfected with MIRUS BIO TransIT-LT1 diluted in OPTI-MEM (GIBCO). After 12 hours, 293T media was changed with DMEM/30% FBS/10% P/S to promote viral production. 24 and 48 hours post transfection, supernatant containing lentiviral particles was harvested, filtered with 0.45 µM diameter filter, and used to infect 2.5×10^6 MM cells. MM cells were spinoculated at 750 g for 30 minutes with 8 µg/mL polibrene, incubated with viral supernatant for 6 hours, and left in culturing media. After the second cycle of infection, cells were put under selection with a suitable concentration of puromycin. mRNA and protein expression were evaluated 48 and 72 hrs after selection. Functional studies were performed as described below.

Transient Transfection of MM Cell Lines p-ENTR-YAP1-EGFP plasmid was kindly provided by Dr. Marius Sudol and subcloned into pLENTI4-V5DEST vector using GATEWAY strategy. p-LENTI4-LACZ vector was used as control. KMS-18, KMS-20, MM.1S, RPMI-8226 and UTMC-2 cells (5,000,000) cells were transiently transfected with p-LENTI4 YAP1, using 'Cell Line Nucleofector Kit V (Amaxa Biosystems, Köln, Germany), according to the manufacturer's instructions. AMAXA program: MM.1S→T-030; RPMI-8226→C-015; KMS-18, KMS-20 and UTMC-2→X-001. Specifically, 5×106 cells were resuspended in 100 µL V solution and 2500 ng of plasmid. Following transfection, MM cells were subjected to mRNA analysis, Western blotting, as well as apoptosis, cell counting, and MTT assays.

Viability and Cellular Growth Assays

Viability of MM cells was evaluated by 3-[4,5-dimethylthiazol-2-yl]-2,5-diphenyltetrazolium bromide (MTT) colorimetric survival assay. MM cells (20,000-50,000) were plated in 100 µL medium. At the various time points (24-96 hours), 10 µL 5 mg/mL MTT were added to plated cells. After 4 hour incubation at 37° C., medium was discarded and 100 µL MTT stop solution (Isopropanonol with 1 nM Hcl) used to dissolve MTT metabolic products. Absorbance was read at 570 nm and background was subtracted at 630 nm, using spectrophotometer SPECTRAMAX M2 machine and Softmax Pro v5 software. Cellular growth was estimated by cell counting in triplicates, excluding dead cells stained by trypan blue.

Apoptosis Assays

Dead cells were detected by propidium iodide (PI) staining

Apoptosis was quantified using Annexin-V-FITC-PI staining or Annexin-V-PE-7AAD staining on GFP-positive cells (BD Biosciences). In particular, cells were washed twice with room-temperature PBS, resuspended in 100 µL of Annexin binding buffer, and stained with specific antibodies for 20 minutes. After adding other 400ℓ of Annexin binding buffer, samples were acquired using FACS Canto II machine from Becton Dickinson, BD, and analyzed with FCS EXPRESS 4 Flow Research Edition software. The percentage of cells undergoing apoptosis was defined as the sum of early apoptotic (AnnexinV+, PI−) and late apoptotic (Annexin V+PI+) cells.

Statistical Analysis

Statistical significance was determined by Student t test. The minimal level of significance was P<0.05. For YAP1 expression analysis, when more than two groups were compared, ANOVA one-way, followed by Tukey's Multiple Comparison test. Kaplan-Meier survival curves for YAP1 were obtained with www.canevolve.org based on the GSE2658 dataset, probe set 224895_at.

Results

MM Cells do not Undergo Apoptosis Despite High Levels of Ongoing DNA Damage

We first tested a panel of MM cell lines to confirm the presence of widespread DNA damage. DNA damage was assessed by immunofluorescence and western blot analysis of the phosphorylated form of H2A.X (at phospho-Ser139; γ-H2A.X)(Walters et al., 2011), which localizes and forms characteristic foci adjacent to DNA breaks and is involved also in the repair of single-strand lesions. Eleven out of 13 MM cell lines demonstrated increased γ-H2A.X staining (FIG. 1A and FIG. 1E), as did MM patient samples (FIG. 1B). MM cell lines and MM patient samples positive for γ-H2A.X also had an activated DNA damage response (DDR), evidenced by phosphorylation of the kinases ATM (Ser1981), CHK2 (Thr68), ATR (Ser428) and CHK1 (Ser296)(FIG. 1C and data not shown), further suggesting an active engagement of both ATM and ATR-dependent pathways. Notably, these DDR markers are absent in plasma cells (Walters et al., 2011) and in peripheral blood mononuclear cells (PBMCs) from healthy donors (FIG. 1A-C), indicating that the increased DDR response is specific for neoplastic plasma cells. Indeed, these findings mirror what has been reported in other cellular contexts (lung, colon, brain, and bladder cancers as well as melanoma), where the presence of DNA damage appears to discriminate normal tissues from pre-neoplastic and cancerous lesions (Bartkova et al, 2005; Gorgoulis et al, 2005). Notably, U266 and KMS-34 MM cell lines that did not show γ-H2A.X foci were also negative for all markers of DDR activation (FIG. 1C).

In normal tissues, DNA damage and DDR activation is associated with cell cycle arrest, followed by senescence and apoptosis, if the cells are unable to repair the genomic damage. Therefore, we speculated that this rampant DDR response would similarly be associated with an intense apoptosis in MM cells. Surprisingly, we did not detect any significant cell death in MM cell lines and MM patient cells under basal conditions (FIG. 1D and FIG. 1F). Specifically, FACS analysis using annexin V and propidium-iodide (PI) staining failed to show apoptosis (FIG. 1D and data not shown) in two representative MM cell lines. Similar results were obtained with immunofluorescence staining using antibodies directed against cleaved caspase 3 and γ-H2A.X, as well as after immunoblotting with cleaved caspase 3 and cleaved PARP1 antibodies. Therefore despite a high degree of ongoing DNA damage and DDR checkpoint activation, MM have mechanisms to escape the apoptotic response usually triggered in normal cells.

The Pro-Apoptotic Kinase ABL1 is Localized in the Nucleus in MM Cells

In epithelial cancers, premalignant clones consistently acquire p53 mutations to overcome the DDR checkpoint and develop into carcinomas (Bartkova et al., 2005; Halazonetis et al., 2008). In contrast, p53 genetic inactivation occurs much less frequently and is a late event in hematopoietic neoplasms including MM (Xu-Monette et al., 2012). Indeed, the modifications associated with DNA damage and DDR response were present at a comparable level in MM cells, irrespectively of the p53 mutational status (FIG. 1C and data not shown). Moreover, no evidence of consistent activation of p53, evidenced by phosphorylation of Serine 15, was evident in p53-WT cells, confirming previous reports ((Hideshima et al., 2003) and data not shown). Taken together, these data indicate that p53 inactivation in MM, and more generally the disruption of the ATM/ATR-CHK2/CHK1-p53 cascade, does not play a major role in the abrogation of apoptosis following DDR, at least in the early stages of the disease.

A second pathway involved in the apoptotic response after DSBs entails the activation of the ABL1 tyrosine kinase upon DNA damage (Kharbanda et al., 1995; Shafman et al., 1997; Yuan et al., 1997; Yuan et al., 1996). The BCR-ABL1 fusion protein present in CML and ALL exerts its oncogenic activity exclusively in the cytoplasm. In contrast, wild type ABL1 shuttles to the nucleus after genotoxic stress, thereby triggering apoptosis via a mechanism that does not require functional p53 (Taagepera et al., 1998). We found that ABL1 mRNA levels increase in MM cell lines after DNA damage (FIGS. 2E-2F) and are significantly higher in patient MM cells and MM cell lines in comparison to control normal plasma cells ((Carrasco et al., 2006; De Vos et al., 2002) and FIG. 3D). We therefore first asked whether ABL1 localized in the nucleus in MM cells. Strikingly, in the vast majority of MM cells ABL1 demonstrated a prominent and preferential localization inside the nucleus (FIG. 2A), unlike the negative control HeLa cells (FIG. 3E). Immune-histochemical stainings also confirmed the prominent ABL1 localization inside the nucleus in patient samples (FIG. 2B and FIG. 2G).

DNA Damage Activation Leads to Nuclear Accumulation of ABL1 in MM Cells Through ATM and JNK Phosphorylation.

MM cell lines U266 and KMS-34, which lack γ-H2A.X staining, did not show any ABL1 localization in the nucleus (FIG. 2A), resembling control PBMCs. These data suggest that in these cell lines the absence of DNA damage prevents ABL1 from shuttling inside the nucleus. We hence reasoned that in the majority of MM cell lines the rampant DNA damage might drive ABL1 inside the nucleus. To test this hypothesis, we used Ku55933, a compound that selectively inhibits the kinase activity of ATM (Hickson et al., 2004) induced upon exposure to DNA damaging agents, and consequently phosphorylates and activates ABL1 (Brown and McCarthy, 1997). Immunoblot analysis demonstrated a reduction in CHK2 phosphorylation at Thr68, a substrate of ATM, confirming inhibition of ATM by Ku55933 in MM cells (FIGS. 2H-2I). A panel of MM cell lines was next cultured with Ku55933 at different concentrations (2-10 μM) and for variable time intervals (1, 2, 6 and 24 hs). All the MM cell lines tested demonstrated an increase in the levels of cytoplasmic ABL1, and a concomitant strong reduction of nuclear ABL1. Similar data were obtained in both p53-WT (MM.1S, H929) as well as in p53-mutant (UTMC-2, JJN-3 and KMS-20) MM cell lines (FIG. 2C and FIGS. 2H-2I).

In response to DNA damage and ATM phosphorylation, activation of the c-Jun N-terminal kinase (JNK) induces phosphorylation of 14-3-3 proteins leading to their release from ABL1, which in turn can then shuttle inside the nucleus (Yoshida et al., 2005). Conversely, JNK inhibition leads to ABL1 retention in the cytosol. We therefore next asked whether JNK inhibition would prevent ABL1 nuclear localization in MM cells. MM cell lines (MM.1S, UTMC-2 and JJN-3) were incubated with JNK1 inhibitor SP600125 (10 µM for 2 hs). SP600125 treatment reduced nuclear ABL1 and concomitantly robustly increased cytosolic ABL1 in all MM cell lines examined (FIG. 2D).

14-3-3 signaling proteins sequester ABL1 in the cytoplasm through binding to ABL1 RSVpT$^{735}$LP motif, thus masking ABL1 nuclear localization signals (Yoshida et al., 2005) Immunoblot analysis for phospho-ABL1 revealed absent or low Thr735 ABL1 in most MM lines (FIG. 2J), suggesting that ABL1 is not phosphorylated at Thr735 and therefore not sequestered in the cytoplasm by the 14-3-3 proteins. Indeed, ATM inhibition increased the amount of phospho (Thr735) ABL1 in the cytoplasm, suggesting an active role of DNA damage in ABL1 cellular localization (FIG. 2J). Taken together, these results suggest that ongoing DNA damage in MM cells activates ATM and JNK, leading to relocalization of ABL1 into the nucleus.

ABL1 Nuclear Relocalization Leads to Increased Apoptosis in MM Cells after Treatment with DNA Damaging Agents.

Nuclear relocalization of ABL1 represents a strong pro-apoptotic signal (Taagepera et al., 1998; Yoshida et al., 2005). To determine whether nuclear ABL1 is able to induce apoptosis in MM cells, we used the U266 MM cell line, which does not show γ-H2A.X foci, pATM or nuclear ABL1 under basal conditions. Treatment with doxorubicin, a DNA-damaging agent commonly used in MM therapy, induced multiple γ-H2A.X foci and strong pATM and pJNK phosphorylation (FIG. 3A), consistent with elicited DNA damage in these cells. Moreover, ABL1 moved to the nuclear compartment (FIG. 3A), and ABL1 protein and mRNA total levels were increased (FIG. 2E). Importantly, Annexin V and PI staining revealed a marked increase (from 13.1% to 40.1%) in apoptotic cells after treatment (FIG. 3B). MTT assay also demonstrated a reduction to 50% viable cells after doxorubicin treatment.

In order to establish the role of nuclear ABL1 in inducing cell death in MM cells, we incubated U266 cell line with doxorubicin, with or without imatinib. It has been shown that pro-apoptotic activity of nuclear ABL1 is linked to its kinase activity, which can be blocked by inhibitors of its ATP binding domain (Yoshida et al., 2005). Treatment with imatinib increased U266 MM cell viability from 52.8% to 78.5% (p<0.001), with a concomitant decrease in cells positive for Annexin V-FITC PI from 40.1% to 19.9% (p<0.01) (FIG. 3B).

This assessment was next extended to other MM cell lines, first examining whether additional DNA damage could be pharmacologically induced in MM cell lines, which already have endogenous DNA damage and DSBs. To this end, the MM cell lines MM.1S and UTMC-2, both characterized by DSBs and DDR, were exposed to doxorubicin. An increase in γ-H2AX, pATM, and pJNK was evident, along with a major increase in nuclear ABL1 and apoptosis, from 12.4% to 55.3% in MM.1S cells, and from 19.1% to 57.8% in UTMC-2 cells (FIG. 3C, FIG. 3F and data not shown). Co-treatment of each cell line with doxorubicin and imatinib significantly reduced the percentage of apoptotic cells from 55.3% and 57.8% to 36% and 41.7% in MM.1S and UTMC-2 lines, respectively (p<0.05). Consistent with this data, cell viability assessed by MTT assay increased after co-treatment, from 33.3% to 72.8% in MM.1S, and from 66.5% to 79.9% in UTMC-2 cell line (p<0.001; FIG. 3C).

Interestingly, both the absolute increase in ABL1 and its enhanced relocalization were present to a similar extent in p53-WT (H929 and MM.1S) as well as in p53 mutated (UTMC-2 and JJN-3) MM cell lines (FIG. 3 A,C and data not shown).

These results are consistent with a model whereby MM cells live in a delicate equilibrium, withstanding high levels of ongoing DNA damage that activates the ATM and pJNK pathway and leads to relocalization of ABL1 into the nucleus. Strikingly, while nuclear ABL1 usually leads to apoptosis, no significant apoptosis was evident in MM cells, suggesting that additional mechanisms are engaged in MM cells to prevent their demise.

The Hippo Pathway Co-Transcription Factor YAP1 is Deleted in MM Cell Lines and MM Patient Samples and Consistently Down-Regulated.

ABL1 forms a complex with the tumor suppressor p73, a p53 homologue (White and Prives, 1999) and the Hippo pathway effector YAP1 (Yes-associated protein)(Levy et al., 2008; Sudol, 1994). YAP1 as well as its *Drosophila* ortholog, Yorkie, is the main transcriptional coactivator downstream to the Hippo (Hpo)-Salvador(Sav)-Warts(Wts) pathway and exerts a critical role in controlling organ size and regulating stem cell and progenitor cell proliferation. In response to DNA damage, ABL1 induces apoptosis through the phosphorylation of YAP1 that in turn stabilizes p73 and co-activates p73 pro-apoptotic target genes (Levy et al., 2007, 2008). Therefore we sought to determine whether the nuclear relocalization of ABL1 in MM is unable to induce apoptosis due to disruption of the ABL1/YAP1/p73 axis.

YAP1 has been reported as an oncogene in several cancers of epithelial origin (see discussion). However, exploring published gene expression array datasets, a remarkable pattern emerged: YAP1 was consistently upregulated in tumor cell lines of epithelial origin, but it was profoundly downregulated in hematologic malignancies including lymphomas, leukemias, and multiple myeloma (FIG. 4A). These data suggest that YAP1 might exert a different role in hematological cancers, including MM. Human YAP1 maps at chromosome 11, at the 11q22.1 locus, which is a site of focal, homozygous deletions in 5 to 13% MM patients. (Annunziata et al., 2007; Carrasco et al., 2006; Keats et al., 2007; Walker et al., 2010). The genes implicated as the targets of this deletion are BIRC2 and BIRC3, which are involved in the control of the pro-oncogenic NF-□B pathway (Annunziata et al., 2007; Keats et al., 2007). Reassessing previously published data by others and us (Carrasco et al., 2006; Keats et al., 2007; Walker et al., 2010), we noticed that the deletion in this locus consistently involves YAP1 in addition to BIRC2 and BIRC3 in all MM cell lines and MM patient cells, with one cell line (KMS-18) demonstrating a deletion affecting only these three genes, and with the exception of one patient sample (MCR263) were the deletion apparently terminated at the 3' end of YAP1 (FIG. 4B). At the expression level, the probe sets reporting for YAP1 reflected low values overall, also in normal hematopoietic tissues. However, when MM patient populations were subdivided in two groups based on YAP1 expression, low-expressors had a significantly worse survival than higher-expressors (FIG. 4C). We also compared the expression level of YAP1 in normal plasma cells, MGUS, and MM cells in various datasets. There was a consistent, significant reduction in YAP1 expression levels, starting from normal plasma cells, to MGUS, to MM (FIG. 4D and FIGS. 4F-4H). As for the MM cell lines, there are subsets presenting YAP1 homozygous deletions (KMS-18, KMS-20 and KMS-28PE); others with no detectable YAP1 at the mRNA and protein level, despite no genomic losses at chromosome 11; and finally cell lines with robust expression of the gene (UTMC-2, RPMI-8226 and MM1R)(FIG. 4E). We confirmed that the deletion in MM cell lines KMS-18 and KMS-20 affected not only BIRC2 and BIRC3 but also YAP1, at the DNA, mRNA and protein levels (FIG. 4E). These results suggest that YAP1 is homozygously deleted in a subset of MM patients, while in another broader group of patients characterized by a poor prognosis its expression levels are as low as in deleted samples. Moreover, there is a trend toward a reduction in YAP1 expression moving from normal plasma cells, to MGUS and finally to MM patients.

YAP1 Re-Expression in MM Cell Lines Induces ABL1-Mediated Apoptosis

We next sought to explore the functional role of YAP1 in MM. To this end, both loss-of- and gain-of-function approaches were undertaken. In the gain-of-function experiments, a cDNA coding for YAP1 fused with EGFP was reintroduced in KMS-18 and KMS-20 cells, where the YAP1 locus is deleted. Previous studies have shown that this fusion protein is as functional as the native form (Basu et al., 2003). In both cell lines, a robust expression of YAP1 mRNA and protein upon transfection was obtained (FIG. 5A). YAP1 re-expression significantly reduced cell number in both MM cell lines and dramatically increased apoptosis, as evaluated with PI staining. Specifically, at 72 hours after transfection PI positive cells were 25.7% and 37.1% in YAP1-KMS-20 and YAP1-KMS-18, versus 4.2% and 5.11% in cells transfected with the empty vector (FIG. 5A). A similar profile was observed using Annexin V-PE/7AAD staining (FIG. 5H and data not shown). For knockdown experiments, five shRNAs targeting YAP1 were evaluated: two shRNAs, shRNA #1 and shRNA #3, were chosen as they demonstrated a robust knockdown of YAP1 (FIG. 5B and data not shown). Downregulation of YAP1 in the UTMC-2 MM cell line induced a significant increase in proliferation and survival, proportional to the reduction in YAP1 levels. Importantly, overexpression of YAP1 in this same cell line, UTMC-2, already expressing the gene did not affect cell count or apoptosis (FIG. 5C). Similar results were obtained in another YAP1-expressing MM cell line, RPMI-8226 (FIG. 5I and data not shown). These data suggest that YAP1 behaves as a tumor suppressor gene in MM cells in which it is deleted and ongoing DNA damage is present. To further confirm the role of YAP1 in DNA-damage induced apoptosis in MM, YAP1 was silenced in UTMC-2 cells, that were then incubated with doxorubicin. By MTT assay, stable silenced MM cell lines presented a lower percentage of apoptotic cells (15.8% versus 37.4%) when compared to control cells. We also treated KMS20-YAP1 versus control cells with doxorubicin: viability and cell growth in YAP1-cells treated with doxorubicin was decreased (FIG. 5D). These results suggest that YAP1 participates in the apoptotic response induced by DNA-damaging agents, since its deletion or reduced expression decreases apoptosis triggered by doxorubicin.

As mentioned above, a consistent number of MM patients and MM cell lines do not have deletions at chromosome 11 where YAP1 resides and nevertheless lack expression of YAP1. We therefore assessed whether the reintroduction of YAP1 was also able to affect cell proliferation and apoptosis in this MM subset. YAP1 overexpression in MM.1S cell line dramatically reduced proliferation and increased apoptosis to levels comparable to YAP1 levels-deleted cells (FIG. 5E and FIG. 5J). These results implies that re-expression of YAP1 might induce apoptosis and reduce proliferation not only in MM cells where YAP1 is deleted, but also in the larger patient dataset where YAP1 is not expressed despite normal copy number.

We next asked whether YAP1-induced apoptosis was mediated by the aberrant presence of ABL1 in the nucleus in MM cells. The selective activation of proapoptotic genes by YAP1 in response to cisplatin or γ-irradiation requires YAP1-phosphorylation by ABL1 (Levy et al., 2008). We therefore reintroduced YAP1 into KMS-18 and KMS-20 cells and ascertained whether imatinib was able to reduce the pro-apoptotic action of YAP1. As mentioned, these cell lines have a homozygous deletion in chromosome 11, intense γ-H2A.X staining, and robust expression of pro-apoptotic ABL1 in the nucleus. Of note, the apoptotic response induced by reintroduction of YAP1 was indeed significantly reduced by treatment with imatinib, from 32.8% to 9.1% apoptotic cells, suggesting that the apoptosis induced by ABL1 relocalization in the nucleus is mediated by YAP1 (FIG. 5F and FIG. 5K). Similar effects were obtained in the subset of MM cell lines which do not have YAP1 deletions but lack YAP1 expression, in which ongoing DNA damage and nuclear ABL1 similarly does not lead to apoptosis (FIG. 5K and data not shown). In conclusion, these results indicate that abundant nuclear ABL1 present in MM cells does not lead to apoptosis due to the absence of YAP1.

YAP1 Stabilizes p73 Upon DNA Damage in Multiple Myeloma.

YAP1 interacts with (Strano et al., 2001) and stabilizes p73 by preventing Itch-mediated ubiquitination (Levy et al., 2007; Strano et al., 2005). YAP1 enhances p73-induced apoptosis after treatment with DNA damaging agents, since it increases the transcription of p73 targets (Strano et al., 2005; Strano et al., 2001) and when phosphorylated, binds p73 and is recruited to pro-apoptotic promoters to induce apoptosis (Levy et al., 2008). We therefore explored the relationship between YAP1 and p73 upon DNA damage in MM. Doxorubicin induced YAP1, as well as p73, in MM.1S and U266 cells (FIG. 6A). In contrast, imatinib-mediated inhibition of ABL1 stifled the increase in YAP1, p73 and p73-target expression triggered by DNA-damaging agents, further confirming the role of the ABL1-YAP1-p73 axis in DNA damage response in MM.

Moreover, re-expression of YAP1 in the deleted MM cell lines induced a remarkable increase of p73 protein levels (FIG. 6B). This increase was due to heightened stabilization of the protein, since p73 transcription was not affected appreciably by YAP1 modulation (FIG. 6B), consistent with previous studies (Strano et al., 2005). In contrast, p53 and TP63 (p63) protein levels were not altered upon YAP1 levels re-expression (FIG. 6C). We then assessed the levels of transcriptional p73 targets. Indeed, known p73 target genes, such as BAX, PUMA and $CDKN1A^{p21cIP1}$ significantly increased. In contrast, the protein level of the p53/p73 target NOXA did not vary upon YAP1 levels overexpression, confirming the target specificity conferred by YAP1, in line with previous reports (Strano et al., 2005).

In all, these results suggest that in MM the apoptosis induced by DNA damage and YAP1 re-expression is mediated by the stabilization of p73 and the increased expression of its downstream pro-apoptotic targets.

The Inactivation of the Hippo Kinase STK4 Leads to Increased YAP1 Levels and Apoptosis in MM Cells.

DNA damage and ABL1 can stabilize the short-lived YAP1 levels protein (Lapi et al., 2008). Indeed, treatment with proteasome inhibitors for 1-2 hours increased YAP1 protein levels in MM cell lines (data not shown). Nevertheless, YAP1 protein levels are in most MM cases exceedingly low, even in the absence of deletions affecting this gene. We thus reasoned that additional mechanisms affecting YAP1 levels might prevent its accumulation in MM. It has been reported that a cytoplasmic serine-threonine kinase, STK4, interacts with LATS1 and thereby significantly reduces YAP1 levels (Zhou et al., 2009; Zhou et al., 2011). We found strong expression of STK4 in MM cell lines and MM patient cells, as well as in normal plasma cells and lymphocytes (FIG. 7F). We therefore determined whether STK4 might regulate YAP1 levels in MM cells. To this end, five shRNAs directed against STK4 were introduced into MM cell lines, and STK4 mRNA and protein levels assayed. Four out of 5 were able to reduce STK4 expression levels in MM cell lines (FIG. 7A and data not shown). We then assessed whether STK4 inhibition modulated YAP1 levels in these cells. Indeed, STK4 downregulation was associated with a strong upregulation of YAP1 levels, compared to scrambled shRNA (FIG. 7A). We next assessed whether the upregulation of YAP1 induced by STK4 knockdown was associated with increased apoptosis. Indeed, all shRNAs induced a robust apoptotic response. In particular, these effects were evident both in basal conditions and after treatment with bortezomib and doxorubicin, suggesting a possible MM cell enhanced apoptosis in combination with drugs commonly used in the clinic (FIG. 7A). These results suggest that the YAP1 downregulation seen in MM patients and cell lines in the absence of chromosome 11 deletion could be due to an inhibitory effect of STK4 upon YAP1 levels.

Figure 11A:
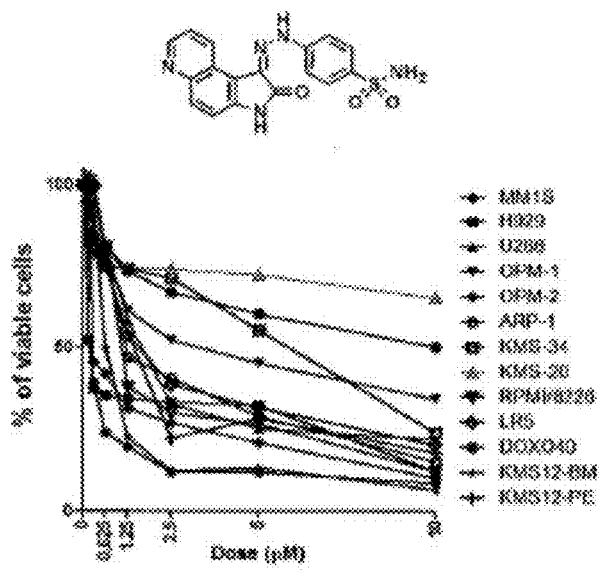
FIGS. 11A-11E show inhibition effects of GW305178X and compound 6.44.
Figure 11B:
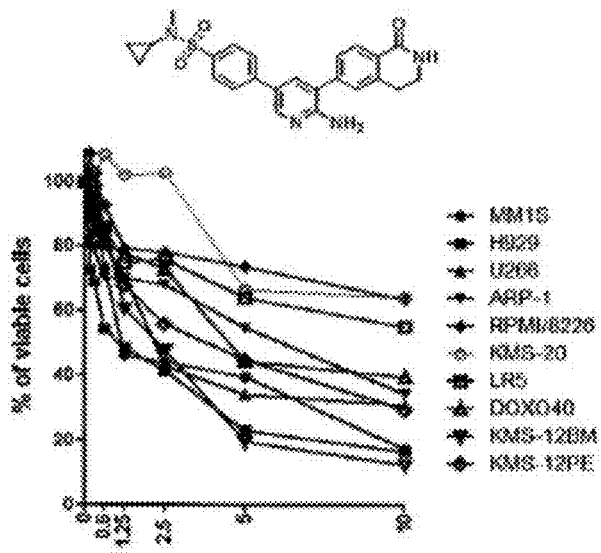
Figure 11C:
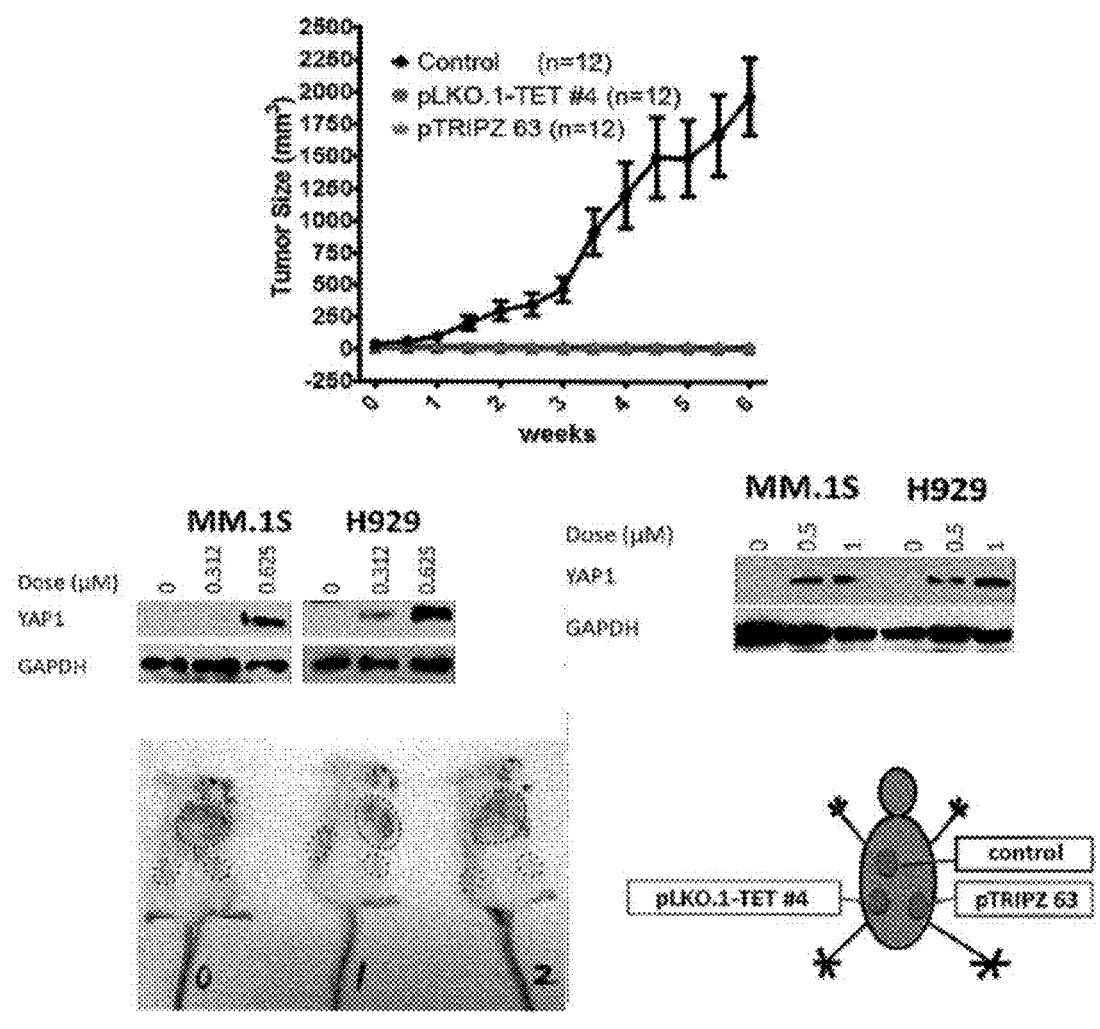
Figure 11D:
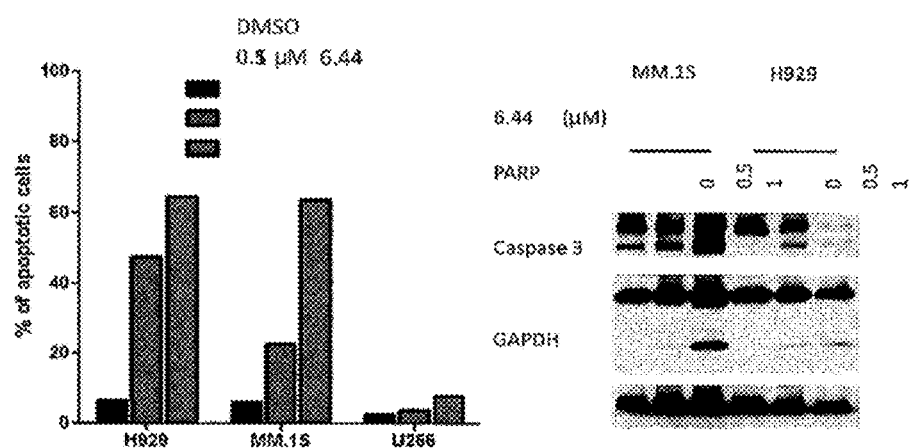

Next, we investigated the effects of pharmacological inhibition of STK4 on YAP1 levels and cell viability in a panel of MM cell lines. To date inhibitors specifically targeting the STK4 kinase hayed not been reported. To identify potential compounds targeting this kinase, we mined the Kinase SARfari integrated chemogenomics platform (Knapp et al., 2013)(https://www.ebi.ac.uk/chembl/sarfari/kinasesarfari) and assayed the biochemical $IC_{50}$ of the most promising compounds. One compound GW305178X (FIG. 11A) induced very potent inhibition of STK4, with a biochemical $IC_{50}$ of 12 nM. As in our experiments with shRNAs, we assayed its ability to impact on cell growth in a large panel of MM cell lines. Indeed, GW305178X reduced proliferation in most cell lines with low YAP1 levels (FIG. 11A) but was not active against KMS-20, a cell line with deleted YAP1. To further confirm the notion that GW305178X triggers apoptosis through increased YAP1, we assessed YAP1 levels in MM cells after treatment. Indeed, a robust increase in YAP1 levels was evident after treatment with GW305178X. In the course of these studies, we learned of a series of compounds targeting members of the STK family developed by Lexicon Pharmaceutical (Augeri D J et al, 2013) and identified one compound 6.44 (FIG. 11B), which demonstrated potent biochemical inhibition of STK4 with an $IC_{50}$ of 8 nM. 6.44 reduced cell growth and induced apoptosis in MM cell lines (FIG. 11A and FIG. 11D). Of note and as with GW305178X, the KMS-20 cell line, with YAP1 deletion, was not sensitive to the treatment with 6.44. Importantly, YAP1 expression was induced by 6.44 treatment, suggesting that reduced proliferation and cell death induced by 6.44 is at least partially mediated by YAP1. Therefore these data, coupled with our shRNA data, indicate that small molecule inhibition of STK4 kinase activity leads to increased levels of YAP1, associated with reduced growth and survival, in MM cell lines with ongoing DNA damage.

Figure 11E:
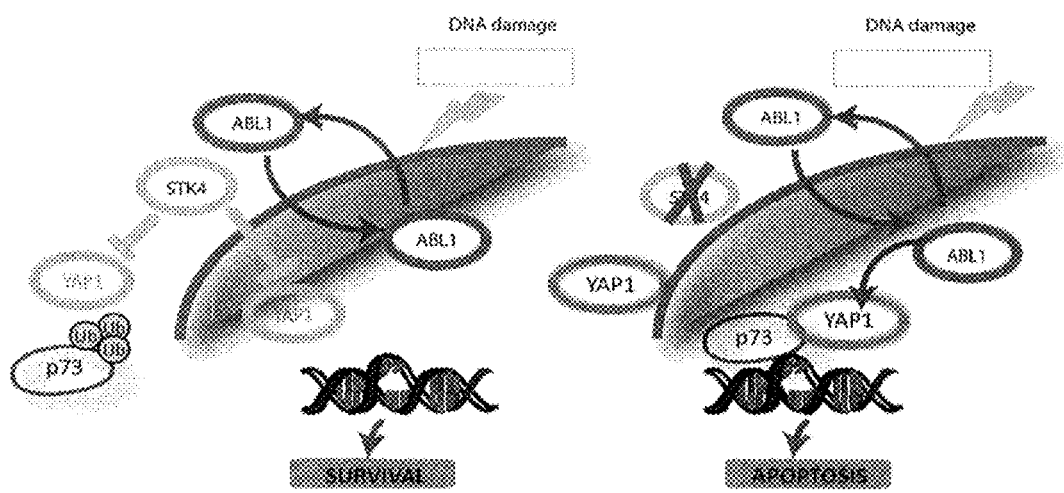

To demonstrate in vivo the relevance of this synthetically lethal interaction, a xenograft mouse model was used. A genetic approach conditionally knocking down STK4 in MM.1S cells was performed. In this study, MM.1S MM cells were infected with either inducible scrambled shRNAs, or inducible pLKO.1-TET shRNA #4 and pTRIPZ 63 directed against STK4 and then injected subcutaneously into three sites (left and right flank and interscapular region) in a group of 12 Fox Chase SCID mice. Tumors developed only from the xenografts derived from MM.1S cells infected with scrambled shRNAs, reaching a size of 1965 mm$^3$+/− 300 mm$^3$ at 6 weeks, while no growth was evident in STK-4 silenced cells (p<0.0001; FIG. 11C). Taken together, our results demonstrate that STK4 inhibition upregulates YAP1 levels in MM cells, thereby triggering apoptosis, both in vitro and in vivo (FIG. 11E).

Figure 12A:
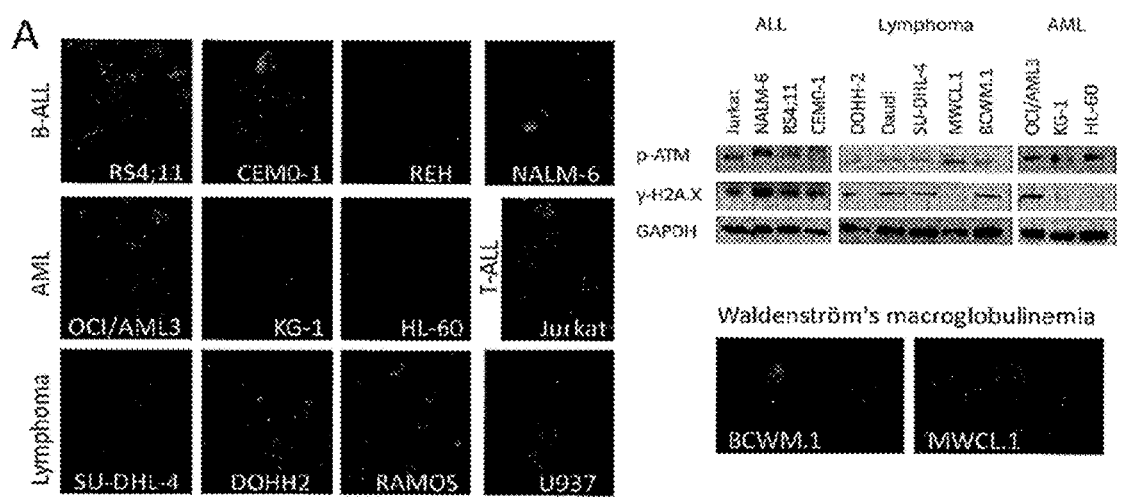
FIGS. 12A-12H show prominent ongoing DNA damage, ABL1 nuclear re-localization, STK4-medicated re-expression of YAP1 and apoptosis in lymphoma and leukemia cells.
Figure 12B:
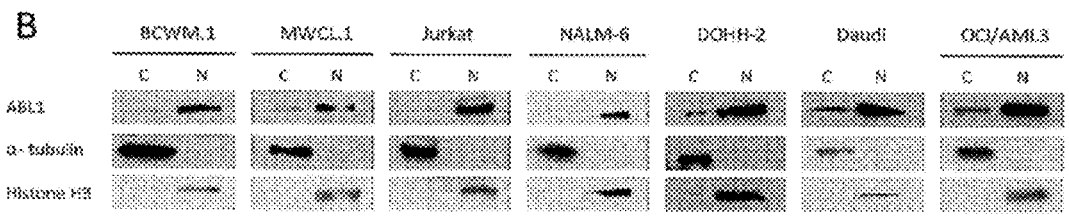
Figure 12C:
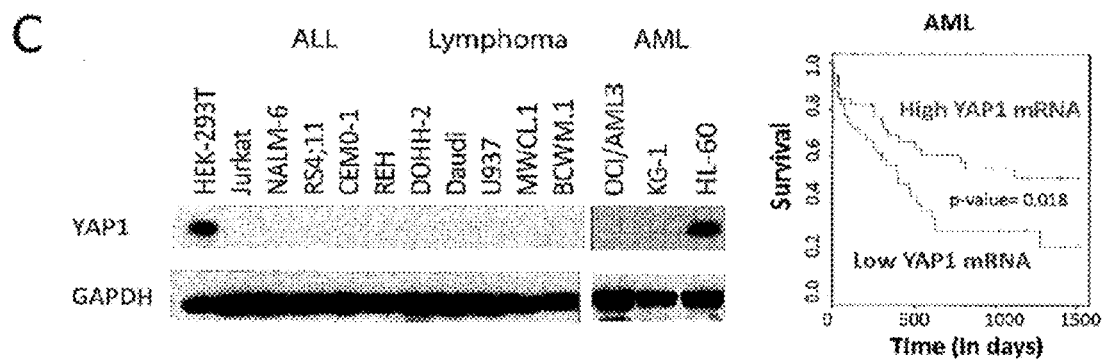
Figure 12D:
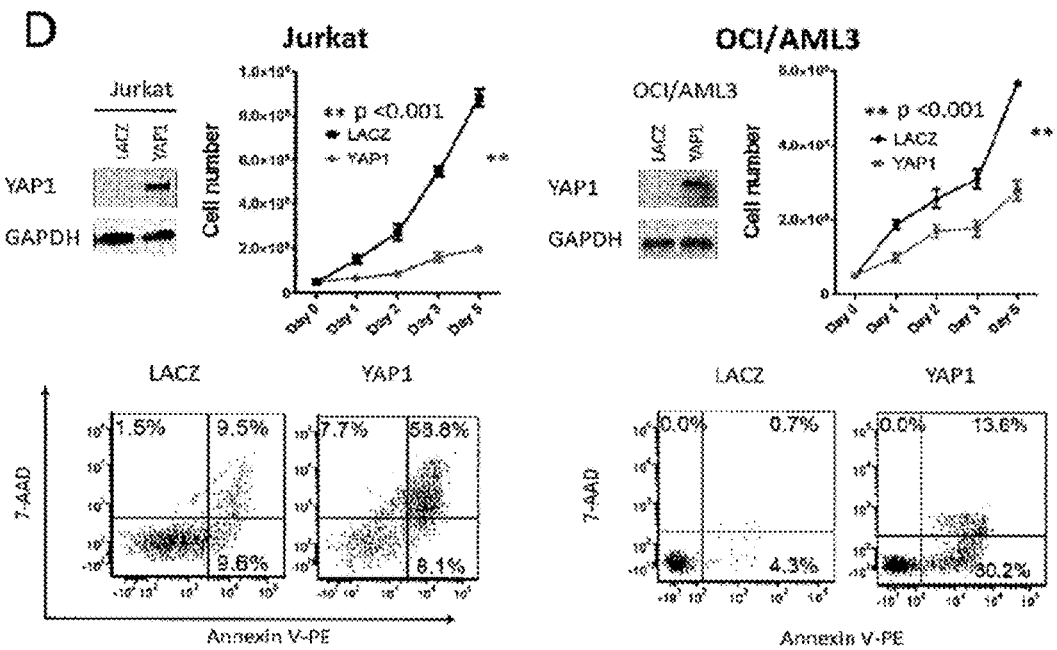
Figure 12E:
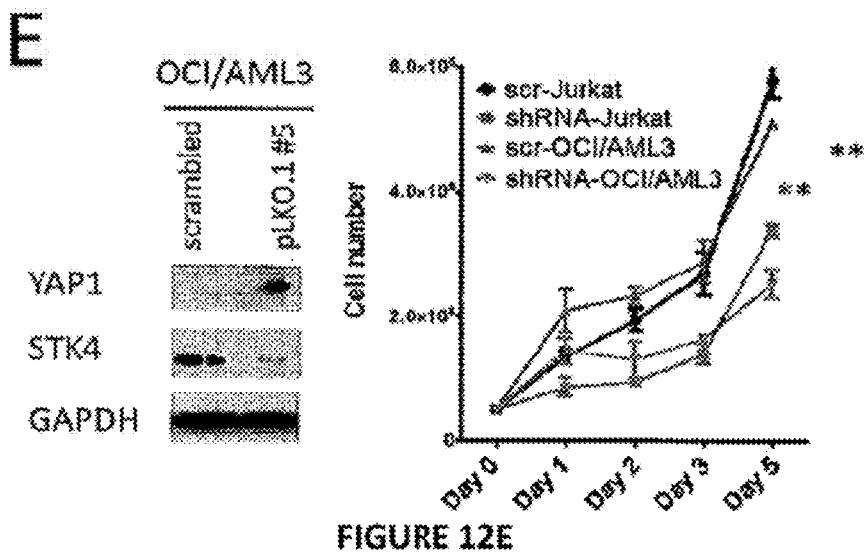
Figure 12F:
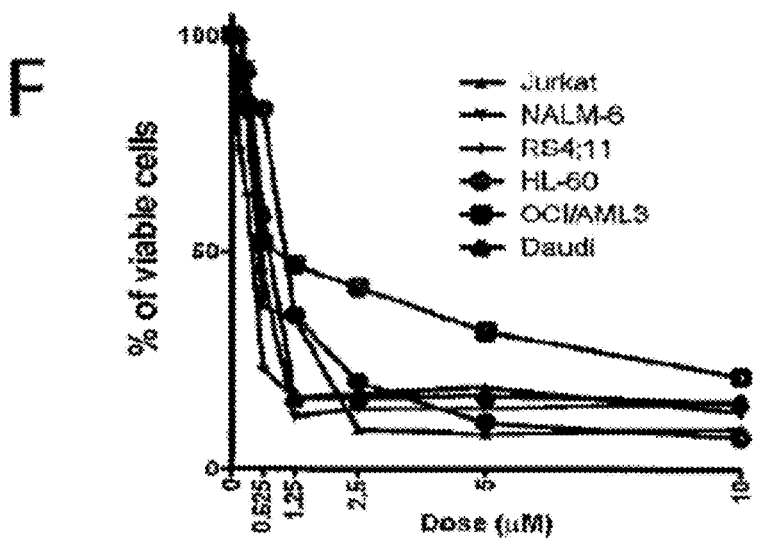
Figure 12G:
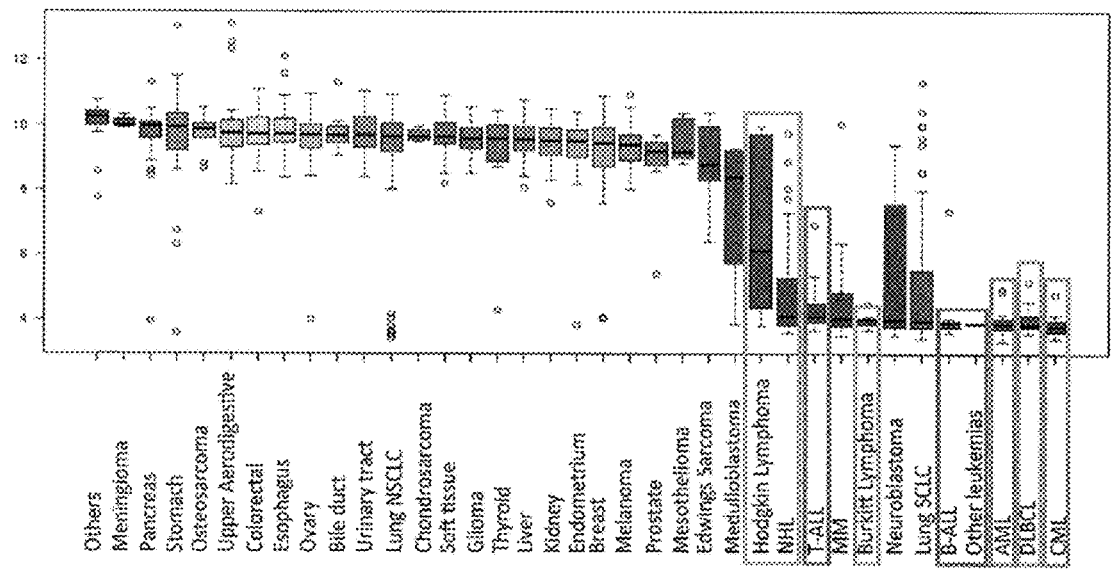

Prominent Ongoing DNA Damage, ABL1 Nuclear Re-Localization, STK4-Mediated Re-Expression of YAP1 and Apoptosis in Lymphoma and Leukemia Cells We next assessed DNA damage in a panel of lymphoma, lymphoblastic and myeloblastic leukemias, and Waldenström macroglobulinemia cell lines. Staining with γ-H2A.X revealed a ongoing DNA damage in the majority of the cell lines (FIG. 12A). Moreover, consistent nuclear localization of ABL1 was evident (FIG. 12B). YAP1 mRNA and protein levels were low, as in line with MM (FIG. 12C and FIG. 12G). Remarkably, and similar to MM, leukemia patients with low YAP1 expression had a significantly worse prognosis (FIG. 12C).

Figure 12H:
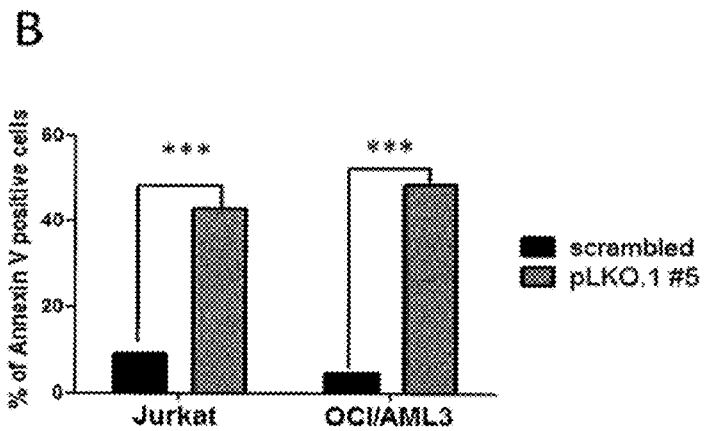

In MM cells, reintroduction of YAP1 in cells with YAP1 deletion or low expression induced a robust apoptotic response. We next asked whether this was also true in other hematological cancers. The reintroduction of YAP1 in ALL (Jurkat) and AML (OCI/AML3) cell lines decreased cell number, associated with apoptosis (FIG. 12D). As in MM, STK4 reduction through either STK4 shRNAs or treatment with the GW305178X compound increased YAP1 levels, reduced cell number, and enhanced apoptosis (FIGS. 12E-F and FIG. 12H).

STK4 pharmacological inhibition leads to apoptosis in the subset of MM cells with no YAP1 expression.

Small molecules already in use in the clinic, including SKI-606 targeting ABL/SRC and HKI-272 blocking HER2, have demonstrated activity against STK4 as well (Anastassiadis et al., 2011; Davis et al., 2011). We independently confirmed that SKI-606 and HKI-272 inhibit STK4, with a biochemical $IC_{50}$s of 33 and 28.2 nM, respectively. Given our results with shRNAs targeting STK4, the ability of these compounds to induce apoptosis through inducing the re-expression of YAP1 was assayed. Upon treatment of MM.1S cell line and U266 MM cell line with 10 μM SKI-606, a significant increase of YAP1 expression was evident. The second inhibitor HKI-272 gave similar results (FIG. 7B and FIGS. 7G-7H). Importantly, apoptosis in MM.1S and U266 increased from 11% and 10% to 76% and 58%, respectively, with SKI-606 treatment; and to 67% and 43%, respectively, with HKI-272 treatment, suggesting that STK4 inhibition leads to apoptosis through re-expression of YAP1. Of note, even though U266 cells did not show basal DNA damage, these drugs were able to induce a response, possibly mediated by ongoing low-level DNA damage that upon YAP1 re-expression is nevertheless able to activate the DDR/nuclear ABL1 axis. We next examined the growth inhibitory effect of these compounds. Both drugs significantly inhibited the growth of MM cell lines. As controls, similar experiments were conducted in KMS-18 and KMS-20 MM cell lines deleted for YAP1, as well as in the YAP1- expressing UTMC-2 and RPMI-8226 cell lines. In these cases, only a marginal increase in apoptosis was seen (FIG. 7C).

Given the role of YAP1 in DNA-damaging agents mediated apoptosis, we hypothesized that inhibition of STK4 resulting in YAP1 upregulation could enhance cytotoxicity of doxorubicin itself. We cultured MM.1S with doxorubicin in the presence of absence of STK4 inhibitors. Both STK4 inhibitors increased doxorubicin-induced apoptosis (FIG. 7D). Importantly, co-incubation of these STK4 inhibitors with Bortezomib increased apoptosis even in bortezomib resistant U266 cells (FIG. 7I).

Figure 9J:
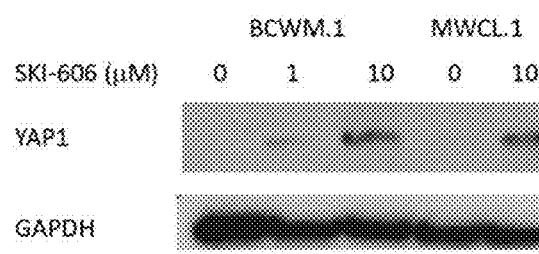

DNA DAMAGE-ABL1-YAP1 Axis is Active and Therapeutically Exploitable in a Subset of Leukemia and Lymphoma Cells Given the expression pattern for YAP1 reported in FIG. 4A, that suggested that YAP1 downregulation could pervasively affects haematological disorders in general, we assessed whether the axis DNA-Damage and ABL1 nuclear relocalization was present also in other haematological conditions. Indeed, markers of DNA double strand breaks, that is phosphorylated form of H2A.X, were identified in different haematological disorders, including waldestrom macroglobulinemia (MWCL.1 and BCWM.1), T-ALL (T-acute lymphoblastic leukemia) and AML (OCI-AML3) cell lines (FIG. 9E) by immunofluorescence. Moreover, a predominant ABL1 nuclear localization was present in these cell lines, but not in RL cell line (FIG. 9F), also in line with the results in MM cells, YAP1 levels were generally low in leukemia and lymphoma cell lines, with some exceptions such as HL-60 cell line (FIG. 9G). We then tested SKI-606 and HKI-272 compounds in a panel of leukemia and lymphoma cell lines, evaluating growth inhibitory effects by MTT absorbance assay and apoptosis by Annexin V-PI staining. As shown in FIG. 9H and FIG. 9I, cellular proliferation and survival was profoundly reduced in cell lines where the DNA damage-ABL1-YAP1 axis was activated. In contrast cell lines who have YAP1 basal expression (HL-60) or no nuclear ABL1 (RL) did not respond to the treatment. Western blot analysis confirmed YAP1 re-expression after drug modulation as in MM (FIG. 9J). These data suggest that this axis can be important in several hematopoietic disorders.

DISCUSSION

These results demonstrate that the intense DNA damage occurring in the majority of MM cells leads to relocalization of the tyrosine kinase ABL1 into the nucleus, where it has been shown to be pro-apoptotic. Despite high levels of nuclear ABL1, MM cells in a large subset of patients escape apoptosis as a result of genetic inactivation or exceedingly reduced expression of the Hippo co-transcription factor YAP1. Functional or pharmacological inhibition of STK4 restores YAP1 levels and triggers MM cell apoptosis in the large subset of MM cells where YAP1 levels is downregulated in the absence of homozygous deletions (FIG. 7E). These results uncover for the first time an unexpected, much wider, role for ABL1 in inducing apoptosis in the DDR response, demonstrate how MM cells prevent ABL1-mediated apoptosis through inactivation of the YAP1/p73 axis, and have important therapeutic implications for the large MM patient population that present ongoing DNA damage associated with YAP1 low expression, in the absence of homozygous deletions affecting its locus.

Besides its oncogenic role as BCR-ABL chimera, ionizing radiation and alkylating agents activate ABL1 leading to its relocalization in the nucleus, where ABL1 is a potent inducer of apoptosis (Kharbanda et al., 1995; Yuan et al., 1997). The findings reported herein implicate ABL1 relocalization as one of the crucial responses in cells following DNA damage, not only after treatment with high-dose DNA damaging drugs or radiation, but also as a consequence of ongoing, endogenous DNA damage. These data may partially explain the disappointing results obtained in phase II clinical trials of imatinib as a treatment for MM (Dispenzieri et al., 2006). In hindsight, ABL1 inhibitors may even have a detrimental effect in MM, relieving the pressure upon MM cells to undergo apoptosis as the result of nuclear relocalization of ABL1.

Despite the presence of functional ABL1 in the nucleus, MM cells do not undergo apoptosis. We here delineated the mechanism underlying this protective effect. ABL1 phosphorylates and interacts with YAP1. Focal homozygous deletions have been identified in a subset of MM patients affecting the chromosome 11 locus, and the NF-LIB inhibitors BIRC2 and BIRC3 have been named as the targets of this deletion. However, our analysis of the available literature confirms previous observations, suggesting that this deletion entails additional genes, including YAP1 (Carrasco et al., 2006; Walker et al., 2010). The reintroduction of YAP1 into homozygously-deleted MM cell lines induced robust apoptosis, suggesting that YAP1 may also be a target of this deletion. These results are intriguing since this chromosome 11 locus is often focally amplified in a vast array of solid tumors, including brain cancers, colon and hepatocellular carcinomas and an oncogenic role for YAP1 has been suggested in epithelial cancers (Pan, 2010). Intriguingly, YAP1 seems to cooperate as an oncogene with BIRC2 in liver cancer (Zender et al., 2006). Despite the extensive literature supporting YAP1, BIRC2, and BIRC3 as oncogenes in solid tumors, the data provided herein support a possible role for both YAP1 and BIRC2 as tumor suppressor genes in MM.

A possible explanation for this duplicitous behavior may rest on the ability of YAP1 to form complexes with various partners, with opposing functional consequences, depending on the cellular context (Bertini et al., 2009). For example, in the absence of DNA damage YAP1 preferentially interacts with the oncogenic transcription modulator RUNX leading to increased degradation of p73 (Levy et al., 2007). Thus, transcription modulators appear to stir YAP1 away from p73 and towards other partners, thereby endowing YAP1 with proliferative and anti-apoptotic features.

It has long been recognized that MGUS plasma cells have higher degrees of apoptosis than both smoldering MM and overt MM (Witzig et al., 1999). Ongoing DNA damage has been reported in MGUS (Walters et al., 2011), suggesting that DNA replication stress induced by oncogene activation could trigger a DNA damage response and apoptosis in this condition, as in other pre-malignant states. Therefore, as in neoplasms of epithelial origin (Halazonetis et al., 2008), it stands to reason to hypothesize that activation of the DNA damage checkpoint in MGUS might be a barrier against the evolution towards MM. Inactivation of p53 has been proposed as the genetic event that in epithelial cancers dictates the transition toward a more aggressive disease (Gorgoulis et al., 2005). In our screen, the ongoing DNA damage in MM was not reliably followed by p53 activation, as evaluated by p53 phosphorylation at the Serine 15 residue. Instead, the correlation between ongoing DNA damage and ABL1 relocalization was very strong, suggesting that this pathway is the main conduit of DDR signaling, rather than the p53 axis. Additionally, decreasing expression levels of YAP1 levels with progression from MGUS to MM suggests that this gene may represent, along with p73, the gatekeeper in MGUS preventing evolution to MM; conversely, inactivation of YAP1, either by focal deletions or more generally reduced expression, would allow MGUS cells to evolve toward MM. The early inactivation of the ABL1/YAP1/p73 axis may represent one of the events substituting p53 mutations in hematological cancers, where p53 inactivation presents low incidence and appears late during the progression.

Kinases are ideal targets for cancer therapies, as already proven by imatinib, Tarceva and Iressa. Therefore the role of STK4 in increasing the levels of YAP1 levels provides for the treatment of MM with undetectable levels of YAP1 levels and concomitant DNA damage. Importantly, shRNA- or drug-mediated STK4 inactivation induced apoptosis in both p53-WT and mutant cells, suggesting that restoring YAP1 levels represent a promising treatment strategy for the tumors presenting with p53 inactivation, which confers an adverse prognosis and therefore represents an important unmet medical need. Given that ongoing DNA damage is a feature of tumor cells, the present invention provides a synthetic-lethal approach (Kaelin, 2005) whereby tumor cells with endogenous DNA damage and YAP1 levels inactivation are selectively targeted by inhibitors of STK4 activity to induce tumor cell apoptosis.

REFERENCES

Anastassiadis, T., Deacon, S. W., Devarajan, K., Ma, H., and Peterson, J. R. (2011). Comprehensive assay of kinase catalytic activity reveals features of kinase inhibitor selectivity. Nature biotechnology 29, 1039-1045.

Annunziata, C. M., Davis, R. E., Demchenko, Y., Bellamy, W., Gabrea, A., Zhan, F., Lenz, G., Hanamura, I., Wright, G., Xiao, W., et al. (2007). Frequent engagement of the classical and alternative NF-kappaB pathways by diverse genetic abnormalities in multiple myeloma. Cancer Cell 12, 115-130.

Bartkova, J., Horejsi, Z., Koed, K., Kramer, A., Tort, F., Zieger, K., Guldberg, P., Sehested, M., Nesland, J. M., Lukas, C., et al. (2005). DNA damage response as a candidate anti-cancer barrier in early human tumorigenesis. Nature 434, 864-870.

Baskaran, R., Wood, L. D., Whitaker, L. L., Canman, C. E., Morgan, S. E., Xu, Y., Barlow, C., Baltimore, D., Wynshaw-Boris, A., Kastan, M. B., et al. (1997). Ataxia telangiectasia mutant protein activates c-Abl tyrosine kinase in response to ionizing radiation. Nature 387, 516-519.

Basu, S., Totty, N. F., Irwin, M. S., Sudol, M., and Downward, J. (2003). Akt phosphorylates the Yes-associated protein, YAP, to induce interaction with 14-3-3 and attenuation of p73-mediated apoptosis. Mol Cell 11, 11-23.

Bertini, E., Oka, T., Sudol, M., Strano, S., and Blandino, G. (2009). YAP: at the crossroad between transformation and tumor suppression. Cell Cycle 8, 49-57.

Boehrer, S., Ades, L., Tajeddine, N., Hofmann, W. K., Kriener, S., Bug, G., Ottmann, O. G., Ruthardt, M., Galluzzi, L., Fouassier, C., et al. (2009). Suppression of the DNA damage response in acute myeloid leukemia versus myelodysplastic syndrome. Oncogene 28, 2205-2218.

Brown, L., and McCarthy, N. (1997). DNA repair. A sense-abl response? Nature 387, 450-451.

Carrasco, D. R., Tonon, G., Huang, Y., Zhang, Y., Sinha, R., Feng, B., Stewart, J. P., Zhan, F., Khatry, D., Protopopova, M., et al. (2006). High-resolution genomic profiles define distinct clinico-pathogenetic subgroups of multiple myeloma patients. Cancer Cell 9, 313-325.

Chapman, M. A., Lawrence, M. S., Keats, J. J., Cibulskis, K., Sougnez, C., Schinzel, A. C., Harview, C. L., Brunet, J. P., Ahmann, G. J., Adli, M., et al. (2011). Initial genome sequencing and analysis of multiple myeloma. Nature 471, 467-472.

Davis, M. I., Hunt, J. P., Herrgard, S., Ciceri, P., Wodicka, L. M., Pallares, G., Hocker, M., Treiber, D. K., and Zarrinkar, P. P. (2011). Comprehensive analysis of kinase inhibitor selectivity. Nature biotechnology 29, 1046-1051.

De Vos, J., Thykjaer, T., Tarte, K., Ensslen, M., Raynaud, P., Requirand, G., Pellet, F., Pantesco, V., Reme, T., Jourdan, M., et al. (2002). Comparison of gene expression profiling between malignant and normal plasma cells with oligonucleotide arrays. Oncogene 21, 6848-6857.

Dispenzieri, A., Gertz, M. A., Lacy, M. Q., Geyer, S. M., Greipp, P. R., Rajkumar, S. V., Kimlinger, T., Lust, J. A., Fonseca, R., Allred, J., et al. (2006). A phase II trial of imatinib in patients with refractory/relapsed myeloma. Leuk Lymphoma 47, 39-42.

Gorgoulis, V. G., Vassiliou, L. V., Karakaidos, P., Zacharatos, P., Kotsinas, A., Liloglou, T., Venere, M., Ditullio, R. A., Jr., Kastrinakis, N. G., Levy, B., et al. (2005). Activation of the DNA damage checkpoint and genomic instability in human precancerous lesions. Nature 434, 907-913.

Halazonetis, T. D., Gorgoulis, V. G., and Bartek, J. (2008). An oncogene-induced DNA damage model for cancer development. Science 319, 1352-1355.

Hickson, I., Zhao, Y., Richardson, C. J., Green, S. J., Martin, N. M., On, A. I., Reaper, P. M., Jackson, S. P., Curtin, N. J., and Smith, G. C. (2004). Identification and characterization of a novel and specific inhibitor of the ataxia-telangiectasia mutated kinase ATM. Cancer Res 64, 9152-9159.

Hideshima, T., Mitsiades, C., Akiyama, M., Hayashi, T., Chauhan, D., Richardson, P., Schlossman, R., Podar, K., Munshi, N. C., Mitsiades, N., et al. (2003). Molecular mechanisms mediating antimyeloma activity of proteasome inhibitor PS-341. Blood 101, 1530-1534.

Kaelin, W. G., Jr. (2005). The concept of synthetic lethality in the context of anticancer therapy. Nat Rev Cancer 5, 689-698.

Keats, J. J., Fonseca, R., Chesi, M., Schop, R., Baker, A., Chng, W. J., Van Wier, S., Tiedemann, R., Shi, C. X., Sebag, M., et al. (2007). Promiscuous mutations activate the noncanonical NF-kappaB pathway in multiple myeloma. Cancer Cell 12, 131-144.

Kharbanda, S., Ren, R., Pandey, P., Shafman, T. D., Feller, S. M., Weichselbaum, R. R., and Kufe, D. W. (1995). Activation of the c-Abl tyrosine kinase in the stress response to DNA-damaging agents. Nature 376, 785-788.

Lapi, E., Di Agostino, S., Donzelli, S., Gal, H., Domany, E., Rechavi, G., Pandolfi, P. P., Givol, D., Strano, S., Lu, X., et al. (2008). PML, YAP, and p73 are components of a proapoptotic autoregulatory feedback loop. Mol Cell 32, 803-814.

Levy, D., Adamovich, Y., Reuven, N., and Shaul, Y. (2007). The Yes-associated protein 1 stabilizes p73 by preventing Itch-mediated ubiquitination of p73. Cell Death Differ 14, 743-751.

Levy, D., Adamovich, Y., Reuven, N., and Shaul, Y. (2008). Yap 1 phosphorylation by c-Abl is a critical step in selective activation of proapoptotic genes in response to DNA damage. Mol Cell 29, 350-361.

Palumbo, A., and Anderson, K. (2011). Multiple myeloma. N Engl J Med 364, 1046-1060.

Pan, D. (2010). The hippo signaling pathway in development and cancer. Dev Cell 19, 491-505.

Shafman, T., Khanna, K. K., Kedar, P., Spring, K., Kozlov, S., Yen, T., Hobson, K., Gatei, M., Zhang, N., Watters, D., et al. (1997). Interaction between ATM protein and c-Abl in response to DNA damage. Nature 387, 520-523.

Strano, S., Monti, O., Pediconi, N., Baccarini, A., Fontemaggi, G., Lapi, E., Mantovani, F., Damalas, A., Citro, G., Sacchi, A., et al. (2005). The transcriptional coactivator Yes-associated protein drives p73 gene-target specificity in response to DNA Damage. Mol Cell 18, 447-459.

Strano, S., Munarriz, E., Rossi, M., Castagnoli, L., Shaul, Y., Sacchi, A., Oren, M., Sudol, M., Cesareni, G., and Blandino, G. (2001). Physical interaction with Yes-associated protein enhances p73 transcriptional activity. J Biol Chem 276, 15164-15173.

Sudol, M. (1994). Yes-associated protein (YAP65) is a proline-rich phosphoprotein that binds to the SH3 domain of the Yes proto-oncogene product. Oncogene 9, 2145-2152.

Taagepera, S., McDonald, D., Loeb, J. E., Whitaker, L. L., McElroy, A. K., Wang, J. Y., and Hope, T. J. (1998). Nuclear-cytoplasmic shuttling of C-ABL tyrosine kinase. Proc Natl Acad Sci USA 95, 7457-7462.

Takacova, S., Slany, R., Bartkova, J., Stranecky, V., Dolezel, P., Luzna, P., Bartek, J., and Divoky, V. (2012). DNA damage response and inflammatory signaling limit the MLL-ENL-induced leukemogenesis in vivo. Cancer Cell 21, 517-531.

Walker, B. A., Leone, P. E., Chiecchio, L., Dickens, N. J., Jenner, M. W., Boyd, K. D., Johnson, D. C., Gonzalez, D., Dagrada, G. P., Protheroe, R. K., et al. (2010). A compendium of myeloma-associated chromosomal copy number abnormalities and their prognostic value. Blood 116, e56-65.

Walters, D. K., Wu, X., Tschumper, R. C., Arendt, B. K., Huddleston, P. M., Henderson, K. J., Dispenzieri, A., and Jelinek, D. F. (2011). Evidence for ongoing DNA damage in multiple myeloma cells as revealed by constitutive phosphorylation of H2AX. Leukemia 25, 1344-1353.

White, E., and Prives, C. (1999). DNA damage enables p73. Nature 399, 734-735, 737.

Witzig, T. E., Timm, M., Larson, D., Therneau, T., and Greipp, P. R. (1999). Measurement of apoptosis and proliferation of bone marrow plasma cells in patients with plasma cell proliferative disorders. Br J Haematol 104, 131-137.

Xu-Monette, Z. Y., Medeiros, L. J., Li, Y., Orlowski, R. Z., Andreeff, M., Bueso-Ramos, C. E., Greiner, T. C., McDonnell, T. J., and Young, K. H. (2012). Dysfunction of the TP53 tumor suppressor gene in lymphoid malignancies. Blood 119, 3668-3683.

Yoshida, K., Yamaguchi, T., Natsume, T., Kufe, D., and Miki, Y. (2005). JNK phosphorylation of 14-3-3 proteins regulates nuclear targeting of c-Abl in the apoptotic response to DNA damage. Nat Cell Biol 7, 278-285.

Yuan, Z. M., Huang, Y., Ishiko, T., Kharbanda, S., Weichselbaum, R., and Kufe, D. (1997). Regulation of DNA damage-induced apoptosis by the c-Abl tyrosine kinase. Proc Natl Acad Sci USA 94, 1437-1440.

Yuan, Z. M., Huang, Y., Whang, Y., Sawyers, C., Weichselbaum, R., Kharbanda, S., and Kufe, D. (1996). Role for c-Abl tyrosine kinase in growth arrest response to DNA damage. Nature 382, 272-274.

Zender, L., Spector, M. S., Xue, W., Flemming, P., Cordon-Cardo, C., Silke, J., Fan, S. T., Luk, J. M., Wigler, M., Hannon, G. J., et al. (2006). Identification and validation of oncogenes in liver cancer using an integrative oncogenomic approach. Cell 125, 1253-1267.

Zhou, D., Conrad, C., Xia, F., Park, J. S., Payer, B., Yin, Y., Lauwers, G. Y., Thasler, W., Lee, J. T., Avruch, J., et al. (2009). Mst1 and Mst2 maintain hepatocyte quiescence and suppress hepatocellular carcinoma development through inactivation of the Yap1 oncogene. Cancer Cell 16, 425-438.

Zhou, D., Zhang, Y., Wu, H., Barry, E., Yin, Y., Lawrence, E., Dawson, D., Willis, J. E., Markowitz, S. D., Camargo, F. D., et al. (2011). Mst1 and Mst2 protein kinases restrain intestinal stem cell proliferation and colonic tumorigenesis by inhibition of Yes-associated protein (Yap) overabundance. Proc Natl Acad Sci USA 108, E1312-1320.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

The invention claimed is:

1. A method of treating a hematopoietic disorder in a subject comprising administering to said subject an effective amount of an agent that increases YAP1 levels, wherein said subject has been identified as having a hematopoietic disorder with reduced levels of YAP1, wherein the hematopoietic disorder has been identified as having nuclear localisation of ABL1 in hematopoietic cells associated with the disorder, and wherein the agent that increases YAP1 levels is an inactivator of STK4.

2. The method according to claim 1, wherein the hematopoietic disorder is selected from the group consisting of multiple myeloma, leukaemia or lymphoma.

3. A method according to claim 2 wherein the hematopoietic disorder is multiple myeloma.

4. A method according to claim 1, wherein the inactivator reduces expression of STK4.

5. A method according to claim 4, wherein the inactivator is a short hairpin RNA (shRNA), siRNA or a micro RNA (miRNA).

6. A method according to claim 1, wherein the agent comprises a shRNA having a sequence selected from the group consisting of SEQ ID NOs: 1, 2, 3 or 4.

7. A method according to claim 1, wherein the inactivator is an antagonist of STK4.

8. A method according to claim 1, wherein the agent is HKI-272.

9. A method according to claim 1, wherein the agent comprises a shRNA with a sequence of SEQ ID NO: 1, 2, 3 or 4, or wherein the agent is HKI-272.

10. A method according to claim 1, wherein the agent is comprised within a vector.

11. A method according to claim 1, wherein the hematopoietic disorder is selected from the group consisting of Waldenström macroglobulinemia, T-cell leukaemia, T-cell acute lymphoblastic leukaemia (T-ALL) and acute myeloid leukaemia (AML).

* * * * *